United States Patent

Or et al.

Patent Number: 6,034,069
Date of Patent: Mar. 7, 2000

[54] 3-'N-MODIFIED 6-O-SUBSTITUTED ERYTHROMYCIN KETOLIDE DERIVATIVES HAVING ANTIBACTERIAL ACTIVITY

[75] Inventors: Yat Sun Or, Libertyville; Zhenkun Ma, Gurnee, both of Ill.; Daniel T. Chu, Santa Clara, Calif.

[73] Assignee: Abbott Laboratories, Abbott Park, Ill.

[21] Appl. No.: 09/132,256

[22] Filed: Aug. 11, 1998

Related U.S. Application Data

[60] Provisional application No. 60/060,564, Sep. 30, 1997.

[51] Int. Cl.$^7$ .............................. A61K 31/70; C07H 1/00; C07H 17/08
[52] U.S. Cl. .............................. 514/29; 536/7.2; 536/7.9; 536/18.5
[58] Field of Search .............................. 536/7.2, 7.4, 18.5; 514/29

[56] References Cited

U.S. PATENT DOCUMENTS 5,444,051  8/1995  Agouridas et al. ..................... 514/29

FOREIGN PATENT DOCUMENTS 0215335  3/1987  European Pat. Off. .

(List continued on next page.)

OTHER PUBLICATIONS

Journal of Antibiotics, vol. 43 (1990), pp. 286–294, Morimoto, et al., "Chemical Modification of Erythromycins—II, Synthesis and Antibacterial Activity of O–Alkyl Derivatives of Erythromycin A".

(List continued on next page.)

*Primary Examiner*—Elli Peselev
*Attorney, Agent, or Firm*—Mona Anand

[57] ABSTRACT

Novel 3'-N-modified 6-O-substituted erythromycin ketolide compounds and pharmaceutically acceptable salts and esters thereof having antibacterial activity having a formula (I)

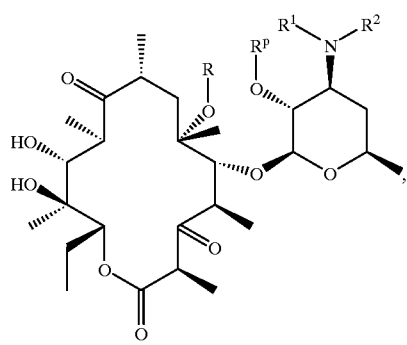

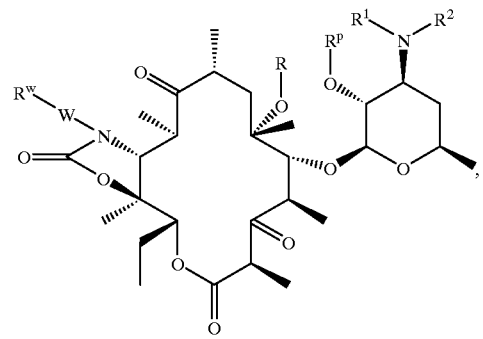

(II)

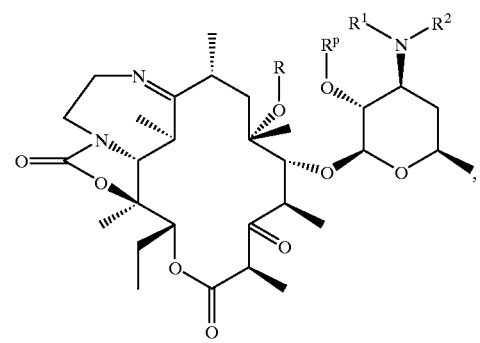

(III)

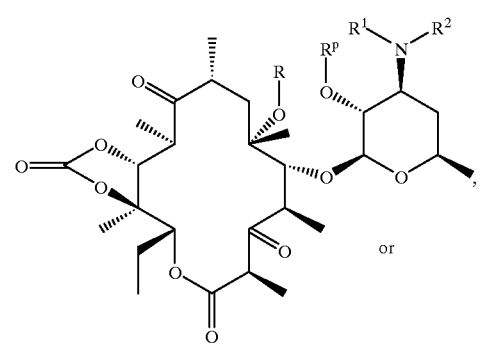

(IV)

or

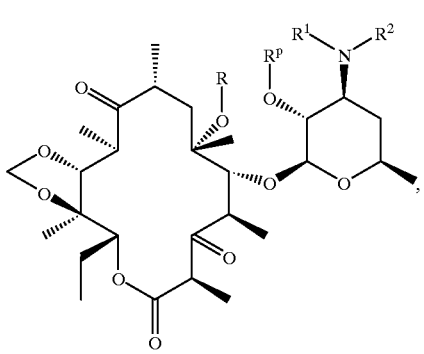

(V)

compositions comprising a therapeutically effective amount of a compound of the invention in combination with a pharmaceutically acceptable carrier, as well as a method for treating bacterial infections by administering to a mammal a pharmaceutical composition containing a therapeutically-effective amount of a compound of the invention.

15 Claims, No Drawings

FOREIGN PATENT DOCUMENTS

| | | |
|---|---|---|
| 0272110 | 6/1988 | European Pat. Off. . |
| 0596802 | 5/1994 | European Pat. Off. . |
| WO 9209614 | 6/1992 | WIPO . |
| WO 9710251 | 3/1997 | WIPO . |
| WO 9717356 | 5/1997 | WIPO . |

OTHER PUBLICATIONS

Journal of Pharmaceutical Sciences, vol. 79, No. 9 (Sep. 1989), pp. 783–784, Suwa, et al., "Uptake of O–Alkyl Erythromycin Derivatives in the Lung Tissue and Cells of Rats".

Journal of Antibiotics, vol. 37 (1984), pp. 187–189, Morimoto et al., "Chemical Modification of Erythromycins—I. Synthesis and Antibacterial Activity of 6–O–Methylerythromycins A".

3-'N-MODIFIED 6-O-SUBSTITUTED ERYTHROMYCIN KETOLIDE DERIVATIVES HAVING ANTIBACTERIAL ACTIVITY

This application is a continuation-in-part of provisional U.S. patent application Ser. No. 60/060,564 filed Sep. 30, 1997, pending.

TECHNICAL FIELD

This invention relates to novel semi-synthetic macrolides having antibacterial activity, to pharmaceutical compositions comprising these compounds, and to a medical method of treatment. More particularly, the invention relates to 3'-N-modified 6-O-substituted erythromycin ketolide derivatives and methods for preparing them, compositions containing these compounds, and a method of treating bacterial infections with such compositions.

BACKGROUND OF THE INVENTION

Erythromycins A through D, represented by formula (E),

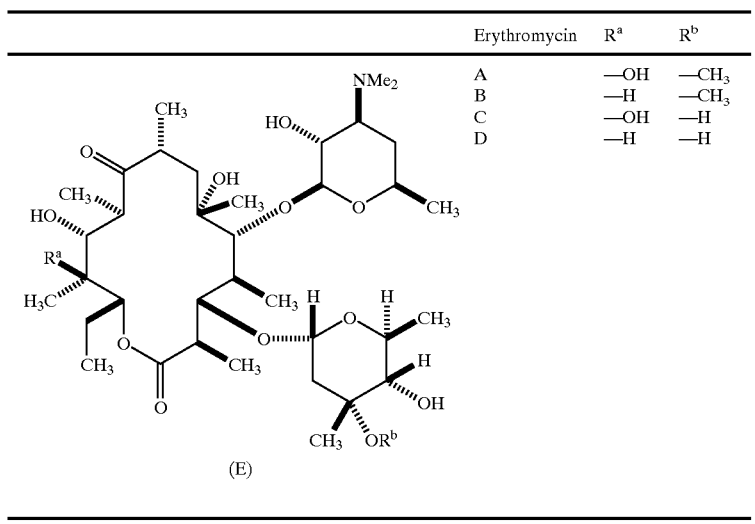

| Erythromycin | $R^a$ | $R^b$ |
|---|---|---|
| A | —OH | —$CH_3$ |
| B | —H | —$CH_3$ |
| C | —OH | —H |
| D | —H | —H |

(E)

are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Morimoto et al. describes the preparation of 6-O-methyl erythromycin A in J. Antibiotics 37:187 (1984). Morimoto et al. further discloses 6-O-alkyl erythromycin A derivatives in J. Antibiotics, 43:286 (1990) and in European Patent Application 272,110, published Jun. 22, 1988. European Patent Application 215,355, published Mar. 28, 1987, discloses 6-O-loweralkyl erythromycins as stimulants of gastrointestinal contractile motion.

U.S. Pat. No. 5,444,051 discloses 6-O-substituted-3-oxoerythromycin A derivatives in which the substituents are selected from alkyl, —$CONH_2$, —CONHC(O)alkyl and —$CONHSO_2$alkyl. PCT application WO 97/10251, published Mar. 20, 1997, discloses 6-O-methyl 3-descladinose erythromycin derivatives, and PCT application WO 97/17356, published May 15, 1997, discloses 3-deoxy-3-descladinose erythromycin derivatives. PCT application WO 92/09614, published Jun. 11, 1992, discloses tricyclic 6-O-methyl erythromycin A derivatives. Certain intermediates to the present invention are disclosed in U.S. patent application Ser. No. 08/888,350.

European Patent Application 596802, published May 11, 1994, discloses bicyclic 6-O-methyl-3-oxo erythromycin A derivatives.

SUMMARY OF THE INVENTION

The present invention provides a novel class of 3'-N-modified 6-O-substituted erythromycin ketolide derivatives which possess antibacterial activity.

In one aspect of the present invention are compounds, or pharmaceutically acceptable salts and esters thereof, having a formula selected from the group consisting of

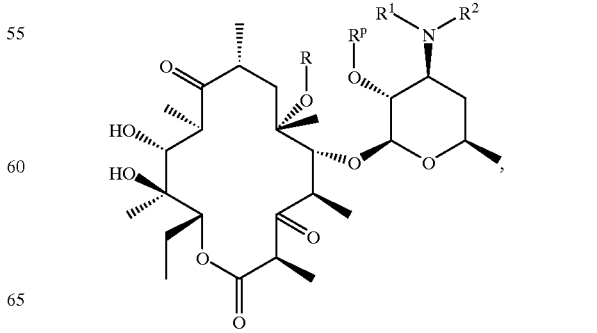

(I)

-continued

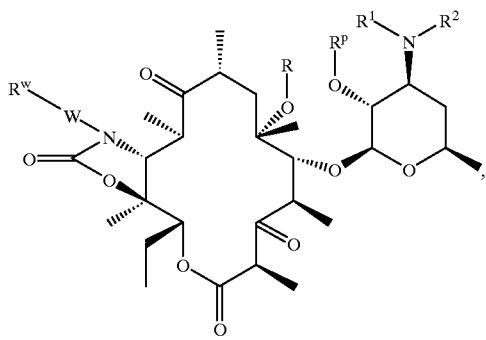
(II)

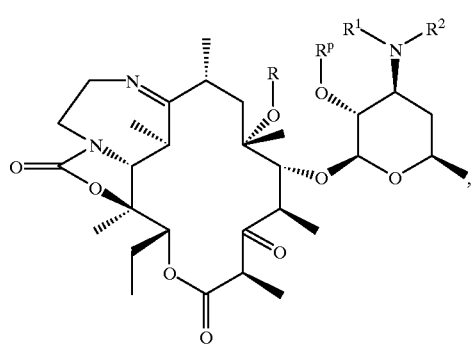
(III)

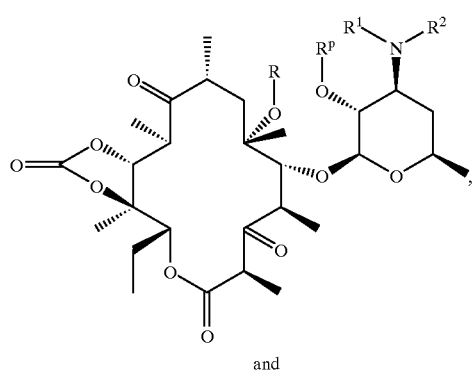
(IV)

and

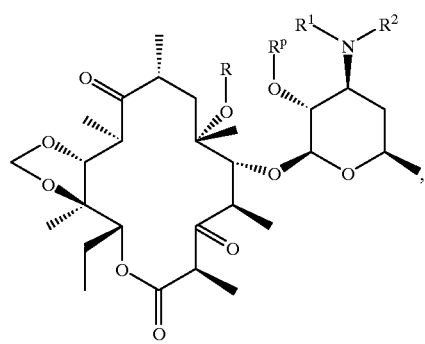
(V)

or a pharmaceutically acceptable salt, ester or prodrug thereof, wherein $R^1$ and $R^2$, with the proviso that $R^1$ and $R^2$ are not both methyl, are independently selected from the group consisting of
(1) hydrogen,
(2) $C_1$–$C_6$-alkyl optionally substituted with a substituent selected from the group consisting of
 (a) halogen,
 (b) $C_3$–$C_6$-cycloalkyl,
 (c) aryl,
 (d) substituted aryl,
 (e) heteroaryl,
 (f) substituted heteroaryl,
 (g) —CHO,
 (h) —C(O)—$C_1$–$C_6$-alkyl, and
 (i) —C(O)—NR'R", wherein R' and R" are independently selected from the group consisting of hydrogen, $C_1$–$C_3$-alkyl, $C_1$–$C_3$-alkyl substituted with aryl, substituted aryl, heteroaryl, and substituted heteroaryl,
(3) $C_2$–$C_6$-alkyl optionally substituted with a substituent selected from the group consisting of
 (a) $C_1$–$C_6$-alkoxy,
 (b) —NR'R", wherein R' and R" are as previously defined,
 (c) —NH—C(O)—$C_1$–$C_6$-alkyl,
 (d) —NH—C(O)—O—$C_1$–$C_6$-akyl,
 (e) —O—C(O)—O—$C_1$–$C_6$-alkyl,
 (f) —O—C(O)—$C_1$–$C_6$-alkyl,
 (g) —CH(=N—O—$C_1$–$C_6$-alkyl),
 (h) —C(=N—O—$C_1$–$C_6$-alkyl)—$C_1$–$C_6$-alkyl,
 (i) —CH(=N—NH—$C_1$–$C_6$-alkyl), and
 (j) —C(=N—NH—$C_1$–$C_6$-alkyl)—$C_1$–$C_6$-alkyl,
(4) $C_3$–$C_6$-alkenyl optionally substituted with a substituent selected from the group consisting of
 (a) halogen,
 (b) $C_3$–$C_6$-cycloalkyl,
 (c) aryl,
 (d) substituted aryl,
 (e) heteroaryl,
 (f) substituted heteroaryl,
 (g) —NH—C(O)—$C_1$–$C_6$-alkyl,
 (h) —NH—C(O)—O—$C_1$–$C_6$-alkyl,
 (i) —O—C(O)—O—$C_1$–$C_6$-alkyl,
 (j) —O—C(O)—$C_1$–$C_6$-alkyl,
 (k) —CHO,
 (l) —C(O)—$C_1$–$C_6$-alkyl,
 (m) —C(O)—NR'R", wherein R' and R" are as previously defined,
 (n) —CH(=N—O—$C_1$–$C_6$-alkyl),
 (o) —C(=N—O—$C_1$–$C_6$-alkyl)—$C_1$–$C_6$-alkyl,
 (p) —CH(=N—NH—$C_1$–$C_6$-alkyl),
 (q) —C(=N—NH—$C_1$–$C_6$-alkyl)—$C_1$–$C_6$-alkyl, and
 (r) —C(O)—O—$C_1$–$C_6$-alkyl,
(5) $C_3$–$C_6$-alkynyl optionally substituted with a substituent selected from the group consisting of
 (a) halogen,
 (b) $C_3$–$C_6$-cycloalkyl,
 (c) aryl,
 (d) substituted aryl,
 (e) heteroaryl, and
 (f) substituted heteroaryl,
(6) $C_3$–$C_6$-cycloalkyl,
(7) —CHO,
(8) —C(O)—$C_1$–$C_6$-alkyl,
(9) —C(O)—NR'R", wherein R' and R" are as previously defined, and
(10) —C(O)—O—$C_1$–$C_6$-alkyl, or $R^1$ and $R^2$ taken together may be —$(CH_2)_p$—, wherein p is 3-to-7, which taken together with the nitrogen atom to which they are attached, thus form a heterocyclic ring containing one nitrogen atom and from 3 to 7 carbon atoms;

R is selected from the group consisting of
(1) methyl substituted with a substituent selected from the group consisting of
 (a) —CN,
 (b) —F,
 (c) —CO$_2$R$^3$ wherein R$^3$ is C$_1$–C$_3$-alkyl, aryl-substituted C$_1$–C$_3$-alkyl, or heteroaryl-substituted C$_1$–C$_3$-alkyl,
 (d) —S(O)$_n$—R$^3$ wherein n is 0, 1, or 2, and R$^3$ is as previously defined,
 (e) —NH—C(O)—R$^3$ where R$^3$ is as previously defined,
 (f) —NH—C(O)—NR$^4$R$^5$ wherein R$^4$ and R$^5$ are independently selected from the group consisting of
  (i) hydrogen,
  (ii) C$_1$–C$_3$-alkyl
  (iii) C$_1$–C$_3$-alkyl substituted with aryl,
  (iv) C$_1$–C$_3$-alkyl substituted with substituted aryl,
  (v) C$_1$–C$_3$-alkyl substituted with heteroaryl, and
  (vi) C$_1$–C$_3$-alkyl substituted with and substituted heteroaryl,
 (g) aryl,
 (h) substituted aryl,
 (i) heteroaryl, and
 (j) substituted heteroaryl,
(2) C$_2$–C$_{10}$-alkyl,
(3) C$_2$–C$_{10}$-alkyl substituted with one or more substituents selected from the group consisting of
 (a) halogen,
 (b) hydroxy,
 (c) C$_1$–C$_3$-alkoxy,
 (d) C$_1$–C$_3$-alkoxy-C$_1$–C$_3$-alkoxy,
 (e) oxo,
 (f) —N$_3$,
 (g) —CHO,
 (h) —O—SO$_2$-(substituted C$_1$–C$_6$-alkyl),
 (i) —NR$^6$R$^7$ wherein R$^6$ and R$^7$ are selected from the group consisting of
  (i) hydrogen,
  (ii) C$_1$–C$_{12}$-alkyl,
  (iii) substituted C$_1$–C$_{12}$-alkyl,
  (iv) C$_1$–C$_{12}$-alkenyl,
  (v) substituted C$_1$–C$_{12}$-alkenyl,
  (vi) C$_1$–C$_{12}$-alkynyl,
  (vii) substituted C$_1$–C$_{12}$-alkynyl,
  (viii) aryl,
  (ix) C$_3$–C$_8$-cycloalkyl,
  (x) substituted C$_3$–C$_8$-cycloalkyl,
  (xi) substituted aryl,
  (xii) heterocycloalkyl,
  (xiii) substituted heterocycloalkyl,
  (xiv) C$_1$–C$_{12}$-alkyl substituted with aryl,
  (xv) C$_1$–C$_{12}$-alkyl substituted with substituted aryl,
  (xvi) C$_1$–C$_{12}$-alkyl substituted with heterocycloalkyl,
  (xvii) C$_1$–C$_{12}$-alkyl substituted with substituted heterocycloalkyl,
  (xviii) C$_1$–C$_{12}$-alkyl substituted with C$_3$–C$_8$-cycloalkyl,
  (xix) C$_1$–C$_{12}$-alkyl substituted with substituted C$_3$–C$_8$-cycloalkyl,
  (xx) heteroaryl,
  (xxi) substituted heteroaryl,
  (xxii) C$_1$–C$_{12}$-alkyl substituted with heteroaryl, and
  (xxiii) C$_1$–C$_{12}$-alkyl substituted with substituted heteroaryl, or
  R$^6$ and R$^7$ are taken together with the atom to which they are attached form a 3–10 membered heterocycloalkyl ring which may be substituted with one or more substituents independently selected from the group consisting of
   (i) halogen,
   (ii) hydroxy,
   (iii) C$_1$–C$_3$-alkoxy,
   (iv) C$_1$–C$_3$-alkoxy-C$_1$–C$_3$-alkoxy,
   (v) oxo,
   (vi) C$_1$–C$_3$-alkyl,
   (vii) halo-C$_1$–C$_3$-alkyl, and
   (vii) C$_1$–C$_3$-alkoxy-C$_1$–C$_3$-atkyl,
 (j) —CO$_2$R$^3$ wherein R$^3$ is as previously defined,
 (k) —C(O)—NR$^4$R$^5$ wherein R$^4$ and R$^5$ are as previously defined,
 (l) =N—O—R$^3$ wherein R$^3$ is as previously defined,
 (m) —C≡N,
 (n) —O—S(O)$_n$—R$^3$ wherein n and R$^3$ are as previously defined,
 (o) aryl,
 (p) substituted aryl,
 (q) heteroaryl,
 (r) substituted heteroaryl,
 (s) C$_3$–C$_8$-cycloalkyl,
 (t) substituted C$_3$–C$_8$-cycloalkyl,
 (u) C$_1$–C$_{12}$-alkyl substituted with heteroaryl,
 (v) heterocycloalkyl,
 (w) substituted heterocycloalkyl,
 (x) —NH—C(O)—R$^3$ where R$^3$ is as previously defined,
 (y) —NH—C(O)—NR$^4$R$^5$ wherein R$^4$ and R$^5$ are as previously defined,
 (z) =N—NR$^6$R$^7$ wherein R$^6$ and R$^7$ are as previously defined,
 (aa) =N—R$^3$ wherein R$^3$ is as previously defined,
 (bb) =N—NH—C(O)—R$^4$ wherein R$^4$ is as previously defined, and
 (cc) =N—NH—C(O)—NR$^4$R$^5$ wherein R$^4$ and R$^5$ are as previously defined,
(4) C$_3$-alkenyl substituted with a moiety selected from the group consisting of
 (a) halogen,
 (b) —CHO,
 (c) —CO$_2$R$^3$ where R$^3$ is as previously defined,
 (d) —C(O)—R$^4$ where R$^4$ is as previously defined,
 (e) —C(O)—NR$^4$R$^5$ wherein R$^4$ and R$^5$ are as previously defined,
 (f) —C≡N,
 (g) aryl,
 (h) substituted aryl,
 (i) heteroaryl,
 (j) substituted heteroaryl,
 (k) C$_3$–C$_7$-cycloalkyl, and
 (l) C$_1$–C$_{12}$-alkyl substituted with heteroaryl,
(5) C$_4$–C$_{10}$-alkenyl,
(6) C$_4$–C$_{10}$-alkenyl substituted with one or more substituents selected from the group consisting of
 (a) halogen,
 (b) C$_1$–C$_3$-alkoxy,
 (c) oxo,
 (d) —CHO,
 (e) —CO$_2$R$^3$ where R$^3$ is as previously defined,
 (f) —C(O)—NR$^4$R$^5$ wherein R$^4$ and R$^5$ are as previously defined, (g) —NR$^6$R$^7$ wherein R$^6$ and R$^7$ are as previously defined,
(h) =N—O—R$^3$ wherein R$^3$ is as previously defined,
(i) —C≡N,
(j) —O—S(O)$_n$—R$^3$ wherein n is 0, 1, or 2 and R$^3$ is as previously defined,
(k) aryl,
(l) substituted aryl,
(m) heteroaryl,
(n) substituted heteroaryl,
(o) C$_3$–C$_7$-cycloalkyl,
(p) C$_1$–C$_{12}$-alkyl substituted with heteroaryl,
(q) —NH—C(O)—R$^3$ where R$^3$ is as previously defined,
(r) —NH—C(O)—NR$^4$R$^5$ wherein R$^4$ and R$^5$ are as previously defined,
(s) =N—NR$^6$R$^7$ wherein R$^6$ and R$^7$ are as previously defined,
(t) =N—R$^3$ wherein R$^3$ is as previously defined,
(u) =N—NH—C(O)—R$^3$ where R$^3$ is as previously defined, and
(v) =N—NH—C(O)—NR$^4$R$^5$ wherein R$^4$ and R$^5$ are as previously defined,
(7) C$_3$–C$_{10}$-alkynyl, and
(8) C$_3$–C$_{10}$-alkynyl substituted with one or more substituents selected from the group consisting of
(a) trialkylsilyl,
(b) aryl,
(c) substituted aryl,
(d) heteroaryl, and
(e) substituted heteroaryl,
with the proviso that when R is allyl and R$^1$ is methyl, R$^2$ is not H;
R$^p$ is hydrogen or a hydroxy protecting group;
R$^w$ is selected from the group consisting of
(1) hydrogen,
(2) C$_1$–C$_6$-alkyl, optionally substituted with one or more substituents selected from the group consisting of
(a) aryl,
(b) substituted aryl,
(c) heteroaryl,
(d) substituted heteroaryl,
(3) a group selected from option (2) as previously defined further substituted with —CH$_2$—M—R$^8$, wherein M is selected from the group consisting of
(i) —O—,
(ii) —NH—,
(ii) —N(CH$_3$)—,
(iv) —S(O)$_n$—, wherein n is as described previously,
(v) —NH—C(O)—, and
(vi) —C(O)—NH—, and
R$^8$ is selected from the group consisting of
(i) —(CH$_2$)$_n$-aryl, wherein n is as described previously,
(ii) —(CH$_2$)$_n$-substituted aryl, wherein n is as described previously,
(iii) —(CH$_2$)$_n$-heteroaryl, wherein n is as described previously,
(iv) —(CH$_2$)$_n$-substituted heteroaryl, wherein n is as described previously, and
(v) —(CH$_2$)$_n$-heterocycloalkyl, wherein n is as described previously; and
W is absent or is selected from the group consisting of —O—, —NH— and —N(CH$_3$)—.

The present invention also provides pharmaceutical compositions which comprise a therapeutically effective amount of a compound as defined previously in combination with a pharmaceutically acceptable carrier.

The invention further relates to a method of treating bacterial infections in a host mammal in need of such treatment comprising administering to a mammal in need of such treatment a therapeutically effective amount of a compound as defined previously.

In a further aspect of the present invention, processes are provided for the preparation of 3'-N-modified 6-O-substituted erythromycin ketolide derivatives of Formula (I), (II), (III), (IV) and (V) as described previously.

DETAILED DESCRIPTION OF THE INVENTION

Definitions

As used throughout this specification and the appended claims, the following terms have the meanings specified.

The term "alkanoyl" as used herein refers to an C$_1$–C$_6$-alkyl group, as defined herein, attached to the parent molecular moiety through an carbonyl group. Examples of alkanoyl groups include acetyl, propanoyl, butanoyl, and the like.

The terms "C$_1$–C$_3$-alkyl", "C$_1$–C$_6$-alkyl", and "C$_1$–C$_{12}$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of C$_1$–C$_3$-alkyl radicals include methyl, ethyl, propyl and isopropyl, examples of C$_1$–C$_6$-alkyl radicals include, but are not limited to, methyl, ethyl, propyl, isopropyl, n-butyl, tert-butyl, neopentyl and n-hexyl. Examples of C$_1$–C$_{12}$-alkyl radicals include, but are not limited to, all the foregoing examples as well as n-heptyl, n-octyl, n-nonyl, n-decyl, n-undecyl and n-docecyl.

The term "C$_1$–C$_6$-alkoxy" as used herein refers to an C$_1$–C$_6$-alkyl group, as previously defined, attached to the parent molecular moiety through an oxygen atom. Examples of C$_1$–C$_6$-alkoxy, but are not limited to, methoxy, ethoxy, propoxy, iso-propoxy, n-butoxy, tert-butoxy, neo-pentoxy and n-hexoxy.

The term "C$_1$–C$_{12}$-alkenyl" denotes a monovalent group derived from a hydrocarbon moiety containing from two to twelve carbon atoms and having at least one carbon-carbon double bond by the removal of a single hydrogen atom. Alkenyl groups include, for example, ethenyl, propenyl, butenyl,1-methyl-2-buten-1-yl, and the like.

The term "C$_1$–C$_{12}$-alkynyl" as used herein refers to a monovalent group derived from a hydrocarbon containing from two to twelve carbon atoms and having at least one carbon-carbon triple bond by the removal of a single hydrogen atom. Representative alkynyl groups include ethynyl, 2-propynyl (propargyl), 1-propynyl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "C$_1$–C$_3$-alkylamino" as used herein refers to one or two C$_1$–C$_3$-alkyl groups, as previously defined, attached to the parent molecular moiety through a nitrogen atom. Examples of C$_1$–C$_3$-alkylamino include, but are not limited to methylamino, dimethylamino, ethylamino, diethylamino, and propylamino.

The term "oxo" denotes a group wherein two hydrogen atoms on a single carbon atom in an alkyl group as defined previously are replaced with a single oxygen atom (i.e. a carbonyl group).

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heteroaryl compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, New York, 1986.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, substituted loweralkyl, cycloalkyl, alkenyl, alkoxy, alkanoyl, haloalkyl, alkoxy, thioalkoxy, amino, alkylamino, dialkylamino, acylamino, cyano, hydroxy, hydroxyalkyl, halo, mercapto, nitro, carboxaldehyde, carboxy, alkoxycarbonyl, and carboxamide. In addition, substituted aryl groups include tetrafluorophenyl and pentafluorophenyl.

The term "$C_3$–$C_{12}$-cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptyl, and bicyclo[2.2.2]octyl.

The terms "halo" and "halogen" as used herein refer to an atom selected from fluorine, chlorine, bromine and iodine.

The term "alkylamino" refers to a group having the structure —NHR' wherein R' is alkyl, as previously defined, Examples of alkylamino include methylamino, ethylamino, isopropylamino and the like.

The term "dialkylamino" refers to a group having the structure —NR'R" wherein R' and R" are independently selected from alkyl, as previously defined. Additionally, R' and R" taken together may optionally be —$(CH_2)_k$— wherein k is an integer of from 2 to 6. Examples of dialkylamino include, dimethylamino, diethylaminocarbonyl, methylethylaminno, piperidino, and the like.

The term "haloalkyl" denotes an alkyl group, as defined previously, having one, two, or three halogen atoms attached thereto and is exemplified by such groups as chloromethyl, bromoethyl, trifluoromethyl, and the like, The term "alkoxycarbonyl" represents an ester group; i.e. an alkoxy group, attached to the parent molecular moiety through a carbonyl group such as methoxycarbonyl, ethoxycarbonyl, and the like.

The term "thioalkoxy" refers to an alkyl group as previously defined attached to the parent molecular moiety through a sulfur atom.

The term "carboxaldehyde" as used herein refers to a group of formula —CHO.

The term "carboxy" as used herein refers to a group of formula —$CO_2H$.

The term "carboxamide" as used herein refers to a group of formula —CONHR'R" wherein R' and R" are independently selected from hydrogen or alkyl, or R' and R" taken together may optionally be —$(CH_2)_k$— where k is an integer of from 2 to 6.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, and the like.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

Specific heterocycloalkyl rings considered useful in preparing compounds of the invention include: 3-methyl-4-(3-methylphenyl)piperazine, 3-methylpiperidine, 4-(bis-(4-fluorophenyl)methyl)piperazine, 4-(diphenylmethyl) piperazine, 4-(ethoxycarbonyl)piperazine, 4-(ethoxycarbonylmethyl)piperazine, 4-(phenylmethyl) piperazine, 4-(1-phenylethyl)piperazine, 4-(1,1-dimethylethoxycarbonyl)piperazine, 4-(2-(bis-(2-propenyl) amino)ethyl)piperazine, 4-(2-(diethylamino)ethyl) piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl) piperazine, 4-(2-methoxyphenyl)piperazine, 4-(2-methylphenyl)piperazine, 4-(2-methylthiophenyl) piperazine, 4-(2-nitrophenyl)piperazine, 4-(2-nitrophenyl) piperazine, 4-(2-phenylethyl)piperazine, 4-(2-pyridyl) piperazine, 4-(2-pyrimidinyl)piperazine, 4-(2,3-dimethylphenyl)piperazine, 4-(2,4-difluorophenyl) piperazine, 4-(2,4-dimethoxyphenyl)piperazine, 4-(2,4-dimethylphenyl)piperazine, 4-(2,5-dimethylphenyl) piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-(3,4-dimethoxyphenyl) piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl) piperazine, 4-(3,5-dimethoxyphenyl)piperazine, 4-(4-(phenylmethoxy)phenyl)piperazine, 4(4-(1,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl) piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl) piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-((2-furanyl)carbonyl)piperazine, 4-((1,3-dioxolan-5-yl)methyl)piperazine, 6-fluoro-1,2,3,4-tetrahydro-2-methylquinoline, 1,4-diazacycloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term "heteroarylalkyl" as used herein, refers to a heteroaryl group as defined previously attached to the parent molecular moiety through an alkylene group wherein the alkylene group is of one to four carbon atoms.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, ethers such as methoxymethyl, and esters including acetyl benzoyl, and the like.

The term "ketone protecting group", as used herein, refers to an easily removable group which is known in the art to protect a ketone group against undesirable reactions during synthetic procedures and to be selectively removable. The use of ketone-protecting groups is well known in the art for protecting groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991). Examples of ketone-protecting groups include, but are not limited to, ketals, oximes, O-substituted oximes for example O-benzyl oxime, O-phenylthiomethyl oxime, 1-isopropoxycyclohexyl oxime, and the like.

A the term "protected-hydroxy" refers to a hydroxy group protected with a hydroxy protecting group, as defined previously, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, New York, 1986.

The term "substituted aryl" as used herein refers to an aryl group as defined herein substituted by independent replacement of one, two or three of the hydrogen atoms thereon with —Cl, —Br, —F, —I, —OH, —CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, cycloalkyl, alkenyl, alkoxy, alkanoyl, hydroxyalkyl, alkoxycarbonyl and carboxamide. In addition, any one substitutent may be an aryl, heteroaryl, or heterocycloalkyl group. Also, substituted aryl groups include tetrafluorophenyl and pentafluorophenyl.

The term "substituted heteroaryl" as used herein refers to a heteroaryl group as defined herein substituted by independent replacement of one, two or three of the hydrogen atoms thereon with —Cl, —Br, —F, —I, —OH, —CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl, and carboxamide. In addition, any one substitutent may be an aryl, heteroaryl, or heterocycloalkyl group.

The term "substituted heterocycloalkyl" as used herein, refers to a heterocycloalkyl group, as defined previously, substituted by independent replacement of one, two or three of the hydrogen atoms thereon with —Cl, —Br, —F, —I, —OH, —CN, —$C_1$–$C_3$-alkyl, $C_1$–$C_6$-alkoxy, $C_1$–$C_6$-alkoxy substituted with aryl, haloalkyl, thioalkoxy, arnino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the previously formula, for example by hydrolysis in blood. A thorough discussion is provided in T. Higuchi and V. Stella, *Pro-drugs as Novel Delivery Systems*, Vol. 14 of the A. C. S. Symposium Series, and in Edward B. Roche, ed., *Bioreversible Carriers in Drug Design*, American Pharmaceutical Association and Pergamon Press, 1987, both of which are incorporated herein by reference.

Preferred Embodiments

In a first embodiment of the invention is a compound having the formula (I) as described previously. Compounds of formula (I) also have utility as intermediates in the preparation of compounds of formula (II)–(V) of the invention.

In a second embodiment of the invention is a compound having the formula (II) as described previously.

In a third embodiment of the invention is a compound having the formula (III) as described previously.

In a fourth embodiment of the invention is a compound having the formula (IV) as described previously.

In a fifth embodiment of the invention is a compound having the formula (V) as described previously.

Representative compounds of the invention are those selected from the group consisting of Compound of Formula (I), R is —$CH_2CH=CH$-(3-quinolyl), $R^p$ is H, $R^1$ is methyl, $R^2$ is hydrogen;

Compound of formula (II), R is —$CH_2CH=CH$-(3-quinolyl), $R^p$ is acetyl, $R^1$ is H, $R^2$ is $CH_3$, W is absent, $R^w$ is H;

Compound of Formula (II); R is —$CH_2CH=CH$-(3-quinolyl), $R^p$ is H, W is absent, $R^w$ is H, $R^1$ is H, $R^2$ is $CH_3$;

Compound of Formula (II); R is —$CH_2CH=CH$-(3-quinolyl), $R^p$ is H, W is absent, $R^w$ is H, $R^1$ is acetyl, $R^2$ is $CH_3$;

Compound of Formula (II); R is —$CH_2CH=CH$-(3-quinolyl), $R^p$ is H, W is absent, $R^w$ is H, $R^1$ is $CH_2C(O)$—O—$CH_2CH_3$, $R^2$ is $CH_3$;

Compound of Formula (II); R is —$CH_2CH=CH$-(3-quinolyl), $R^p$ is H, W is absent, $R^w$ is H, $R^1$ is $CH_2CH=CH_2$, $R^2$ is $CH_3$;

Compound of Formula (II); R is —$CH_2CH=CH$-(3-quinolyl), $R^p$ is H, W is absent, $R^w$ is H, $R^1$ is $CH_2CH_2F$, $R^2$ is $CH_3$;

Compound of Formula (II); R is —$CH_2CH=CH$-(3-quinolyl), $R^p$ is H, W is absent, $R^w$ is H, $R^1$ is $CH_2$-phenyl, $R^2$ is $CH_3$;

Compound of Formula (II); R is —$CH_2CH=CH$-(3-quinolyl), $R^p$ is H, W is absent, $R^w$ is H, $R^1$ is $CH_2$-CN, $R^2$ is $CH_3$;

Compound of Formula (II); R is —$CH_2CH=CH$-(3-quinolyl), $R^p$ is H, W is absent, $R^w$ is H, $R^1$ is $CH_2$—$C\equiv CH$, $R^2$ is $CH_3$;

Compound of Formula (II); R is —$CH_2CH=CH$-(3-quinolyl), $R^p$ is H, W is absent, $R^w$ is H, $R^1$ is $CH_2CH_2CH_3$, $R^2$ is $CH_3$;

Compound of Formula (II); R is —$CH_2CH=CH$-(3-quinolyl), $R^p$ is H, W is absent, $R^w$ is H, $R^1$ is $CH_2$-cyclopropyl, $R^2$ is $CH_3$;

Compound of Formula (II); R is —$CH_2CH=CH$-(3-quinolyl), $R^p$ is H, W is absent, $R^w$ is H, $R^1$ is cyclopropyl, $R^2$ is $CH_3$;

Compound of Formula (II); R is —$CH_2CH=CH$-(3-quinolyl), $R^p$ is H, W is absent, $R^w$ is H, $R^1$ is $CH_2$-(3-pyridyl), $R^2$ is $CH_3$;

Compound of Formula (II); R is —$CH_2CH=CH$-(3-quinolyl), $R^p$ is H, W is absent, $R^w$ is H, $R^1$ is $CH_2$-(cyclo-$C_3H_5$), $R^2$ is $CH_3$;

Compound of Formula (II); R is —$CH_2CH=CH$-(3-quinolyl), $R^p$ is H, W is absent, $R^w$ is H, $R^1$ is $CH_2CH_2CH_3$, $R^2$ is $CH_3$;

Compound of Formula (II); R is —$CH_2CH=CH$-(3-quinolyl), $R^p$ is H, W is absent, $R^w$ is H, $R^1$ is $CH_2CH=CHC_6H_5$, $R^2$ is $CH_3$;

Compound of Formula (II); R is —$CH_2CH=CH$-(3-quinolyl), $R^p$ is H, W is absent, $R^w$ is H, $R^1$ is $CH_2C(=CH_2)C(O)OCH_3$, $R^2$ is $CH_3$;

Compound of Formula (II); R is —$CH_2CH=CH$-(3-quinolyl), $R^p$ is H, W is absent, $R^w$ is H, $R^1$ is $CH_2C(=CH_2)CH_3$, $R^2$ is $CH_3$;

Compound of Formula (II); R is —$CH_2CH=CH$-(3-quinolyl), $R^p$ is H, W is absent, $R^w$ is H, $R^1$ is cyclo-$C_3H_5$, $R^2$ is $CH_3$;

Compound of Formula (II); R is —$CH_2CH=CH$-(3-quinolyl), $R^p$ is H, W is absent, $R^w$ is H, $R^1$ is $CH_2$-(3-pyridyl), $R^2$ is $CH_3$;

Compound of Formula (II); R is —$CH_2CH=CH$-(3-quinolyl), $R^p$ is H, W is absent, $R^w$ is H, $R^1$ is $CH_2$-(3-hydroxyphenyl), $R^2$ is $CH_3$;

Compound of Formula (II); R is —$CH_2CH=CH$-(3-quinolyl), $R^p$ is H, W is absent, $R^w$ is H, $R^1$ is $CH_2$-(2-hydroxy-3-tert-butyl-5-methylphenyl), $R^2$ is $CH_3$;

Compound of Formula (II); R is —$CH_2CH=CH$-(3-quinolyl), $R^p$ is H, W is absent, $R^w$ is H, $R^1$ is $CH_2$-(2-hydroxy-3,4-dimethylphenyl), $R^2$ is $CH_3$;

Compound of Formula (II); R is —$CH_2CH=CH$-(3-quinolyl), $R^p$ is H, W is absent, $R^w$ is H, $R^1$ is $CH_2$-(2-hydroxy-3-methoxy-5-(2-propenyl)phenyl), $R^2$ is $CH_3$;

Compound of Formula (II); R is —$CH_2CH=CH$-(3-quinolyl), $R^p$ is H, W is absent, $R^w$ is H, $R^1$ is $CH_2$-(2-hydroxy-3-methoxy-5-methylphenyl), $R^2$ is $CH_3$;

Compound of Formula (II); R is —$CH_2CH=CH$-(3-quinolyl), $R^p$ is H, W is absent, $R^w$ is H, $R^1$ is $CH_2$-(2-hydroxy-5-cyclopentylphenyl), $R^2$ is $CH_3$;

Compound of Formula (II); R is —CH$_2$CH═CH-(3-quinolyl), R$^p$ is H, W is absent, R$^w$ is H, R$^1$ is CH$_2$-(2-hydroxy-5-carboxan-idophenyl), R$^2$ is CH$_3$;

Compound of Formula (II); R is —CH$_2$CH═CH-(3-quinolyl), R$^p$ is H, W is absent, R$^w$ is H, R$^1$ is CH$_2$-(2-hydroxy-3-methoxy-5-(2-methoxycarbonylethyl)phenyl), R$^2$ is CH$_3$;

Compound of Formula (II); R is —CH$_2$CH═CH-(3-quinolyl), R$^p$ is H, W is absent, R$^w$ is H, R$^1$ is CH$_2$-(2-hydroxy-3-methyl-5-fluorophenyl), R$^2$ is CH$_3$;

Compound of Formula (II); R is —CH$_2$CH═CH-(3-quinolyl), R$^p$ is H, W is absent, R$^w$ is H, R$^1$ is CH$_2$-(2-hydroxy-3-methoxy-5-acetylphenyl), R$^2$ is CH$_3$;

Compound of Formula (II); R is —CH$_2$CH═CH-(3-quinolyl), R$^p$ is H, W is absent, R$^w$ is H, R$^1$ is CH$_2$-(2-hydroxy-3-bromophenyl), R$^2$ is CH$_3$;

Compound of Formula (II); R is —CH$_2$CH═CH-(3-quinolyl), R$^p$ is H, W is absent, R$^w$ is H, R$^1$ is CH$_2$-(2-hydroxy-3-methoxy-5-alkoxycarbonylphenyl), R$^2$ is CH$_3$;

Compound of Formula (II); R is —CH$_2$CH═CH-(3-quinolyl), R$^p$ is H, W is absent, R$^w$ is H, R$^1$ is CH$_2$-(2-hydroxy-3-ethylphenyl), R$^2$ is CH$_3$;

Compound of Formula (II); R is —CH$_2$CH═CH-(3-quinolyl), R$^p$ is H, W is absent, R$^w$ is H, R$^1$ is CH$_2$-(2-hydroxy-5-isobutylphenyl), R$^2$ is CH$_3$;

Compound of Formula (II); R is —CH$_2$CH═CH-(3-quinolyl), R$^p$ is H, W is absent, R$^w$ is H, R$^1$ is CH$_2$-(2-hydroxy-3-methyl-5-diethylamino-6-methylphenyl), R$^2$ is CH$_3$;

Compound of Formula (II); R is —CH$_2$CH═CH-(3-quinolyl), R$^p$ is H, W is absent, R$^w$ is H, R$^1$ is CH$_2$-(2-hydroxy-4-methyl-5-bromo-6-methylphenyl), R$^2$ is CH$_3$; and Compound of Formula (II); R is —CH$_2$CH═CH-(3-quinolyl), R$^p$ is H, W is absent, R$^w$ is H, R$^1$ is CH$_2$-(2-hydroxy-3-hydroxymethylphenyl), R$^2$ is CH$_3$.

Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 2 demonstrate the antibacterial activity of the compounds of the invention.

TABLE 1

Antibacterial Activity (MIC's) of Selected Compounds

| Microorganism | Organism code | Ery. A | Example 2 | Example 3 | Example 4 | Example 5 | Example 6 |
|---|---|---|---|---|---|---|---|
| Staphylococcus aureus ATCC 6538P | AA | 0.2 | 0.2 | 0.2 | 6.2 | 6.2 | 0.05 |
| Staphylococcus aureus A5177 | BB | 3.1 | 0.2 | 0.2 | 6.2 | 12.5 | 0.05 |
| Staphylococcus aureus A-5278 | CC | >100 | >100 | >100 | >100 | >100 | >100 |
| Staphylococcus aureus CMX 642A | DD | 0.39 | 0.2 | 0.39 | 6.2 | 12.5 | 0.1 |
| Staphylococcus aureus NCTC10649M | EE | 0.39 | 0.2 | 0.39 | 6.2 | 12.5 | 0.05 |
| Staphylococcus aureus CMX 553 | FF | 0.39 | 0.2 | 0.39 | 6.2 | 12.5 | 0.05 |
| Staphylococcus aureus 1775 | GG | >100 | >100 | >100 | >100 | >100 | >100 |
| Staphylococcus epidermidis 3519 | HH | 0.39 | 0.2 | 0.39 | 6.2 | 12.5 | 0.2 |
| Enterococcus faecium ATCC 8043 | II | 0.05 | 0.05 | 0.2 | 1.56 | 6.2 | 0.05 |
| Streptococcus bovis A-5169 | JJ | 0.02 | <=0.005 | 0.01 | 0.2 | 1.56 | 0.02 |
| Streptococcus agalactiae CMX 508 | KK | 0.05 | <=0.005 | 0.02 | 0.39 | 1.56 | 0.05 |
| Streptococcus pyogenes EES61 | LL | 0.05 | <=0.005 | 0.01 | 0.39 | 0.39 | 0.02 |
| Streptococcus pyogenes 930 | MM | >100 | 25 | 12.5 | — | >100 | 3.1 |
| Streptococcus pyogenes PIU 2548 | NN | 6.2 | 0.39 | 0.39 | 1.56 | 6.2 | 0.2 |
| Micrococcus luteus ATCC 9341 | OO | 0.05 | 0.02 | 0.02 | 0.39 | 0.78 | 0.02 |
| Micrococcus luteus ATCC 4698 | PP | 0.2 | 0.1 | 0.1 | 3.1 | 6.2 | 0.2 |
| Escherichia coli JUHL | QQ | >100 | >100 | >100 | >100 | >100 | 50 |
| Escherichia coli SS | RR | 0.78 | 0.39 | 0.78 | 100 | 25 | 0.2 |
| Escherichia coli DC-2 | SS | >100 | >100 | >100 | >100 | >100 | 100 |
| Candida albicans CCH 442 | TT | >100 | >100 | >100 | >100 | >100 | >100 |
| Mycobacterium smegmatis ATCC 114 | UU | 3.1 | 3.1 | 12.5 | 25 | 25 | 0.2 |
| Nocardia Asteroides ATCC9970 | VV | 0.1 | 1.56 | 3.1 | 12.5 | 25 | 0.1 |
| Haemophilis Influenzae DILL AMP R | WW | 4 | 16 | 16 | >128 | 128 | 4 |
| Streptococcus Pheumoniae ATCC6303 | XX | 0.06 | 0.03 | 0.03 | 0.25 | 0.25 | <=0.004 |
| Streptococcus Pheumoniae GYR 1171 | YY | 0.06 | 0.03 | 0.03 | 0.125 | 0.25 | <=0.004 |
| Streptococcus Pheumoniae 5979 | ZZ | >128 | 128 | >128 | 128 | >128 | 16 |
| Streptococcus Pheumoniae 5649 | ZZA | 16 | 0.5 | 0.5 | 0.25 | 2 | 0.25 |

| Microorganism | Organism code | Example 7 | Example 8 | Example 9 | Example 10 | Example 13 | Example 14 | Example 15 |
|---|---|---|---|---|---|---|---|---|
| Staphylococcus aureus ATCC 6538P | AA | 0.1 | 0.2 | 0.1 | 0.2 | 1.56 | 0.39 | 0.39 |
| Staphylococcus aureus A5177 | BB | 0.2 | 0.2 | 0.1 | 0.39 | 3.1 | 0.39 | 0.39 |

TABLE 1-continued

Antibacterial Activity (MIC's) of Selected Compounds

| Microorganism | | | | | | | | |
|---|---|---|---|---|---|---|---|---|
| Staphylococcus aureus A-5278 | CC | >100 | >100 | >100 | >100 | >100 | >100 | >100 |
| Staphylococcus aureus CMX 642A | DD | 0.1 | 0.2 | 0.1 | 0.2 | 1.56 | 0.39 | 0.39 |
| Staphylococcus aureus NCTC10649M | EE | 0.1 | 0.2 | 0.1 | 0.1 | 3.1 | 0.39 | 0.39 |
| Staphylococcus aureus CMX 553 | FF | 0.05 | 0.2 | 0.05 | 0.2 | 1.56 | 0.39 | 0.39 |
| Staphylococcus aureus 1775 | GG | >100 | >100 | >100 | >100 | >100 | >100 | >100 |
| Staphylococcus epidermidis 3519 | HH | 0.2 | 0.2 | 0.2 | 0.2 | 3.1 | 0.39 | 0.39 |
| Enterococcus faecium ATCC 8043 | II | 0.05 | 0.1 | 0.1 | 0.05 | 0.39 | 0.05 | 0.05 |
| Streptococcus bovis A-5169 | JJ | 0.01 | 0.02 | 0.01 | 0.02 | 0.2 | 0.05 | 0.02 |
| Streptococcus agalactiae CMX 508 | KK | 0.05 | 0.02 | 0.01 | 0.01 | 0.2 | 0.2 | 0.05 |
| Streptococcus pyogenes EES61 | LL | 0.01 | 0.02 | 0.01 | 0.01 | 0.1 | 0.05 | 0.02 |
| Streptococcus pyogenes 930 | MM | 12.5 | >100 | 12.5 | 6.2 | >100 | 50 | 25 |
| Streptococcus pyogenes PIU 2548 | NN | 0.39 | 0.2 | 0.39 | 0.39 | 0.39 | 0.39 | 0.1 |
| Micrococcus luteus ATCC 9341 | OO | 0.05 | 0.05 | 0.02 | 0.1 | 0.39 | 0.05 | 0.05 |
| Micrococcus luteus ATCC 4698 | PP | 0.39 | 0.05 | 0.2 | 0.39 | 0.78 | 0.39 | 0.39 |
| Escherichia coli JUHL | QQ | >100 | >100 | >100 | >100 | >100 | >100 | >100 |
| Escherichia coli SS | RR | 0.39 | 0.78 | 0.2 | 1.56 | 3.1 | 0.78 | 0.2 |
| Escherichia coli DC-2 | SS | >100 | >100 | >100 | >100 | >100 | >100 | >100 |
| Candida albicans CCH 442 | TT | >100 | >100 | >100 | >100 | 50 | >100 | >100 |
| Mycobacterium smegmatis ATCC 114 | UU | 1.56 | 0.39 | 12.5 | 1.56 | 3.1 | 0.39 | 0.78 |
| Nocardia Asteroides ATCC9970 | VV | 0.39 | 0.2 | 0.78 | 0.2 | 3.1 | 0.2 | 0.2 |
| Haemophilis Influenzae DILL AMP R | WW | 8 | 4 | 8 | | | | 8 |
| Streptococcus Pheumoniae ATCC6303 | XX | 0.03 | 0.03 | 0.03 | 0.03 | 0.03 | 0.03 | 0.03 |
| Streptococcus Pheumoniae GYR 1171 | YY | 0.03 | 0.03 | 0.03 | 0.03 | 0.03 | 0.03 | 0.03 |
| Streptococcus Pheumoniae 5979 | ZZ | 16 | >128 | 128 | 32 | 16 | >128 | >128 |
| Streptococcus Pheumoniae 5649 | ZZA | 0.25 | 0.5 | 0.5 | 0.25 | 0.25 | 0.25 | 0.25 |

| Microorganism | Organism code | Example 16 | Example 17 | Example 18 | Example 19 | Example 20 | Example 21 | Example 22 |
|---|---|---|---|---|---|---|---|---|
| Staphylococcus aureus ATCC 6538P | AA | 0.39 | 0.39 | 0.39 | 0.2 | 1.56 | 0.39 | 0.2 |
| Staphylococcus aureus A5177 | BB | 0.39 | 0.39 | 0.39 | 0.2 | 3.1 | 0.39 | 0.39 |
| Staphylococcus aureus A-5278 | CC | >100 | >100 | >100 | >100 | >100 | >100 | >100 |
| Staphylococcus aureus CMX 642A | DD | 0.39 | 0.39 | 0.39 | 0.2 | 1.56 | 0.39 | 0.39 |
| Staphylococcus aureus NCTC10649M | EE | 0.39 | 0.78 | 0.39 | 0.39 | 3.1 | 0.39 | 0.39 |
| Staphylococcus aureus CMX 553 | FF | 0.39 | 0.39 | 0.39 | 0.2 | 1.56 | 0.39 | 0.39 |
| Staphylococcus aureus 1775 | GG | >100 | >100 | >100 | >100 | >100 | >100 | >100 |
| Staphylococcus epidermidis 3519 | HH | 0.39 | 0.39 | 0.39 | 0.2 | 3.1 | 0.39 | 0.39 |
| Enterococcus faecium ATCC 8043 | II | 0.05 | 0.1 | 0.1 | 0.1 | 0.39 | 0.05 | 0.1 |
| Streptococcus bovis A-5169 | JJ | 0.01 | 0.05 | 0.02 | 0.02 | 0.2 | 0.05 | 0.1 |
| Streptococcus agalactiae CMX 508 | KK | 0.01 | 0.05 | 0.02 | 0.02 | 0.2 | 0.2 | 0.1 |
| Streptococcus pyogenes EES61 | LL | 0.01 | 0.2 | 0.05 | 0.01 | 0.1 | 0.05 | 0.1 |
| Streptococcus pyogenes 930 | MM | 12.5 | 12.5 | 25 | 6.2 | >100 | 50 | 3.1 |
| Streptococcus pyogenes PIU 2548 | NN | 0.1 | 0.39 | 0.39 | 0.2 | 0.39 | 0.39 | 0.1 |
| Micrococcus luteus ATCC 9341 | OO | 0.02 | 0.05 | 0.02 | 0.05 | 0.39 | 0.05 | 0.1 |
| Micrococcus luteus ATCC 4698 | PP | 0.39 | 0.39 | 0.39 | 0.1 | 0.78 | 0.39 | 0.1 |
| Escherichia coli JUHL | QQ | >100 | >100 | >100 | >100 | >100 | >100 | >100 |
| Escherichia coli SS | RR | 0.2 | 1.56 | 0.78 | 0.78 | 3.1 | 0.78 | 0.39 |
| Escherichia coli DC-2 | SS | >100 | >100 | >100 | >100 | >100 | >100 | >100 |
| Candida albicans CCH 442 | TT | >100 | >100 | >100 | >100 | >100 | >100 | >100 |
| Mycobacterium smegmatis ATCC 114 | UU | 1.56 | 0.39 | 6.2 | 0.2 | 3.1 | 0.39 | 0.78 |
| Nocardia Asteroides ATCC9970 | VV | 0.1 | 0.2 | 0.2 | 0.1 | 3.1 | 0.2 | 0.2 |
| Haemophilis Influenzae DILL AMP R | WW | 8 | 8 | 16 | 4 | 64 | 4 | 4 |
| Streptococcus Pheumoniae ATCC6303 | XX | 0.03 | <=0.015 | <=0.004 | <=0.004 | 0.03 | 0.03 | 0.03 |
| Streptococcus Pheumoniae GYR 1171 | YY | 0.03 | <=0.015 | <=0.004 | <=0.004 | 0.03 | 0.03 | 0.03 |
| Streptococcus Pheumoniae 5979 | ZZ | 128 | 16 | 128 | 128 | 16 | >128 | — |
| Streptococcus Pheumoniae 5649 | ZZA | 0.5 | 0.25 | 0.5 | 0.12 | 0.25 | 0.25 | 0.25 |

*missing data is indicated by "—"

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium.

For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, degrees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted previously. The solid dosage forms of tablets, degrees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

In another aspect, the present invention is a process for preparing a compound selected from the group consisting of

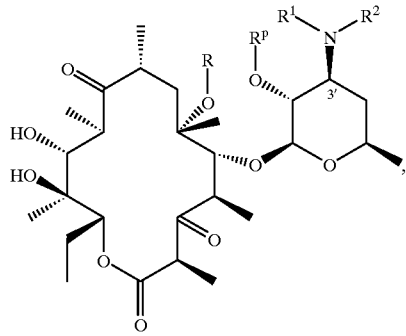
(I)

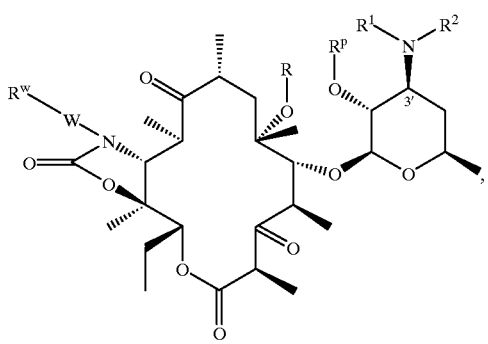
(II)

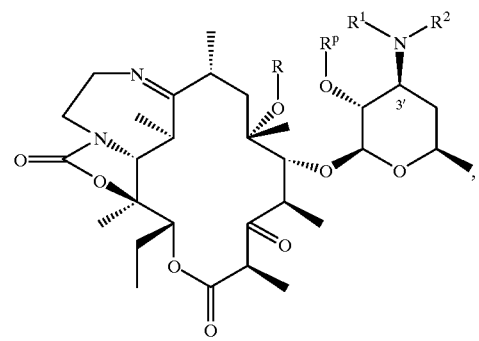
(III)

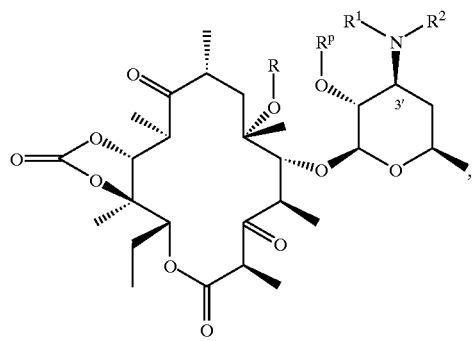
(IV)

and

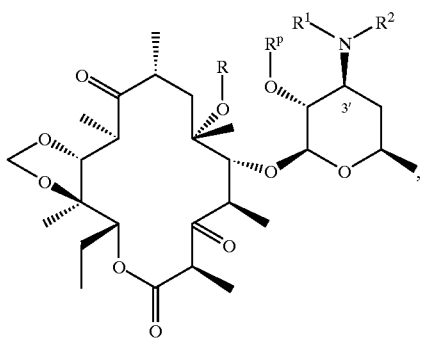
(V)

wherein
$R^1$ and $R^2$, with the proviso that $R^1$ and $R^2$ are not both methyl, are independently selected from the group consisting of
(1) hydrogen,
(2) $C_1$–$C_6$-alkyl optionally substituted with a substituent selected from the group consisting of (a) halogen,
(b) $C_3$–$C_6$-cycloalkyl,
(c) aryl,
(d) substituted aryl,
(e) heteroaryl,
(f) substituted heteroaryl,
(g) —CHO,
(h) —C(O)—$C_1$–$C_6$-alkyl, and
(i) —C(O)—NR'R", wherein R' and R" are independently selected from the group consisting of hydrogen, $C_1$–$C_3$-alkyl, $C_1$–$C_3$-alkyl substituted with aryl, substituted aryl, heteroaryl, and substituted heteroaryl, (3) $C_2$–$C_6$-alkyl optionally substituted with a substituent selected from the group consisting of
(a) $C_1$–$C_6$-alkoxy,
(b) —NR'R", wherein R' and R" are as previously defined,
(c) —NH—C(O)—$C_1$–$C_6$-alkyl,
(d) —NH—C(O)—O—$C_1$–$C_6$-alkyl,
(e) —O—C(O)—O—$C_1$–$C_6$-alkyl,
(f) —O—C(O)—$C_1$–$C_6$-alkyl,
(g) —CH(=N—O—$C_1$–$C_6$-alkyl),
(h) —C(=N—O—$C_1$–$C_6$-alkyl)—$C_1$–$C_6$-alkyl,
(i) —CH(=N—NH—$C_1$–$C_6$-alkyl), and
(j) —C(=N—NH—$C_1$–$C_6$-alkyl)—$C_1$–$C_6$-alkyl, (4) $C_3$–$C_6$-alkenyl optionally substituted with a substituent selected from the group consisting of
(a) halogen,
(b) $C_3$–$C_6$-cycloalkyl,
(c) aryl,
(d) substituted aryl,
(e) heteroaryl,
(f) substituted heteroaryl,
(g) —NH—C(O)—$C_1$–$C_6$-alkyl,
(h) —NH—C(O)—O—$C_1$–$C_6$-alkyl,
(i) —O—C(O)—O—$C_1$–$C_6$-alkyl,
(j) —O—C(O)—$C_1$–$C_6$-alkyl,
(k) —CHO,
(l) —C(O)—$C_1$–$C_6$-alkyl,
(m) —C(O)—NR'R", wherein R' and R" are as previously defined,
(n) —CH(=N—O—$C_1$–$C_6$-alkyl),
(o) —C(=N—O—$C_1$–$C_6$-alkyl)—$C_1$–$C_6$-alkyl,
(p) —CH(=N—NH—$C_1$–$C_6$-alkyl),
(q) —C(=N—NH—$C_1$–$C_6$-alkyl)—$C_1$–$C_6$-alkyl, and
(r) —C(O)—O—$C_1$–$C_6$-alkyl, (5) $C_3$–$C_6$-alkynyl optionally substituted with a substituent selected from the group consisting of
(a) halogen,
(b) $C_3$–$C_6$-cycloalkyl,
(c) aryl,
(d) substituted aryl,
(e) heteroaryl, and
(f) substituted heteroaryl, (6) $C_3$–$C_6$-cycloalkyl,
(7) —CHO,
(8) —C(O)—$C_1$–$C_6$-alkyl,
(9) —C(O)—NR'R", wherein R' and R" are previously defined, and
(10) —C(O)—O—$C_1$–$C_6$-alkyl, or $R^1$ and $R^2$ taken together may be —$(CH_2)_p$—, wherein p is 3-to-7, which taken together with the nitrogen atom to which they are attached, thus form a heterocyclic ring containing one nitrogen atom and from 3 to 7 carbon atoms;

R is selected from the group consisting of
(1) methyl substituted with a substituent selected from the group consisting of
(a) —CN,
(b) —F,
(c) —$CO_2R^3$ wherein $R^3$ is $C_1$–$C_3$-alkyl, aryl-substituted $C_1$–$C_3$-alkyl, or heteroaryl-substituted $C_1$–$C_3$-alkyl,
(d) —S(O)$_n$—$R^3$ wherein n is 0, 1, or 2, and $R^3$ is as previously defined,
(e) —NH—C(O)—$R^3$ where $R^3$ is as previously defined,
(f) —NH—C(O)—$NR^4R^5$ wherein $R^4$ and $R^5$ are independently selected from the group consisting of
(i) hydrogen,
(ii) $C_1$–$C_3$-alkyl
(iii) $C_1$–$C_3$-alkyl substituted with aryl,
(iv) $C_1$–$C_3$-alkyl substituted with substituted aryl,
(v) $C_1$–$C_3$-alkyl substituted with heteroaryl, and
(vi) $C_1$–$C_3$-atkyl substituted with and substituted heteroaryl,
(g) aryl,
(h) substituted aryl,
(i) heteroaryl, and
(j) substituted heteroaryl, (2) $C_2$–$C_{10}$-alkyl,
(3) $C_2$–$C_{10}$-alkyl substituted with one or more substituents selected from the group consisting of
(a) halogen,
(b) hydroxy,
(c) $C_1$–$C_3$-alkoxy,
(d) $C_1$–$C_3$-alkoxy-$C_1$–$C_3$-alkoxy,
(e) oxo,
(f) —$N_3$,
(g) —CHO,
(h) —O—$SO_2$-(substituted $C_1$–$C_6$-alkyl),
(i) —$NR^6R^7$ wherein $R^6$ and $R^7$ are selected from the group consisting of
(i) hydrogen,
(ii) $C_1$–$C_{12}$-atkyl,
(iii) substituted $C_1$–$C_{12}$-alkyl,
(iv) $C_1$–$C_{12}$-alkenyl,
(v) substituted $C_1$–$C_{12}$-alkenyl,
(vi) $C_1$–$C_{12}$-alkynyl,
(vii) substituted $C_1$–$C_{12}$-alkynyl,
(viii) aryl,
(ix) $C_3$–$C_8$-cycloalkyl,
(x) substituted $C_3$–$C_8$-cycloalkyl,
(xi) substituted aryl,
(xii) heterocycloalkyl,
(xiii) substituted heterocycloalkyl,
(xiv) $C_1$–$C_{12}$-atkyl substituted with aryl,
(xv) $C_1$–$C_{12}$-alkyl substituted with substituted aryl,
(xvi) $C_1$–$C_{12}$-alkyl substituted with heterocycloalkyl,
(xvii) $C_1$–$Ci_2$-alkyl substituted with substituted heterocycloalkyl,
(xviii) $C_1$–$C_{12}$-atkyl substituted with $C_3$–$C_8$-cycloalkyl,
(xix) $C_1$–$C_{12}$-alkyl substituted with substituted $C_3$–$C_8$-cycloalkyl,
(xx) heteroaryl,
(xxi) substituted heteroaryl,
(xxii) $C_1$–$C_{12}$-alkyl substituted with heteroaryl, and (xxiii) $C_1$–$C_{12}$-alkyl substituted with substituted heteroaryl, or $R^6$ and $R^7$ are taken together with the atom to which they are attached form a 3–10 membered heterocycloalkyl ring which may be substituted with one or more substituents independently selected from the group consisting of
(i) halogen,
(ii) hydroxy,
(iii) $C_1$–$C_3$-alkoxy,
(iv) $C_1$–$C_3$-alkoxy-$C_1$–$C_3$-alkoxy,
(v) oxo,
(vi) $C_1$–$C_3$-alkyl,
(vii) halo-$C_1$–$C_3$-alkyl, and
(vii) $C_1$–$C_3$-alkoxy-$C_1$–$C_3$-alkyl,
(j) —$CO_2R^3$ wherein $R^3$ is as previously defined,
(k) —C(O)—$NR^4R^5$ wherein $R^4$ and $R^5$ are as previously defined,
(l) =N—O—$R^3$ wherein $R^3$ is as previously defined,
(m) —C≡N,
(n) —O—$S(O)_n$—$R^3$ wherein n and $R^3$ are as previously defined,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl,
(u) $C_1$–$C_{12}$-alkyl substituted with heteroaryl,
(v) heterocycloalkyl,
(w) substituted heterocycloalkyl,
(x) —NH—C(O)—$R^3$ where $R^3$ is as previously defined,
(y) —NH—C(O)—$NR^4R^5$ wherein $R^4$ and $R^5$ are as previously defined,
(z) =N—$NR^6R^7$ wherein $R^6$ and $R^7$ are as previously defined,
(aa) =N—$R^3$ wherein $R^3$ is as previously defined,
(bb) =N—NH—C(O)—$R^4$ wherein $R^4$ is as previously defined, and
(cc) =N—NH—C(O)—$NR^4R^5$ wherein $R^4$ and $R^5$ are as previously defined,
(4) $C_3$-alkenyl substituted with a moiety selected from the group consisting of
(a) halogen,
(b) —CHO,
(c) —$CO_2R^3$ where $R^3$ is as previously defined,
(d) —C(O)—$R^4$ where $R^4$ is as previously defined,
(e) —C(O)—$NR^4R^5$ wherein $R^4$ and $R^5$ are as previously defined,
(f) —C≡N,
(g) aryl,
(h) substituted aryl,
(i) heteroaryl,
(j) substituted heteroaryl,
(k) $C_3$–$C_7$-cycloalkyl, and
(l) $C_1$–$C_{12}$-alkyl substituted with heteroaryl,
(5) $C_4$–$C_{10}$-alkenyl,
(6) $C_4$–$C_{10}$-alkenyl substituted with one or more substituents selected from the group consisting of
(a) halogen,
(b) $C_1$–$C_3$-alkoxy,
(c) oxo,
(d) —CHO,
(e) —$CO_2R^3$ where $R^3$ is as previously defined,
(f) —C(O)—$NR^4R^5$ wherein $R^4$ and $R^5$ are as previously defined,
(g) —$NR^6R^7$ wherein $R^6$ and $R^7$ are as previously defined,
(h) =N—O—$R^3$ wherein $R^3$ is as previously defined,
(i) —C≡N,
(j) —O—$S(O)_n$—$R^3$ wherein n is 0, 1, or 2 and $R^3$ is as previously defined,
(k) aryl,
(l) substituted aryl,
(m) heteroaryl,
(n) substituted heteroaryl,
(o) $C_3$–$C_7$-cycloalkyl,
(p) $C_1$–$C_{12}$-alkyl substituted with heteroaryl,
(q) —NH—C(O)—$R^3$ where $R^3$ is as previously defined,
(r) —NH—C(O)—$NR^4R^5$ wherein $R^4$ and $R^5$ are as previously defined,
(s) =N—$NR^6R^7$ wherein $R^6$ and $R^7$ are as previously defined,
(t) =N—$R^3$ wherein $R^3$ is as previously defined,
(u) =N—NH—C(O)—$R^3$ where $R^3$ is as previously defined, and
(v) =N—NH—C(O)—$NR^4R^5$ wherein $R^4$ and $R^5$ are as previously defined,
(7) $C_3$–$C_{10}$-alkynyl, and
(8) $C_3$–$C_{10}$-alkynyl substituted with one or more substituents selected from the group consisting of
(a) trialkylsilyl,
(b) aryl,
(c) substituted aryl,
(d) heteroaryl, and
(e) substituted heteroaryl, with the proviso that when R is allyl and $R^1$ is methyl, $R^2$ is not H;

$R^p$ is hydrogen or a hydroxy protecting group;

$R^w$ is selected from the group consisting of
(1) hydrogen,
(2) $C_1$–$C_6$-alkyl, optionally substituted with one or more substituents selected from the group consisting of
(a) aryl,
(b) substituted aryl,
(c) heteroaryl,
(d) substituted heteroaryl,
(3) a group selected from option (2) as previously defined further substituted with —$CH_2$—M—$R^8$, wherein M is selected from the group consisting of
(i) —O—,
(ii) —NH—,
(ii) —N($CH_3$)—,
(iv) —$S(O)_n$—, wherein n is as described previously,
(v) —NH—C(O)—, and
(vi) —C(O)—NH—, and
$R^8$ is selected from the group consisting of
(i) —$(CH_2)_n$-aryl, wherein n is as described previously,
(ii) —$(CH_2)_n$-substituted aryl, wherein n is as described previously,
(iii) —$(CH_2)_n$-heteroaryl, wherein n is as described previously,
(iv) —$(CH_2)_n$-substituted heteroaryl, wherein n is as described previously, and
(v) —$(CH_2)_n$-heterocycloalkyl, wherein n is as described previously; and W is absent or is selected from the group consisting of —O—, —NH— and —N($CH_3$)—, the method comprising:

(a) sequentially desmethylating 3'-nitrogen of a compound selected from the group consisting of

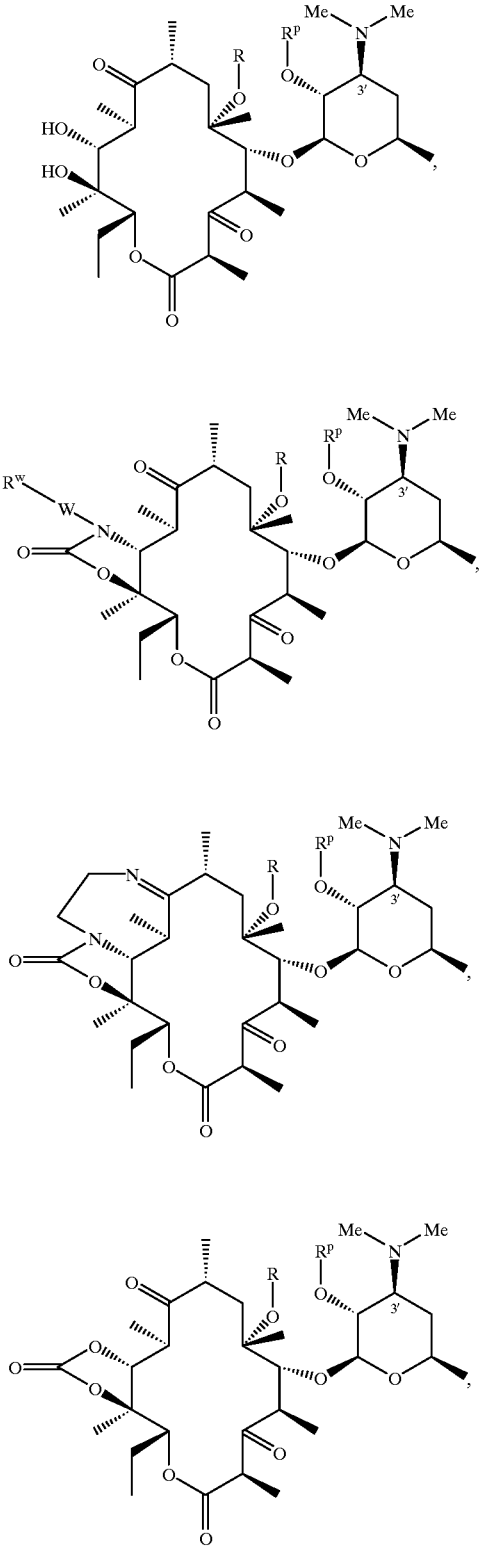

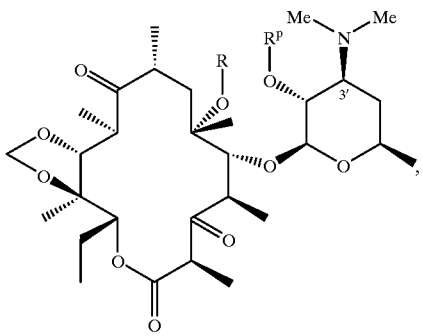

wherein R, $R^p$, W and $R^w$ are as defined previously; and (b) sequentially reacting the compound from step (a) with a $R^1$-and a $R^2$-precursor compound.

Abbreviations

Abbreviations which have been used in the descriptions of the scheme and the examples that follow are: AIBN for azobisisobutyronitrile; Bu₃SnH for tributyltin hydride; CDI for carbonyldiimidazole; DBU for 1,8-diazabicyclo[5.4.0]undec-7-ene; DEAD for diethylazodicarboxylate; DMF for dimethylformamide; DMSO for dimethylsulfoxide; DPPA for diphenylphosphoryl azide; Et₃N for triethylamine; EtOAc for ethyl acetate; Et₂O for diethyl ether; EtOH for ethanol; HOAc for acetic acid; MeOH for methanol; NaN(TMS)₂ for sodium bis(trimethylsilyl)arnide; NMMO for N-methylmorpholine N-oxide; TEA for triethylarnine; THF for tetrahydrofuran; and TPP for triphenylphosphine.

Synthetic Methods

The compounds and processes of the present invention will be better understood in connection with the following synthetic schemes 1–9 which illustrate the methods by which the compounds of the invention may be prepared. The compounds of the present invention are prepared by the representative methods described below. The groups $R^1$, $R^2$, R, $R^p$ and $R^w$ are as defined previously.

The preparation of the compounds of the invention of formula (I)–(V) from erythromycin A is outlined in Schemes 1–9. The preparation of protected erythromycin A is described in the following United States patents, U.S. Pat. No. 4,990,602; U.S. Pat. No. 4,331,803, U.S. Pat. No. 4,680,368, and U.S. Pat. No. 4,670,549 which are incorporated by reference. Also incorporated by reference is European Patent Application EP 260,938.

As shown in Scheme 1, the C-9-carbonyl group of compound 1 is protected with an oxime to give the compound 2, wherein V is =N—O—$R^3$ or =N—O—C($R^8$) ($R^9$)—O—$R^3$ where $R^3$ is defined previously and $R^8$ and $R^9$ are each independently selected from the group consisting of (a) hydrogen, (b) unsubstituted $C_1$–$C_{12}$-alkyl, (c) $C_1$–$C_{12}$-alkyl substituted with aryl, and (d) $C_1$–$C_{12}$-alkyl substituted with substituted aryl, or $R^9$ and $R^{10}$ taken together with the carbon to which they are attached form a $C_3$–$C_{12}$-cycloalkyl ring. An especially preferred carbonyl protecting group V is O-(1-isopropoxycyclohexyl) oxime.

The 2'- and 4"-hydroxy groups of 2 are protected by reaction with a suitable hydroxy protecting reagent, such as those described by T. W. Greene and P. G. M. Wuts in

*Protective Groups in Organic Synthesis*, 2nd ed., John Wiley & Son, Inc., 1991, which is incorporated by reference. Hydroxy protecting groups include, for example, acetic anhydride, benzoic anhydride, benzyl chloroformate, hexamethyldisilazane, or a trialkylsilyl chloride in an aprotic solvent. Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof. Protection of 2'- and 4"-hydroxy groups of 2 may be accomplished sequentially or simultaneously to provide compound 3 where $R^p$ is a hydroxy protecting group. A preferred protecting group $R^p$ is trimethylsilyl.

The 6-hydroxy group of compound 3 is then alkylated by reaction with an alkylating agent in the presence of base to give compound 4. Alkylating agents include alkyl chlorides, bromides, iodides or alkyl sulfonates. Specific examples of alkylating agents include allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone, 1,3-dibromo-1-propene, and the like. Examples of alkyl sulfonates are: allyl-O-tosylate, 3-phenylpropyl-O-trifluoromethane sulfonate, n-butyl-O-methanesulfonate and the like. Examples of the solvents used are aprotic solvents such as dimethylsulfoxide, diethylsulfoxide, N,N-dimethylformamide, N,N-dimethylacetamide, N-methyl-2-pyrrolidone, hexamethylphosphoric triamide, a mixture thereof or a mixture of one of these solvents with ether, tetrahydrofuran, 1,2-dimethoxyethane, acetonitrile, ethyl acetate, acetone and the like. Examples of the base which can be used include potassium hydroxide, cesium hydroxide, tetraalkylammonium hydroxide, sodium hydride, potassium hydride, potassium isopropoxide, potassium tert-butoxide, potassium isobutoxide and the like. Additional procedures for further elaboration of the 6-position moiety of the compounds of the invention are described in Schemes 2–4 below.

The deprotection of the 2'- and 4"-hydroxyl groups is then carried out according to methods described in literature, for example, by T. W. Greene and P. G. M. Wuts in *Protective Groups in Organic Synthesis*, 2nd ed., John Wiley & Son, Inc., 1991, which is incorporated herein by reference. The conditions used for the deprotection of the 2'- and 4"-hydroxyl groups usually results in the conversion of X to =N—OH. (For example, using acetic acid in acetonitrile and water results in the deprotection of the 2'- and 4"-hydroxyl groups and the conversion of X from =N—O—$R^3$ or =N—O—($R^8$)($R^9$)—O—$R^3$ where $R^3$, $R^8$ and $R^9$ are as defined previously to =N—OH.) If this is not the case, the conversion is carried out in a separate step.

The deoximation reaction can be carried out according to the methods described in the literature, for example by Greene (op. cit.) and others. Examples of the deoximating agent are inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate, potassium metabisulfite and the like. Examples of the solvents used are protic solvents such as water, methanol, ethanol, propanol, isopropanol, trimethylsilanol or a mixture of one or more of the mentioned solvents and the like. The deoximation reaction is more conveniently carried out in the presence of an organic acid such as formic acid, acetic acid and trifluoroacetic acid. The amount of acid used is from about 1 to about 10 equivalents of the amount of compound 5 used. In a preferred embodiment, the deoximation is carried out using an organic acid such as formic acid in ethanol and water to give the desired 6-O-substituted erythromycin compound 6.

Schemes 2–4 describe representative procedures for further elaboration of the 6-O-substituted moiety of the compounds of the invention. It will be appreciated by one skilled in the art that the decision as to when to perform these reactions may be dependent upon the presence of other reactive moieties within the molecule. Therefore, suitable protection and deprotection steps may be required, as are well known and applied within the art. It will sometimes be desirable to perform these modifications upon macrolide molecules such as the erythromycin derivative 6. In other instances it will be desirable to perform the operation upon a later intermediate in the preparation of compounds of the invention. Specifically, the modifications may be performed upon certain compounds of the invention, including selected compounds of formulas (I)–(V) wherein R is allyl, in order to prepare additional compounds of formulas (I)–(V).

Scheme 2 illustrates reactions suitable for modification of 6-O-allyl substituted macrolide compounds. For example, compound 7 wherein M' represents a selected macrolide derivative can be further derivatized. The double bond of the allyl compound can be (a) catalytically reduced to give the 6-O-propyl compound 8; (b) treated with osmium tetraoxide to give the 2,3-dihydroxypropyl compound 9 which in turn may be functionalized, such as by esterification with an acylating agent such as an acyl halide or acyl anhydride, at each oxygen atom to give 10; (c) oxidized with m-chloroperoxybenzoic acid in an aprotic solvent to give the epoxy methyl compound 11 which can be opened with nucleophilic compounds, for example, amines or N-containing heteroaryl compounds, to give compounds with N-containing side chains 12; (d) oxidized under Wacker conditions as described by Henry in "Palladium Catalyzed Oxidation of Hydrocarbons", Reidel Publishing Co., Dordrecht, Holland (1980), to give the 6-O—$CH_2$—C(O)—$CH_3$ compound 13; and (e) ozonized to give the aldehyde 14 which can in turn converted to oximes 15 and 16 by reaction with $H_2NOR^3$ or $H_2NOH$ respectively, or reductively aminated, such as with a suitable amine in the presence of a borohydride reducing agent or by formation of the imine and subsequent catalytic reduction, to give the amnine 17. Reaction of the oxime 16 with diisopropyl carbodiimide in an aprotic solvent in the presence of CuCl gives the nitrile 18. Reaction of 7 with an aryl halide under Heck conditions in the presence of (Pd(II) or Pd(O)), phosphine, and amine or inorganic base (see *Organic Reactions*, 1982, 27, 345–390) gives 19. Reduction of the double bond in 19, for example using $H_2$ and palladium on carbon gives 20.

Representative examples of still further elaboration of the 6-position are shown in Scheme 3. The desired 6-O-substituted compound may be prepared by chemical modification of an initially prepared 6-O-propargyl compound.

Scheme 1
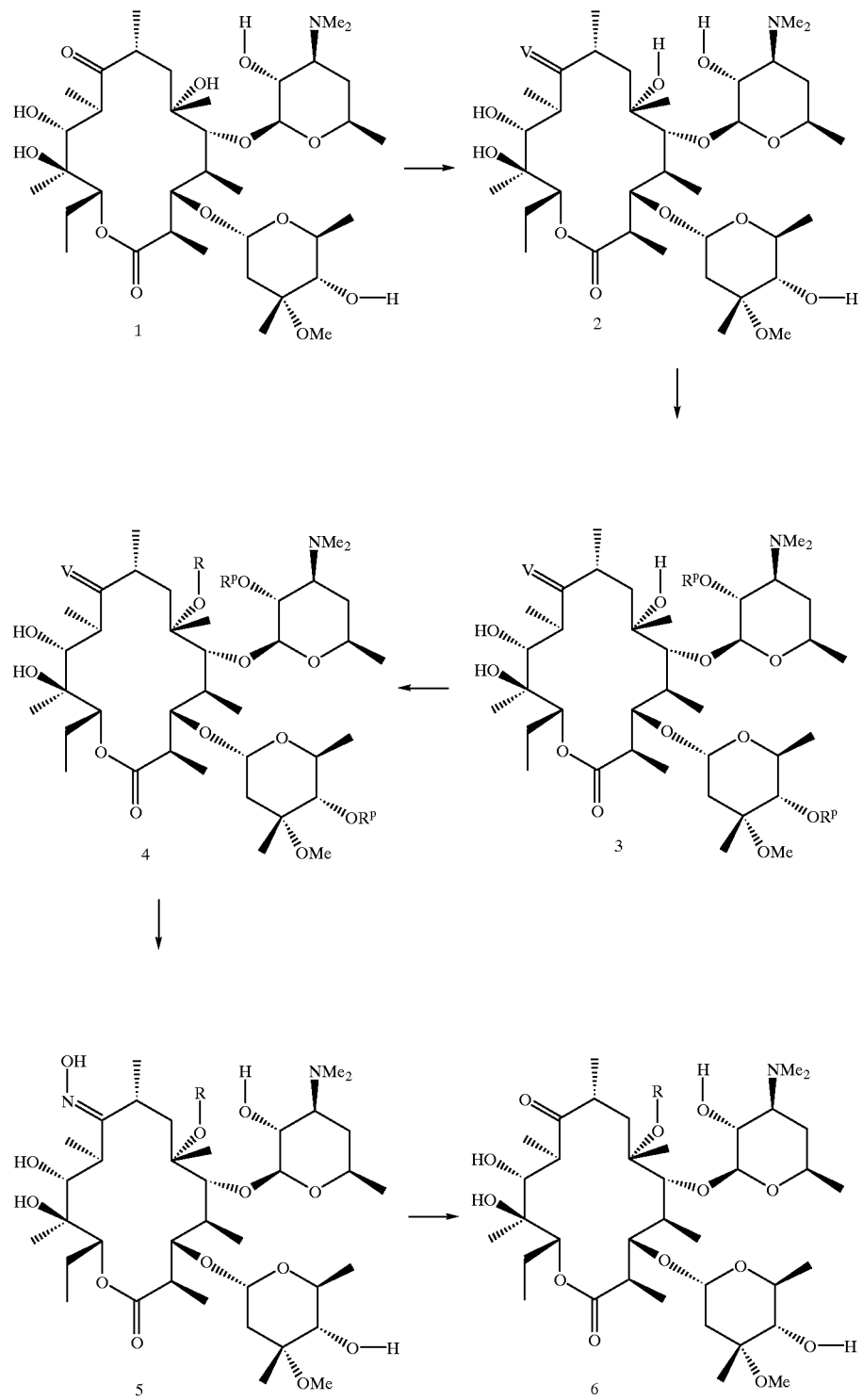

Scheme 2
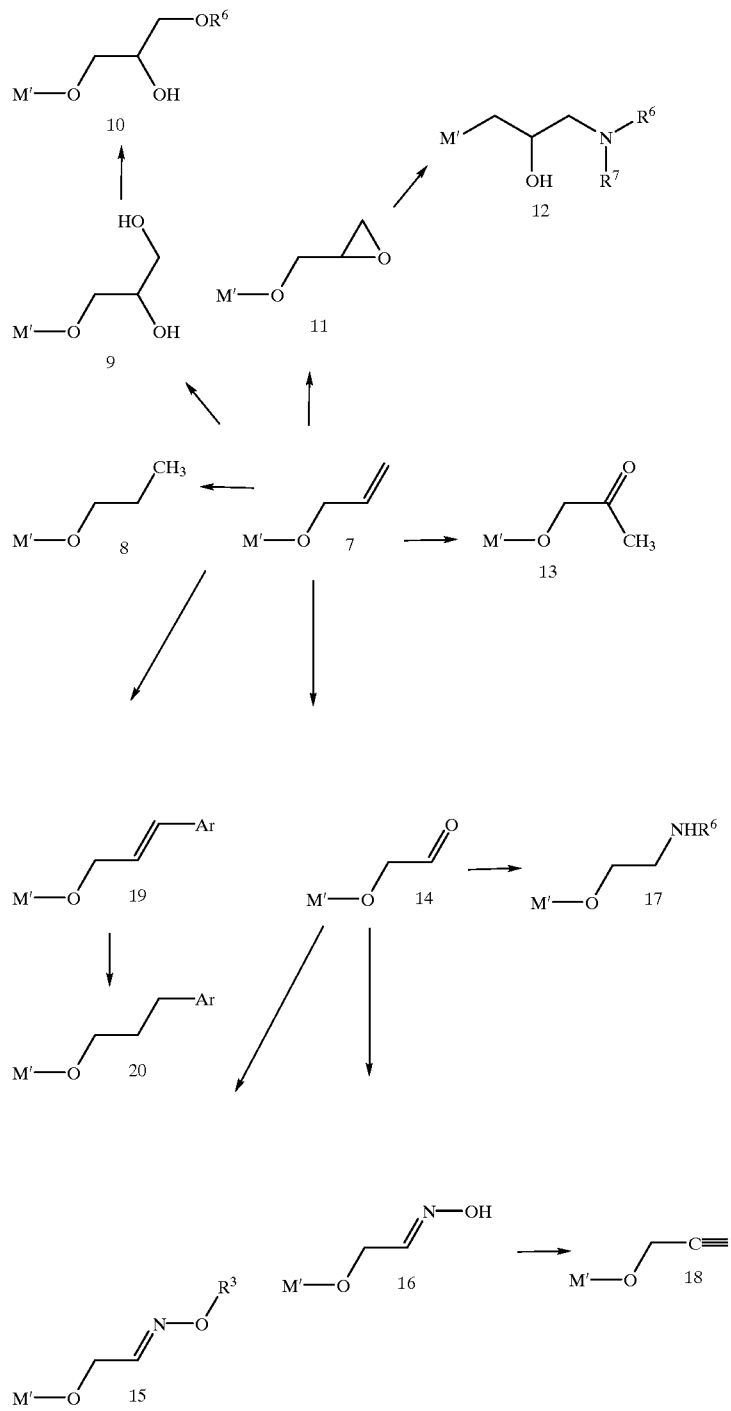

Scheme 3

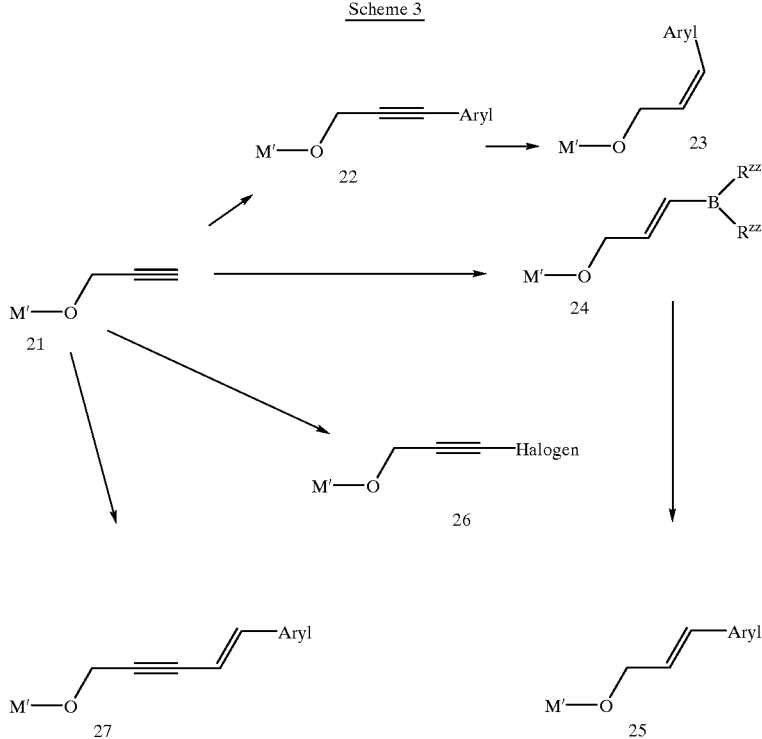

For example, compound 21, which illustrates a compound of the invention where R is propargyl and M' represents the macrolide ring system, can be further derivatized. The triple bond of compound 21 can be treated with an aryl halide, a substituted aryl halide, a heteroaryl halide or substituted heteroaryl halide in the presence of Pd(triphenylphosphine)$_2$Cl$_2$ and CuI in the presence of an organic amine, such as triethylamine, to give the compound 22. Compound 22 can be further selectively reduced to the corresponding cis-olefin compound 23 by catalytic hydrogenation in ethanol at atmospheric pressure in the presence of 5% Pd/BaSO$_4$ and quinoline (Rao et al., *J. Org. Chem.*, (1986), 51: 4158–4159). Compound 21 may also be treated with a boronic acid derivative HB(OR$^{ZZ}$), wherein R$^{ZZ}$ is H or C$_1$–C$_{10}$-alkyl, in an aprotic solvent at 0° C. to ambient temperature to give compounds 24, which are then treated with Pd(triphenylphosphine)$_4$ and an aryl halide, a substituted aryl halide, an heteroaryl halide or substituted heteroaryl halide under Suzuki reaction conditions to give compounds 25. Compound 21 may also be treated with N-halosuccinimide in acetic acid to give compounds 26. Also, compound 21 may be treated with a substituted alkenyl halide, such as Ar—CH═CH-halogen, wherein Ar is aryl, substituted aryl, heteroaryl or substituted heteroaryl, in the presence of Pd(triphenylphosphine)$_2$Cl$_2$ and CuI in the presence of an organic amine, such as triethylamine, to give the appropriately substituted compounds 27.

Scheme 4 describes the preparation of intermediates to compounds of formula (I) of the invention from the 6-substituted erythromycin derivative 6 prepared in Scheme 1. The cladinose moiety of macrolide 6 is removed either by mild aqueous acid hydrolysis or by enzymatic hydrolysis to give 28. Representative acids suitable for this procedure include dilute hydrochloric acid, sulfuric acid, perchloric acid, chloroacetic acid, dichloroacetic acid or trifluoroacetic acid. Suitable solvents for the reaction include methanol, ethanol, isopropanol, butanol, and the like. Reaction times are typically 0.5 to 24 hours, and the reaction temperature is preferably −10° C. to 35° C.

The 2'-hydroxy group of 28 is protected to give the compound 29 by means of a suitable hydroxy protecting reagent such as acetic anhydride, benzoyl anhydride, benzyl chloroformate or trialkylsilyl chloride in an aprotic solvent, as defined previously, preferably dichloromethane, chloroform, DMF, tetrahydrofuran (THF), N-methyl pyrrolidinone or a mixture thereof. A particularly preferred protecting group R$^P$ is benzoate. It is possible to reverse the order of the steps for removing the cladinose and protecting the hydroxy groups without affecting the yield of the process.

The 3-hydroxy group of 29 is oxidized to the ketone 30 using a modified Swern oxidation procedure. Suitable oxidizing agents are N-chlorosuccinimide-dimethyl sulfide or carbodiimide-dimethylsulfoxide. In a typical example, 29 is added into a pre-formed N-chlorosuccinimide and dimethyl sulfide complex in a chlorinated solvent such as methylene chloride at −10° C. to 25 C. After being stirred for about 0.5 to 4 hours, a tertiary amine, such as triethylamine or Hunig's base, for example, is added to produce the ketone 30 wherein R$^P$ is a hydroxy protecting group. The conversion of intermediate compound 30 to a compound of the invention is shown below in Scheme 9.

Scheme 4

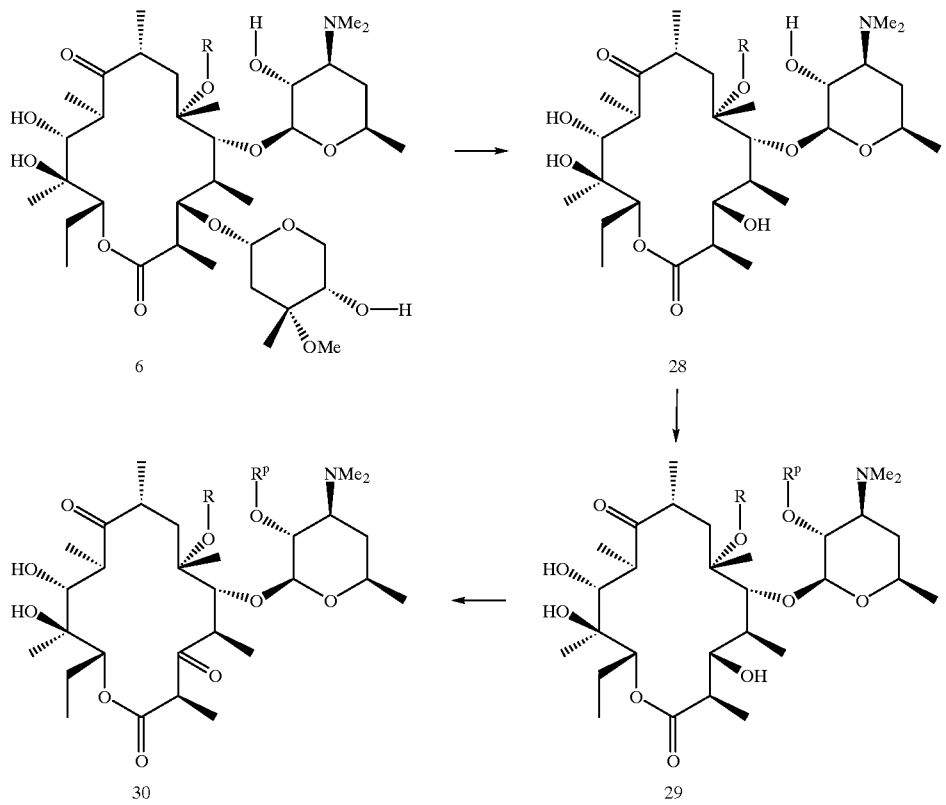

Scheme 5 illustrates the preparation of the compounds of formula (II). Accordingly, compound 6 is first protected with a suitable hydroxy protecting group to give compound 31, by the procedures referenced previously. Compound 31 is then treated with an excess of sodium hexamethyldisilazide or a hydride base in the presence of carbonyldiimidazole in an aprotic solvent for 8 to 24 hours at about −30° C. to room temperature to give compound 32. The hydride base may be, for example, sodium hydride, potassium hydride, or lithium hydride, and the aprotic solvent may be one as defined previously. The reaction is preferably maintained under an inert atmosphere, such as nitrogen or argon, for example. The reaction may require cooling or heating from about −20° C. to about 70° C., depending on the conditions used, and preferably from about 0° C. to about room temperature. The reaction requires about 0.5 hours to about 10 days, and preferably about 1–5 days, to complete. Portions of this reaction sequence follow the procedure described by Baker et al., *J. Org. Chem.*, 1988, 53, 2340, which is incorporated herein by reference.

Scheme 5

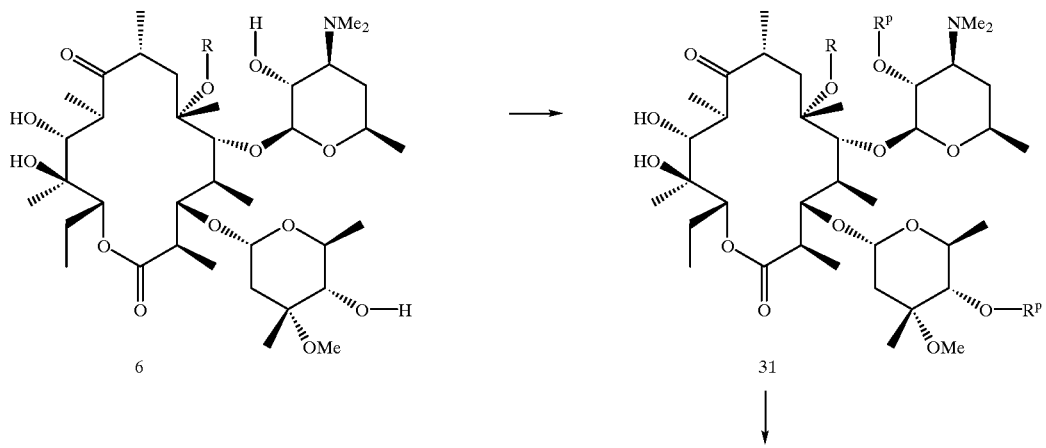

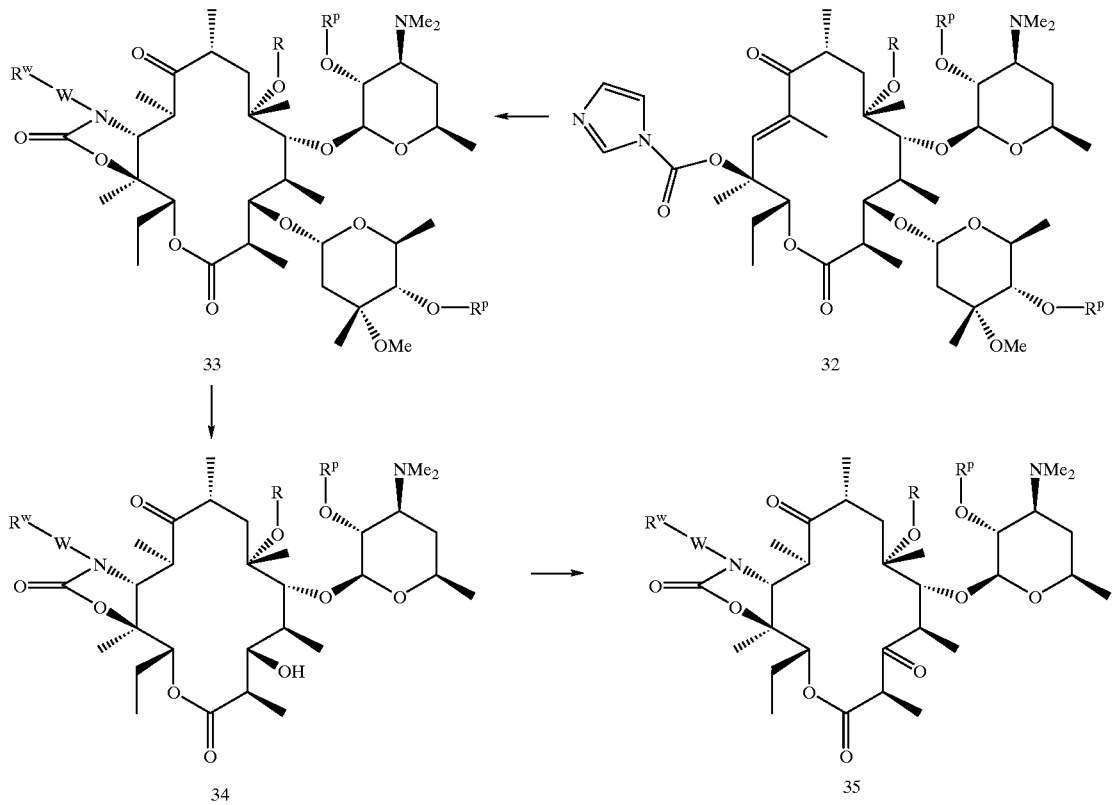

Compound 32 can then be used to form a wider series of intermediate compound to formula (II). For example, treatment of compound 32 with aqueous ammonia results in formation of the cyclic carbamate 33 wherein W is absent and $R^w$ is H. Likewise, reaction of compound 6B with a substituted amide of the formula $H_2N$—$R^w$ results in formation of the cyclic carbamate 33

Treatment of compound 32 with a substituted amine compound of the formula $H_2N$—W—$R^w$, wherein W is absent and $R^w$ is as previously defined except not H gives 33 in which W is —NH— and $R^w$ is as previously defined except not H.

Also, treatment of compound 32 with a hydroxylamine compound of the formula $H_2N$—W-$R^w$, wherein W —O— and $R^w$ is as previously defined, results in formation of 33 wherein W is —O— and $R^w$ is as previously defined.

Treatment of compound 32 with unsubstituted hydrazine results in formation of the cyclic carbamate 33 wherein W is —NH— and $R^w$ is H.

Treatment of compound 32 with a substituted hydrazine compound of the formula $H_2N$—NH—$R^w$, wherein $R^w$ is as previously defined except not H, results in formation of 33 wherein W is —NH— and $R^w$ is as previously defined except not H.

Alternate or additional procedures may be used to prepare intermediates of formula (II). For example, treatment of a compound 32 wherein W is absent and $R^w$ is H with an alkylating agent having the formula $R^w$-halogen, wherein $R^w$ is as previously defined except not H, gives a compound 33 wherein W is absent and $R^w$ is not hydrogen.

Similarly, treatment of a compound 32 wherein W is —NH— and $R^w$ is H with an alkylating agent having the formula $R^w$-halogen, wherein $R^w$ is as previously defined except not H, gives a compound 33 wherein W is —NH— and $R^w$ is not hydrogen.

Treatment of compound 32 wherein W is absent and $R^w$ is H with an acylating agent selected from the group consisting of the acyl halide $R^w$—C(O)-halogen and the acid anhydride $(R^w$—$C(O))_2$—O, wherein $R^w$ is as previously defined except not H, gives a compound 33 wherein W is —NH—CO— and $R^w$ is as previously defined.

Treatment of a compound 32 wherein W is —NH— and $R^w$ is H with an aldehyde $R^w$—CHO, wherein $R^w$ is as previously defined, gives a compound 33 wherein W is —N=CH— and $R^w$ is as previously defined.

Removal of the cladinose moiety from a compound 33 by acid hydrolysis as described previously gives a compound 34. The 3-hydroxy group of 34 is oxidized to the ketone 35 using a modified Swern oxidation procedure as described previously. The conversion of intermediate compound 35 to a compound (II) of the invention is shown below in Scheme 9.

Scheme 6 describes the preparation of intermediate compounds for formula (III). Compound 32 is treated with ethylenediamine 36 in a suitable solvent such as aqueous acetonitrile, DMF or aqueous DMF, to give the bicyclic carbamate intermediate (not shown) which is then cyclized by treatment with dilute acid, such as acetic acid or HCl, in a suitable organic solvent such as ethanol or propanol, to give compound 37.

The cladinose moiety is then removed from compound 37 to give compound 38. The 3-hydroxy group of 38 is oxidized to the ketone 39 using a modified Swern oxidation procedure as described previously. The conversion of intermediate compound 39 to a compound (III) of the invention is shown below in Scheme 9.

Scheme 6
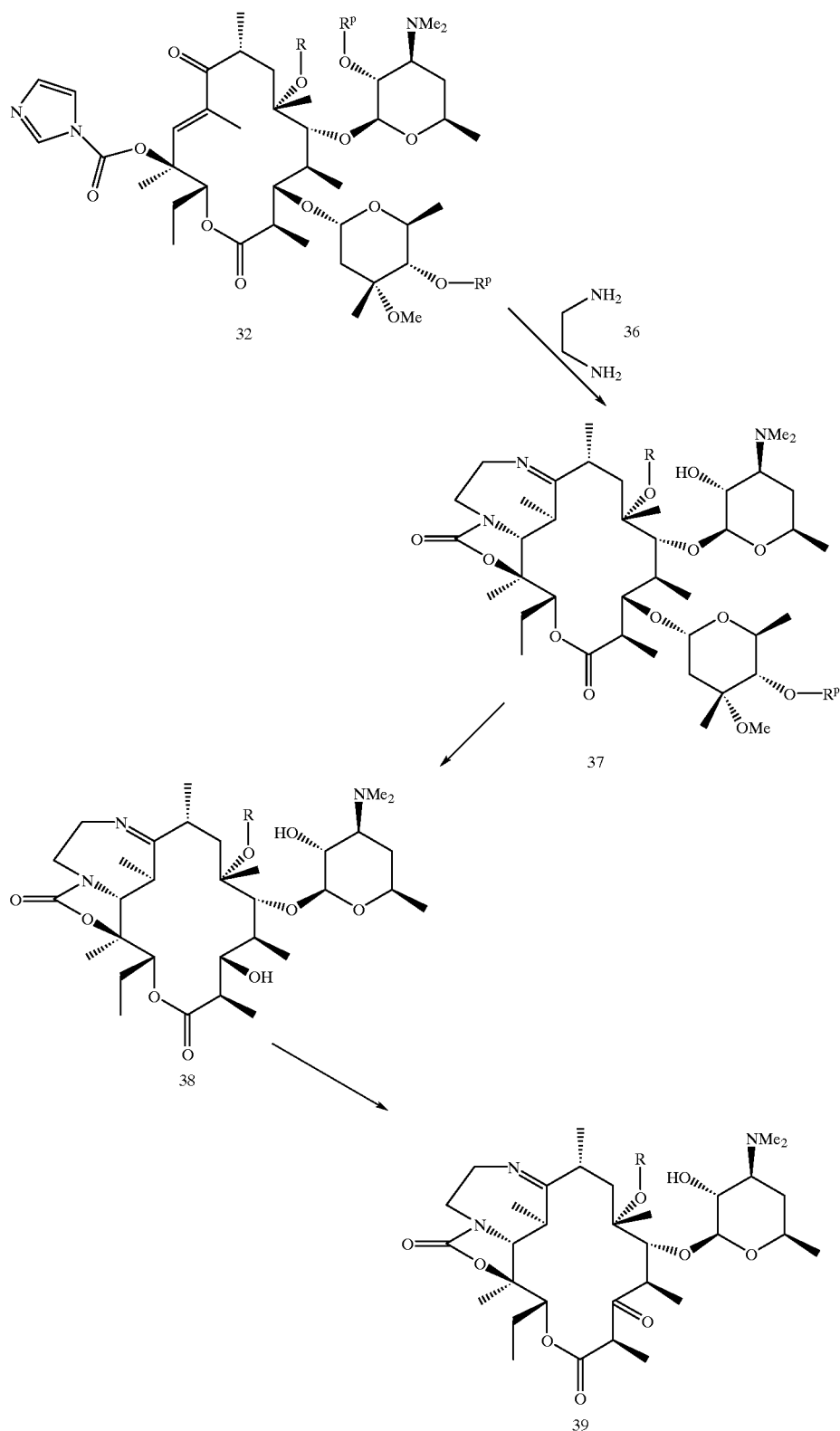
Scheme 7 illustrates the preparation of the cyclic carbonate compounds of formula (IV). In particular, the 2'-protected compound 30, prepared as shown in Scheme 4, is converted to the cyclic carbonate 40 by controlled reaction at low temperatures (about −30° C.) for a short period (about 30 minutes) with carbonyldiimidazole and sodium hexamethyldisilazide. Alternately, compound 40 is prepared from 30 by careful reaction with sodium hydride or lithium hydride and phosgene, diphosgene or triphosgene under anhydrous conditions with careful control of the amount of base present in order to prevent base catalyzed decarboxylation. The conversion of intermediate compound 40 to a compound (IV) of the invention is shown below in Scheme 9.

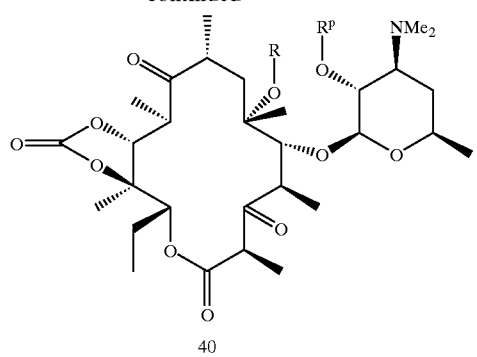

Scheme 7

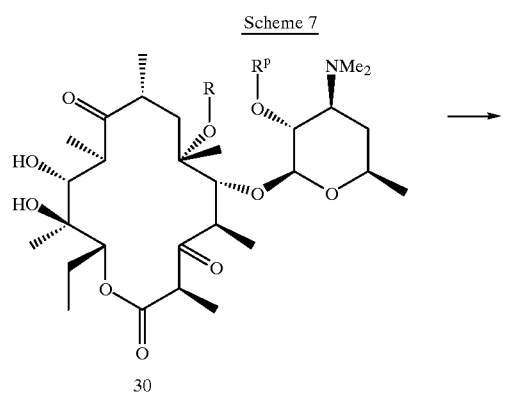

Scheme 8 illustrates the preparation of the cyclic methylene compounds of formula (V). Compound 31 may be treated with formaldehyde in the presence of an acid, or with chloroiodomethane in the presence of base (according to the procedure of Hunt et al., *J. Antibiotics*, (1988), 41: 1644) to give the protected 11,12-methylenedioxy compound 41 which is an intermediate to compounds of formula (V). Compound 41 is hydrolyzed to give compound 42. The 3-hydroxy group of 42 is oxidized to the ketone 43 using a modified Swern oxidation procedure as described previously. The conversion of intermediate compound 43 to a compound (IV) of the invention is shown below in Scheme 9.

Scheme 8

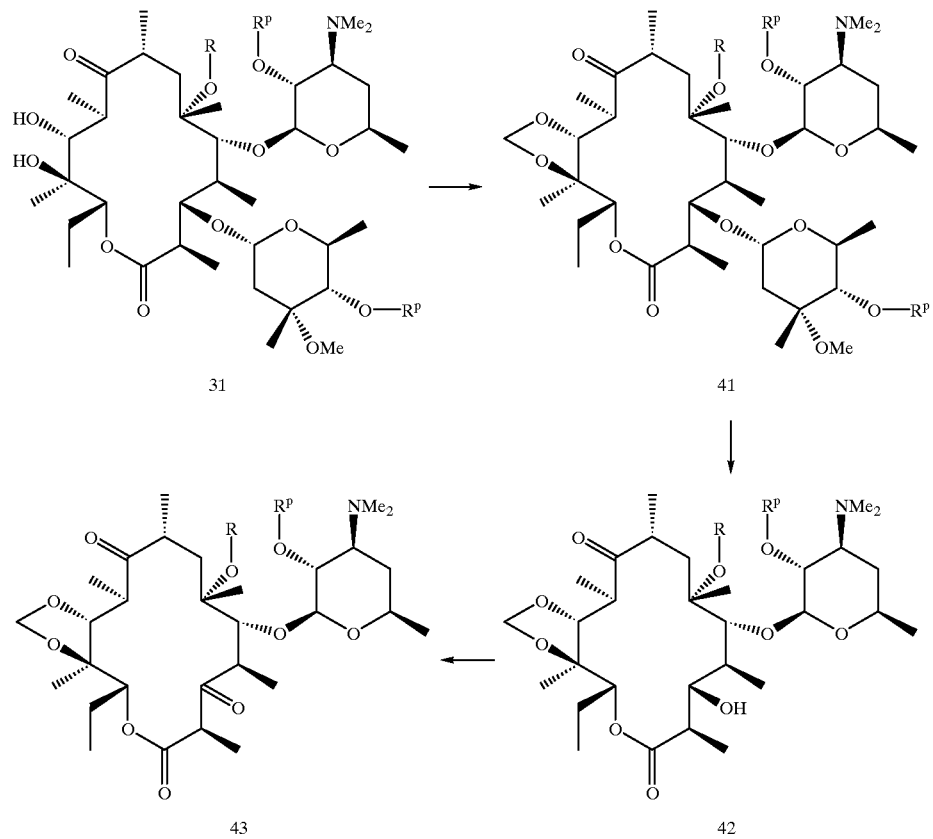

Scheme 9 describes procedures whereby compounds 30, 35, 39, 40, or 43 can be converted to the desired compound of formulas (I)–(V) of the invention. Compounds 30, 35, 39, 40, or 43 are treated with N-iodosuccinimide to give compound 44 wherein one of $R^1$ and $R^2$ is H and the other is methyl. For convenience $R^2$ is shown as the methyl group.

Compound 44 can be reacted in the presence of base with a suitable $R^1$-precursor compound such as $R^1$—X, wherein $R^1$ is as defined previously and X is a suitable leaving group, such as a halide or a sulfonate, such as methyl sulfonate, tosylate or trifluoromethylsulfonate, for example, to give compound 45. Alternately, compound 44 can be reductively alkylated with an aldehyde of formula R*—CHO, which when reduced becomes R*—CH$_2$—which is the $R^1$ moiety described previously, in the presence of a reducing agent such as NaBH$_3$CN or H$_2$ and Pd/C. Typically, suitable $R^1$-precursor compounds are $C_1$–$C_6$-alkyl halides or sulfonates optionally substituted with a group such as halogen, $C_3$–$C_6$-cycloalkyl, aryl, substituted-aryl, heteroaryl, and substituted-heteroaryl.

Other suitable precursor compounds are $C_2$–$C_6$-alkyl halides or sulfonates optionally substituted with a substituent group such as $C_1$–$C_6$-alkoxy, an amine group —NR'R", wherein R' and R" are independently selected from hydrogen, $C_1$–$C_3$-alkyl, $C_1$–$C_3$-alkyl substituted with aryl, substituted aryl, heteroaryl, and substituted heteroaryl, —NH—C(O)—$C_1$–$C_6$-alkyl, —NH—C(O)—O—$C_1$–$C_6$-alkyl, —O—(O)—O—$C_1$–$C_6$-alkyl, —O—(O)—$C_1$–$C_6$-alkyl, —CHO, —C(O)—$C_1$–$C_6$-alkyl, —C(O)—NR'R", wherein R' and R" are as previously defined, CH(=N—O—$C_1$–$C_6$-alkyl), C(=N—O—$C_1$–$C_6$-alkyl)—$C_1$–$C_6$-alkyl, C(=N—NH—$C_1$–$C_6$-alkyl)—H, and C(=N—NH—$C_1$–$C_6$-alkyl)—$C_1$–$C_6$-alkyl.

Other additional precursor compounds are $C_3$–$C_6$-alkenyl halides optionally substituted with a substituent group such as halogen, $C_3$–$C_6$-cycloalkyl, aryl, substituted aryl, heteroaryl, and substituted heteroaryl, $C_1$–$C_6$-alkoxy, an amine group —NR'R", wherein R' and R" are independently selected from hydrogen, $C_1$–$C_3$-alkyl, $C_1$–$C_3$-alkyl substituted with aryl, substituted aryl, heteroaryl, and substituted heteroaryl, —NH—C(O)—$C_1$–$C_6$-alkyl, —NH—C(O)—O—$C_1$–$C_6$-alkyl, —(O)—O—$C_1$–$C_6$-alkyl, —(O)—$C_1$–$C_6$-alkyl, —C(O)—H C(O)—$C_1$–$C_6$-alkyl, —C(O)—NR'R", wherein R' and R" are as previously defined, —CH(=N—O—$C_1$–$C_6$-alkyl), —C(=N—O—$C_1$–$C_6$-alkyl)—$C_1$–$C_6$-alkyl, —CH(=N—NH—$C_1$–$C_6$-alkyl), and C(=N—NH—$C_1$–$C_6$-alkyl)—$C_1$–$C_6$-alkyl. It will be obvious to those skilled in the art that certain of the substituents may not be directly substituted upon an unsaturated carbon atom.

Other additional precursor compounds are $C_3$–$C_6$-alkynyl halides optionally substituted with a substituent group such as halogen, $C_3$–$C_6$-cycloalkyl, aryl, substituted-aryl, heteroaryl, and substituted-heteroaryl.

Further additional precursor compounds are $C_3$–$C_6$-cycloalkylhalides optionally substituted with a substituent group such as halogen, $C_3$–$C_6$-cycloalkyl, aryl, substituted-aryl, heteroaryl, and substituted-heteroaryl.

Also, however, the compound 44 may be treated with a formulating agent or an acylating agent of the formula X—C(O)—R', wherein X is halogen and R' is as defined previously, or O—(C(O)—R')$_2$ to prepare the appropriate derivative wherein $R^1$ is formyl or C(O)—R', respectively, to give compound 45. Alternately, compound 44 can be reacted with carbonyldiimidazole to give an intermediate compound 45 wherein $R^1$ is imidazolylcarbonyl, and this intermediate is reacted with an amine having the formula HNR'R", to give the compound 45 wherein $R^1$ is C(O)—NR'R". Further, compound 44 can be reacted with an alcohol of the formula HOR' to give a compound wherein $R^1$ is C(O)—OR', wherein R' is as previously defined, to give a compound 45 wherein $R^1$ is C(O)—O—R'.

Compound 44 can also be reacted with a substituted or unsubstituted aryl alcohol in the presence of a homologating agent such as formaldehyde or paraformaldehyde to give a compound wherein $R^1$ is methyl substituted with substituted aryl.

Compound 44 can be treated again with N-iodosuccinimide or with iodine in the presence of light to give compound 46 wherein both $R^1$ and $R^2$ are H. Compound 46 may then be treated in the presence of base with one of the $R^1$-precursor reagents described previously to give compound 47.

Compound 47 may then be treated with a $R^2$-precursor reagent similar to the $R^1$-precursor reagent described previously and under similar conditions to give the appropriately disubstituted compound 48.

In the instance wherein $R^1$ and $R^2$ taken together may be —(CH$_2$)$_p$—, wherein p is 3–7, which taken together with the nitrogen atom to which they are attached thus forms a heterocyclic ring containing one nitrogen atom and from 3 to 7 carbon atoms, the precursor can be a suitable alkyl dihalide, such as 1,3-dibromopropane, 1,4-dibromobutane, 1,5-dibromopentane, 1,6-dibromohexane, or 1,7-dibromoheptane, for example.

When $R^P$ of formula (I)–(V) is a hydroxy protecting group such as acetate or benzoate, the compound may be deprotected by treatment with methanol or ethanol to give a compound of formula (I) wherein $R^P$ is hydrogen. When $R^P$ is a trialkylsilyl group, the compound may be deprotected by treatment with fluoride in THF or acetonitrile to give a compound of formula (I)–(V) wherein $R^P$ is hydrogen.

The foregoing may be better understood by reference to the following examples which are presented for illustration and not to limit the scope of the inventive concept.

Scheme 9

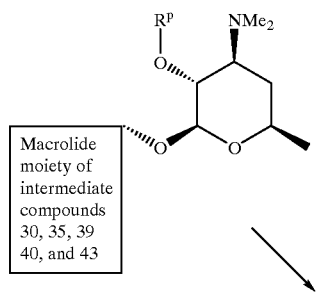

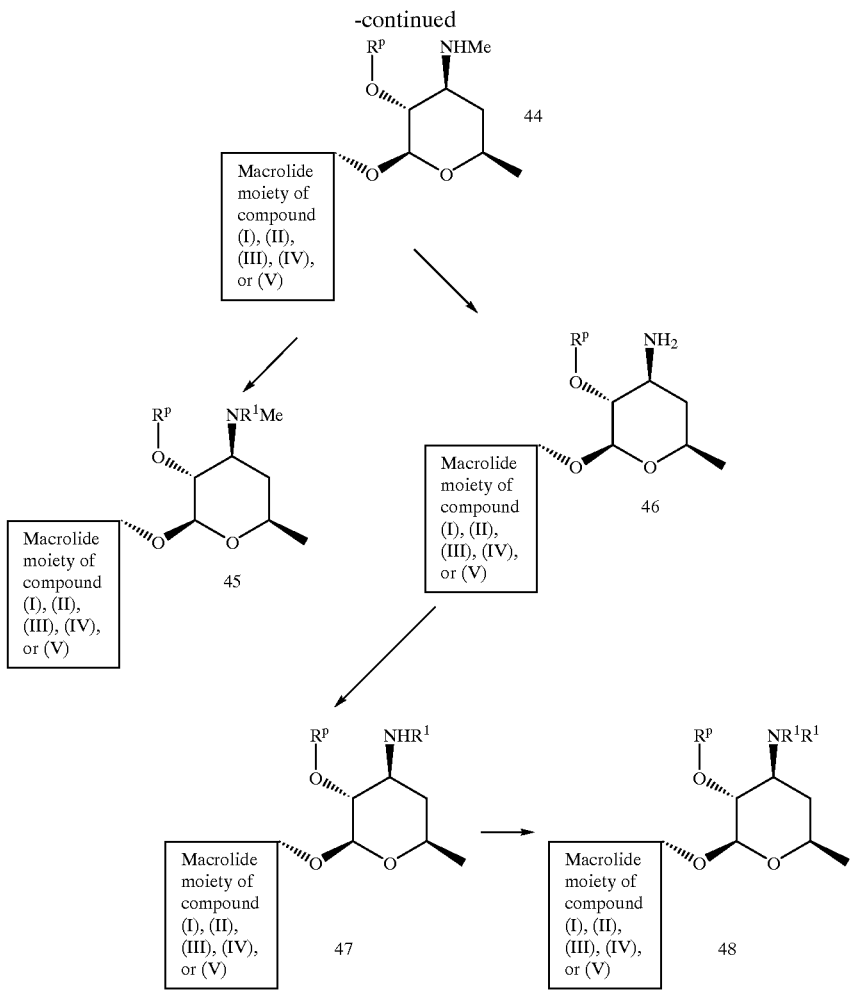

Example 1

Compound of Formula (I), R is —CH₂CH═CH-(3-quinolyl), R$^P$ is H, R$^1$ is methyl, R$^2$ is hydrogen Step 1a: Compound 4 from Scheme 1, V is N—O-(1-isopropoxycyclohexyl), R is allyl, R$^P$ is trimethylsilyl To a 0° C. solution of 2',4"-bis-O-trimethylsilylerythromycin A 9-[O-(1-isopropoxycyclohexyl)oxime (1.032 g, 1.00 mmol), prepared according to the method of U.S. Pat. No. 4,990,602 in 5 mL of DMSO and 5 mL of THF was added freshly distilled allyl bromide (0.73 mL, 2.00 mmol). After approximately 5 minutes, a solution of potassium tert-butoxide (1 M 2.0 mL, 2.0 mL) in 5 mL of DMSO and 5 mL of THF was added dropwise over 4 hours. The reaction mixture was taken up in ethyl acetate and washed with water and brine. The organic phase was concentrated in vacuo to give the desired compound (1.062 g) as a white foam.

Step 1b: Compound 5 from Scheme 1, V is NOH, R is allyl

To a solution of the compound resulting from step 1a (1.7 g) in 17 mL of acetonitrile and 8.5 mL of water was added 9 mL of acetic acid at ambient temperature. After several hours at ambient temperature, the reaction mixture was diluted with 200 mL of toluene and concentrated in vacuo. The residue obtained was found to contain unreacted starting material, so additional acetonitrile (15 mL), water (70 mL) and HOAc (2 mL) was added. After 2 hours, an additional 1 mL aliquot of HOAc was added. After approximately three more hours, the reaction mixture was placed in the freezer overnight. The reaction mixture was allowed to warm to ambient temperature, diluted with 200 mL of toluene and concentrated in vacuo. The residue was chased twice with toluene and dried to constant weight (1.524 g).

Step 1c: Compound 6 from Scheme 1, R is allyl

The compound resulting from step 1b (1.225 g) in 16 mL of 1:1 ethanol-water was treated with NaHSO₃ (700 mg) and formic acid (141 µL) and warmed at 86° C. for 2.5 hours. The reaction mixture was allowed to cool to ambient temperature, diluted with 5–6 mL of water, basified with 1 N NaOH to pH 9–10 and extracted with ethyl acetate. The combined organic extracts were washed with brine (2×), dried over MgSO₄, filtered and concentrated in vacuo. The crude material was purified by column chromatography eluting with 1% MeOH in methylene chloride containing 1% ammonium hydroxide to give 686 mg (57%) of the title compound. $^{13}$C NMR (CDCl₃) δ 219.3 (C-9), 174.8 (C-1), 135.5 (C-17), 116.3 (C-18), 101.9 (C-1'), 95.9 (C-1"), 79.7 (C-5), 78.8 (C-6), 78.5 (C-3), 74.1 (C-12), 72.4 (C-3"), 70.6 (C-11), 68.1 (C-5'), 65.5 (C-16), 65.1 (C2'), 49.0 (C-3" O—CH₃), 45.0 (C-2), 44.1 (C-8), 39.7 (NMe₂), 37.9 (C-4), 37.1 (C-10), 34.6 (C-2"), 28.4 (C-4'), 21.0, 20.6 (C3" CH3, C-6' CH₃), 20.8 (C-14), 18.3 (C-6"), 18.1 (C-8 CH₃), 15.7, 15.6 (C-2 CH₃, C-6 CH₃), 11.9 (C-10 CH₃), 10.1 (C-15), 8.9 (C-4 CH₃). MS (FAB)+m/e 774 (M+H)$^+$, 812 (M+K)$^+$.

Step 1d: Compound 28 from Scheme 4, R is allyl

To a suspension of the compound prepared in step 1c (7.73 g, 10.0 mmol) in ethanol (25 mL) and water (75 mL)

was added aqueous 1 M HCl (18 mL) over 10 minutes. The reaction mixture was stirred for 9 hours at ambient temperature and then was left standing in the refrigerator overnight. Aqueous 2 M NaOH (9 mL, 18 mmol) which resulted in the formation of a white precipitate. The mixture was diluted with water and filtered. The solid was washed with water and dried under vacuum to give the des-cladinosyl compound 7 (3.11 g).

Step 1e: Compound 29 from Scheme 4, R is allyl, $R^p$ is benzoyl

To a solution of the product of step 1d (2.49 g, 4.05 mmol) in dichloromethane (20 mL) was added benzoic anhydride (98%, 1.46 g, 6.48 mmol) and triethylamine (0.90 mL, 6.48 mmol) and the white suspension was stirred for 26 hours at ambient temperature. Aqueous 5% sodium carbonate was added and the mixture was stirred for 20 minutes. The mixture was extracted with dichloromethane. The organic phase was washed with aqueous 5% sodium bicarbonate and brine, dried over sodium sulfate and concentrated in vacuo to give a white foam. Chromatography on silica gel (30% acetone-hexanes) gave the title compound (2.46 g) as a white solid.

Step 1f: Compound 30 from Scheme 4, R is allyl, $R^p$ is benzoyl

To a $-10°$ C. solution under $N_2$ of N-chlorosuccinimide (0.68 g, 5.07 mmol) in dichloromethane (20 mL) was added dimethylsulfide (0.43 mL, 5.92 mmol) over 5 minutes. The resulting white slurry was stirred for 20 minutes at $-10°$ C. and then a solution of the compound resulting from step 1e (2.43 g, 3.38 mmol) in dichloromethane (20 mL) was added and the reaction mixture was stirred for 30 minutes at $-10$ to $-5$ ° C. Triethylamine (0.47 mL, 3.38 mmol) was added dropwise over 5 minutes and the reaction mixture was stirred for 30 minutes at 0 ° C. The reaction mixture was extracted with dichloromethane. The organic phase was washed twice with aqueous 5% sodium bicarbonate and once with brine, dried over sodium sulfate, and concentrated in vacuo to give a white foam. Chromatography on silica gel (30% acetone-hexanes) gave the title compound (2.27 g) as a white foam.

Step 1g: Compound of Formula (I), R is allyl, $R^p$ is benzoyl, $R^1$ is methyl, $R^2$ is hydrogen To a sample of the compound from step 1f (215 mg, 0.30 mmol) in acetonitrile (10 mL) at 0° C. under nitrogen was added N-iodosuccinimide (101 mg, 0.45 mmol), and the mixture was warmed to room temperature. After 5 hours dichloromethane (50 mL) was added, and the mixture was washed with 1:1 5% NaHSO3/Na2CO$_3$ (pH 9) and brine, dried (Na2SO4) and concentrated. The residue was chromatographed on silica gel, eluting with 3:7 acetone/hexane to give the crude product. This material was dissolved in THF (5 mL) and stirred with 5% Na2CO3 (5 mL) for 2 hours. The mixture was diluted with ethyl acetate (30 mL), and the resulting solution was washed with 5% Na2CO3 and brine, dried (Na2SO4) and concentrated. The residue was chromatographed on silica gel, eluting with 3:7 acetone/hexane to give the title compound (75.5 mg).

Step 1h: Compound of Formula (I), R is allyl, $R^p$ is H, $R^1$ is methyl, $R^2$ is hydrogen The compound from step 1g was heated at reflux in methanol under nitrogen for 6 hours, then the solvent was removed. The residue was chromatographed on silica gel, eluting with 95:5:0.5 dichlormethane/methanol/NH4OH to give the title compound (48.7 mg). Anal. Calcd. for $C_{31}H_{53}NO_{10}$·0.5 $H_2O$: C, 61.16; H, 8.94; N, 2.30; Found: C, 61.33; H, 8.89; N, 2.24. MS m/e 600 (M+H)$^+$.

Step 1i: Compound of Formula (I), R is —CH$_2$CH=CH-(3-quinolyl), $R^p$ is H, $R^1$ is methyl, $R^2$ is hydrogen A mixture of the compound from Step 1h, palladium(II) acetate and tri-o-tolylphosphine in acetonitrile (400 ml) is flushed with nitrogen. To this solution is added 3-bromoquinoline and triethylamine. The reaction mixture is heated at 50° C. for 1 hour and stirred at 90° C. for 4 days. The reaction mixture is taken up in ethyl acetate and washed with aqueous 5% sodium bicarbonate and brine, dried over sodium sulfate, filtered, and concentrated in vacuo. Chromatography on silica gel gives the title compound.

Example 2

Compound of formula (II), R is —CH$_2$CH=CH-(3-quinolyl), $R^p$ is acetyl, $R^1$ is H, $R^2$ is CH$_3$, W is absent, $R^w$ is H Step 2a. Compound 31 from Scheme 5: R is —CH$_2$CH=CH$_2$, $R^p$ is acetyl To a sample of the compound from Example 1 step c (405.2 g, 528 mmol) in dichloromethane (20 mL) was added dimethylaminopyridine(0.488 g, 4 mmol) and acetic anhydride (3.39 mL, 36 mmol), and the mixture was stirred at room temperature for 3 hours. The mixture was diluted with methylene chloride, then washed with 5% aqueous sodium bicarbonate and brine and dried over Na$_2$SO$_4$. The residue was dried and recrystallized from acetonitrile to give the title compound (491 g). MS m/e 857 (M+H)$^+$.

Step 2b. Compound 32 from Scheme 5: R is —CH$_2$CH=CH$_2$, $R^p$ is acetyl

To a sample of the compound from step 2a (85.8 g, 100 mmol) in dry THF (500 mL) cooled to $-40°$ C. and flushed with nitrogen was added sodium bis(trimethylsilyl)amide (125 mL, 125 mmol) over 20 minutes, and the mixture was stirred at $-40°$ C. for 40 minutes. To this mixture was added a solution of carbonyldiimidazole (3.65 g, 22.56 mmol) in 5:3 THF/DMF (800 mL) under nitrogen at $-40°$ C. over 30 minutes, and the mixture was stirred at $-20°$ C. for 30 minutes. The mixture was stirred at room temperature for 27 hours, then diluted with ethyl acetate. The mixture was washed with 5% sodium bicarbonate and brine, dried over Na$_2$SO$_4$, and concentrated to give the title compound (124 g), which was taken directly to the next step.

Step 2c. Compound 33 from Scheme 5: R is —CH$_2$CH=CH$_2$, $R^p$ is acetyl, W is absent, $R^w$ is H The compound from step 2b (124 g) was dissolved in 9:1 acetonitrile/THF (1100 mL), ammonium hydroxide (28%, 200 mL) was added, and the mixture was stirred at room temperature under nitrogen for 8 days. The solvent was removed, and the residue was dissolved in ethyl acetate. This solution was washed with 5% sodium bicarbonate and brine, dried over Na$_2$SO$_4$, and concentrated to give the title compound. MS (FAB)+m/e 882 (M+H)$^+$.

Step 2d. Compound 34 from Scheme 5: R is —CH$_2$CH=CH$_2$, $R^p$ is acetyl, W is absent, $R^w$ is H To a sample of the compound from step 2c (69.0 g, 78.2 mmol) suspended in ethanol (200 mL) and diluted with water (400 mL) was added HCl (0.972 N, 400 mL) dropwise over 20 minutes. The mixture was stirred for 4 hours, and additional HCl was added (4 N, 100 mL) over 20 minutes. The mixture was stirred for 18 hours, cooled to 0° C., then NaOH (4 N, 200 mL) was added over 30 minutes to approximately pH 9. The title compound was isolated by filtration (35.56 g)

Step 2e. Compound 35 from Scheme 5; R is —CH$_2$CH=CH$_2$, $R^p$ is acetyl, W is absent, $R^w$ is H To a $-10°$ C. solution under nitrogen of N-chlorosuccinimide (2.37 g, 17.8 mmol) in dichloromethane (80 mL) was added dimethylsulfide (1.52 mL, 20.8 mmol) over 5 minutes. The resulting white slurry was stirred for 10 minutes at −10° C., a solution of the compound from step 2d (8.10 g, 11.9 mmol) in dichloromethane (60 mL) was added and the reaction mixture was stirred for 30 minutes at −10 to −5° C. Triethylamine (1.99 mL, 14.3 mmol) was added dropwise over 10 minutes and the reaction mixture was stirred for 1 hour at 0° C. The reaction mixture was extracted with dichloromethane. The organic phase was washed with aqueous 5% sodium bicarbonate and brine, dried over sodium sulfate, and concentrated in vacuo to give a white foam. Chromatography on silica gel (eluting with 50:50:0.5 acetone/hexanes/ammonium hydroxide) gave the title compound (8.27 g) as a white foam. Anal. Calcd. for $C_{35}H_{56}N_2O_{11}$: C, 61.75; H, 8.29; N, 4.11; Found: C, 62.25; H, 8.50; N, 4.28.

Step 2f. Compound 35 from Scheme 5: R is —$CH_2CH=CH$-(3-quinolyl), $R^p$ is acetyl, W is absent, $R^w$ is H A mixture of the compound from Step 2e (46.36 g, 68.2 mmol), palladium(II)acetate (3.055 g, 13.6 mmol), and tri-o-tolylphosphine (8.268 g, 27.2 mmol) in acetonitrile (400 mL) was flushed with nitrogen. To this solution was added 3-bromoquinoline (18.45 mL, 136 mmol) and triethylamine (18.92 mL, 13.6 mmol) via syringe. The reaction mixture was heated at 50° C. for 1 hour and stirred at 90° C. for 4 days. The reaction mixture was taken up in ethyl acetate and washed with aqueous 5% sodium bicarbonate and brine, dried over sodium sulfate, filtered, and concentrated in vacuo. Chromatography on silica gel (eluting with 50:50:0.5 acetone/hexanes/ammonium hydroxide) gave the title compound (46.56 g) as a white foam. MS m/e 808 $(M+H)^+$.

Step 2g. Compound of formula (II), R is —$CH_2CH=CH$-(3-quinolyl), $R^p$ is acetyl, $R^1$ is H, $R^2$ is $CH_3$, W is absent, $R^w$ is H To a sample of the compound from step 2f (2.65 g, 3.3 mmol) in dry acetonitrile (110 mL) at 0° C. under nitrogen was added N-iodosuccinimide (0.887 g, 3.94 mmol) in portions, and the mixture was held at 5° C. overnight. Then the mixture was again cooled to 0° C., and additional N-iodosuccinimide (371 mg) was added. The mixture was then allowed to warm to ambient temperature, diluted with methanol and stirred overnight. The solvent was removed under vacuum, and the residue was dissolved in dichloromethane. The solution was washed with 5% $Na_2CO_3$ and brine, dried ($Na_2SO_4$) and concentrated. The residue was chromatographed on silica gel, eluting with 5–10% methanol in dichloromethane containing 0.5% $NH_4OH$. The product was rechromatographed with 1: 1:0.5 to 3:1;).5 acetone/hexane/NH4OH to give the title compound (260 mg). MS m/e 794 $(M+H)^+$.

Example 3

Compound of Formula (11); R is —$CH_2CH=CH$-(3-quinolyl), $R^p$ is H, W is absent, $R^w$ is H, $R^1$ is H, $R^2$ is $CH_3$ Step 3a. Compound 35 from Scheme 5: R is —$CH_2CH=CH$-(3-quinolyl), $R^p$ is H, W is absent, $R^w$ is H A sample of the compound from Example 2, Step 2f was stirred in methanol overnight. The solvent was removed, and the product was used without further purification.

Step 3b. Compound of formula (II), R is —$CH_2CH=CH$-(3-quinolyl), $R^p$ is H, $R^1$ is H, $R^2$ is $CH_3$, W is absent, $R^w$ is H To a sample of the compound from Step 3a (382 mg, 0.500 mmol) in dry acetonitrile (20 mL) at 0° C. under nitrogen was added N-iodosuccinimide (125 mg, 0.600 mmol), and the mixture was allowed to warm to room temperature. After standing overnight, the mixture was diluted with ethyl acetate. The solution was washed with 5% $Na_2SO_3$, 5% $Na_2CO_3$ and brine, dried ($Na_2SO_4$) and concentrated. The residue was chromatographed on silica gel, eluting with 5–10% methanol in dichloromethane containing 0.5% dimethylamine to give the title compound (201 mg). High Res. M.S. calcd for $C_{41}H_{57}N_3O_{10}$: 752.4122; observed: 752.4145.

Example 4

Compound of Formula (II), R is —$CH_2CH=CH$-(3-quinolyl), $R^p$ is H, W is absent, $R^w$ is H, $R^1$ is acetyl, $R^2$ is $CH_3$ To a sample of the compound from Example 3 (193 mg, 0.260 mmol) in dichloromethane at 0° C. was added triethylamine (0.109 mL, 0.780 mmol). The solution was stirred for 5 minutes, then acetic anhydride ((0.024 mL, 0.260 mmol ) was added, and the mixture was stirred for 2 hours. Another portion of acetic anhydride was added (0.005 mL), then the mixture was stirred at room temperature overnight and at reflux for 30 minutes. The mixture was diluted with ethyl acetate, and this solution was washed with 5% aqueous $Na_2CO_3$ and brine, dried ($Na_2SO_4$) and concentrated. The residue was chromatographed on silica gel, eluting with 5% methanol in dichloromethane containing 0.5% $NH_4OH$ to give the title compound (91.7 mg). MS m/e 794 $(M+H)^+$.

Example 5

Compound of Formula (II); R is —$CH_2CH=CH$-(3-quinolyl), $R^p$ is H, W is absent, $R^w$ is H, $R^1$ is $CH_2C(O)$—O—$CH_2CH_3$, $R^2$ is $CH_3$ To a sample of the compound from Example 3 (120 mg, 0.160 mmol) in acetonitrile was added $NaHCO_3$ (67.2 mg, 0.800 mmol) and ethyl bromoacetate (0.020 mL, 0.180 mmol), and the mixture was stirred under nitrogen at room temperature for 4 days. The mixture was diluted with ethyl acetate, and this solution was washed with 5% aqueous $NaHCO_3$ and brine, dried ($Na_2SO_4$) and concentrated. The residue was chromatographed on silica gel, eluting with 5–10% methanol in dichloromethane containing 0.5% $NH_4OH$ to give the title compound (60 mg). MS m/e 838 $(M+H)^+$.

Example 6

Compound of Formula (II); R is —$CH_2CH=CH$-(3-quinolyl), $R^p$ is H, W is absent, $R^w$ is H, $R^1$ is $CH_2CH=CH_2$, $R^2$ is $CH_3$ To a sample of the compound from Example 3 (120 mg, 0.160 mmol) in acetonitrile was added $NaHCO_3$ (67.2 mg, 0.800 mmol) and allyl bromide (0.016 mL, 0.180 mmol ), and the mixture was stirred under nitrogen at room temperature for 4 days. The mixture was diluted with ethyl acetate, and this solution was washed with 5% aqueous $NaHCO_3$ and brine, dried ($Na_2SO_4$) and concentrated. The residue was chromatographed on silica gel, eluting with 5–10% methanol in dichloromethane containing 0.5% $MH_4OH$ to give the title compound (69 mg). MS mi/e 792 $(M+H)^+$.

Example 7

Compound of Formula (II); R is —$CH_2CH=CH$-(3-quinolyl), $R^p$ is H, W is absent, $R^w$ is H, $R^1$ is $CH_2CH_2F$, $R^2$ is $CH_3$ To a sample of the compound from Example 2 (150 mg, 0.200 mmol) in acetonitrile was added $NaHCO_3$ (84 mg, 1.00 mmol) and 1-bromo-2-fluoroethane (0.016 mL, 0.220 mmol), and the mixture was stirred under nitrogen at room temperature for 4 hours. Another portion of 1-bromo-2-fluoroethane (0.010 mL, 0.100 mmol) was added, then the mixture was stirred at room temperature overnight and at reflux for 2 hours. Another portion of 1-bromo-2-fluoroethane (0.005 mL, 0.050 mmol) was added, then the mixture was stirred at reflux overnight. The mixture was diluted with ethyl acetate, and this solution was washed with 5% aqueous $NaHCO_3$ and brine, dried ($Na_2SO_4$) and concentrated. The residue was chromatographed on silica gel, eluting with 5–10% methanol in dichloromethane containing 0.5 % $NH_4OH$ to give the title compound (73.3 mg). MS m/e 798 $(M+H)^+$.

Example 8

Compound of Formula (II); R is —$CH_2CH$=CH-(3-quinolyl), $R^p$ is H, W is absent, $R^w$ is H, $R^1$ is $CH_2$-phenyl, $R^2$ is $CH_3$ To a sample of the compound from Example 2 (150 mg, 0.200 mmol) in acetonitrile was added $NaHCO_3$ (84 mg, 1.00 mmol) and benzyl bromide (0.020 mL, 0.220 mmol), and the mixture was stirred under nitrogen at room temperature for 48 hours. The mixture was diluted with ethyl acetate, and this solution was washed with 5% aqueous $NaHCO_3$ and brine, dried ($Na_2SO_4$) and concentrated. The residue was chromatographed on silica gel, eluting with 5–10% methanol in dichloromethane containing 0.5% $NH_4OH$ to give the title compound (118 mg). MS m/e 842 $(M+H)^+$.

Example 9

Compound of Formula (II); R is —$CH_2CH$=CH-(3-quinolyl), $R^p$ is H, W is absent, $R^w$ is H, $R^1$ is $CH_2$—CN, $R^2$ is $CH_3$ To a sample of the compound from Example 3 (150 mg, 0.200 mmol) in acetonitrile was added $NaHCO_3$ (84 mg, 1.00 mmol) and bromoacetonitrile (0.015 mL, 0.220 mmol), and the mixture was stirred under nitrogen at room temperature for 48 hours. The mixture was diluted with ethyl acetate, and this solution was washed with 5% aqueous $NaHCO_3$ and brine, dried ($Na_2SO_4$) and concentrated. The residue was chromatographed on silica gel, eluting with 5–10% methanol in dichloromethane containing 0.5% $NH_4OH$ to give the title compound (106.7 mg). MS m/e 791 $(M+H)^+$.

Example 10

Compound of Formula (II); R is —$CH_2CH$=CH-(3-quinolyl), $R^p$ is H, W is absent, $R^w$ is H, $R^1$ is $CH_2$—C≡CH, $R^2$ is $CH_3$ To a sample of the compound from Example 3 (150 mg, 0.200 mmol) in acetonitrile was added $NaHCO_3$ (84 mg, 1.00 mmol) and propargyl bromide (80% in toluene, 0.026 mL, 0.220 mmol), and the mixture was stirred under nitrogen at room temperature for 48 hours. The mixture was diluted with ethyl acetate, and this solution was washed with 5% aqueous $NaHCO_3$ and brine, dried ($Na_2SO_4$) and concentrated. The residue was chromatographed on silica gel, eluting with 5% methanol in dichloromethane containing 0.5% $NH_4OH$ to give the title compound (90 mg). MS m/e 790 $(M+H)^+$.

Example 11

Compound of Formula (H); R is —$CH_2CH$=CH-(3-quinolyl), $R^p$ is H, W is absent, $R^w$ is H, $R^1$ is $CH_2CH_2CH_3$, $R^2$ is $CH_3$ To a sample of the compound from Example 3 (150 mg, 0.200 mmol) in acetonitrile was added $NaHCO_3$ (84 mg, 1.00 mmol) and 1-bromopropane (0.020 mL, 0.220 mmol), and the mixture was stirred under nitrogen at room temperature for 48 hours and at 60° C. for 16 hours. The mixture was diluted with ethyl acetate, and this solution was washed with 5% aqueous $NaHCO_3$ and brine, dried ($Na_2SO_4$) and concentrated. The residue was chromatographed on silica gel, eluting with 5% methanol in dichloromethane containing 0.5% $NH_4OH$ to give the title compound (80 mg). MS m/e 794 $(M+H)^+$.

Example 12

Compound of Formula (II); R is —$CH_2CH$=CH-(3-quinolyl), $R^p$ is H, W is absent, $R^w$ is H, $R^1$ is $CH_2$-cyclopropyl, $R^2$ is $CH_3$ To a sample of the compound from Example 3 (150 mg, 0.200 mmol) in acetonitrile was added $NaHCO_3$ (84 mg, 1.00 mmol) and (bromomethyl)cyclopropane (0.021 mL, 0.220 mmol), and the mixture was stirred under nitrogen at room temperature for 48 hours. The mixture was diluted with ethyl acetate, and this solution was washed with 5% aqueous $NaHCO_3$ and brine, dried ($Na_2SO_4$) and concentrated. The residue was chromatographed on silica gel, eluting with 5% methanol in dichloromethane containing 0.5% $NH_4OH$ to give the title compound (90.5 mg). MS m/e 806 $(M+H)^+$.

Example 13

Compound of Formula (II); R is —$CH_2CH$=CH-(3-quinolyl), $R^p$ is H, W is absent, $R^w$ is H, $R^1$ is cyclopropyl, $R^2$ is $CH_3$ To a sample of the compound from Example 3 (150 mg, 0.200 mmol) in methanol was added acetic acid (0.114 mL, 2.00 mmol) and ((1-ethoxycyclopropyl)oxy)trimethylsilane (0.200 mL, 1.00 mmol), and the mixture was stirred under nitrogen. $NaBH_3CN$ (63 mg, 1.00 mmol) was added under nitrogen, and the mixture was stirred at room temperature for 2 hours and at reflux for 12 hours. The mixture was diluted with ethyl acetate, and this solution was washed with 5% aqueous $Na_2CO_3$ and brine, dried ($Na_2SO_4$) and concentrated. The residue was chromatographed on silica gel, eluting with 5% methanol in dichloromethane containing 0.5% $NH_4OH$ to give the title compound (54.4 mg). MS m/e 792 $(M+H)^+$.

Example 14

Compound of Formula (II); R is —$CH_2CH$=CH-(3-quinolyl), $R^p$ is H, W is absent, $R^w$ is H, $R^1$ is $CH_2$-(3-pyridyl), $R^2$ i s $CH_3$ To a sample of the compound from Example 3 (150 mg, 0.200 mmol) in methanol was added acetic acid (0. 114 mL, 2.00 mmol) and 3-pyridine carboxaldehyde (0.094 mL, 1.00 mmol), and the mixture was stirred at 0° C. under nitrogen. $NaBH_3CN$ (63 mg, 1.00 mmol) was added under nitrogen, and the mixture was allowed to warm to room temperature anid stirred for 6 hours. The mixture was diluted with ethyl acetate, and this solution was washed with 5% aqueous $Na_2CO_3$ and brine, dried ($Na_2SO_4$) and concentrated. The residue was chromatographed on silica gel, eluting with 5% methanol in dichloromethane containing 0.5% $NH_4OH$ to give the title compound (132 mg). MS m/e 843 $(M+H)^+$.

Example 15

Compound of Formula (II); R is —$CH_1CH$=CH-(3-quinolyl), $R^p$ is H, W is absent, $R^w$ is H, $R^1$ is $CH_2$-(cyclo-$C_3H_5$), $R^2$ is $CH_3$ A solution of a sample of Example 1 (150 mg, 0.20 mmol) in acetonitrile (2 mL) at room temperature under $N_2$ was treated sequentially with NaHCO$_3$ (84 mg, 1.1I mmol) and (bromomethyl)cyclopropane (21 μL, 0.22 mmol), stirred at room temperature for 18 hours, treated with an additional equivalent of (bromomethyl)cyclopropane, stirred for 18 hours, treated with N,N-diisopropylethylamine (174 μL, 1.1 mmol) and an additional 2 equivalents of (bromomethyl) cyclopropane, stirred for 4 days, diluted with ethyl acetate (10 mL), washed sequentially with 5% NaHCO$_3$ and brine, dried (Na$_2$SO$_4$), filtered, and concentrated. The residue was purified by column chromatography on silica gel with 1% methanol in methylene chloride containing I% ammonium hydroxide to provide 90.5 mg of the desired compound as a white solid. MS (ESI(+)) 806 (M+H)$^+$.

Example 16

Compound of Formula (II); R is —CH$_2$CH=CH-(3-quinolyl), R$^P$ is H, W is absent, R$^w$ is H, R$^1$ is CH$_2$CH$_2$CH$_3$, R$^2$ is CH$_3$ A solution of a sample of Example 1(150 mg, 0.20 mmol) in acetonitrile (2 mL) at room temperature under N$_2$ was treated sequentially with NaHCO$_3$ (84 mg, 1.1 mmol) and 1-bromopropane (20 μL, 0.22 mmol), stirred at room temperature for 18 hours, treated with an additional equivalent of 1-bromopropane, stirred for 18 hours, treated with N,N-diisopropylethylamine (174 μL, 1.1 mmol), warmed to 60° C. for 18 hours, cooled to room temperature, treated with an additional 2 equivalents of 1-bromopropane, diluted with ethyl acetate (10 mL), washed sequentially with 5% NaHCO$_3$ and brine, dried (Na$_2$SO$_4$), filtered, and concentrated. The residue was purified by column chromatography on silica gel with 1% methanol in methylene chloride containing 1% ammonium hydroxide to provide 80 mg of the desired compound as a white solid. MS (ESI(+)) 794 (M+H)$^+$.

Example 17

Compound of Formula (II); R is —CH$_2$CH=CH-(3-quinolyl), R$^P$ is H, W is absent, R$^w$ is H, R$^1$ is CH$_2$CH=CHC$_6$H$_5$, R$^2$ is CH$_3$ A solution of a sample of Example 1 (260.64 mg, 0.33 mmol) in acetonitrile (2 mL) at room temperature under N$_2$ was treated with K$_2$CO$_3$ (230 mg, 1.1 mmol) and cinnamyl bromide (55.5 μL, 0.37 mmol), stirred at room temperature for 48 hours, diluted with ethyl acetate (10 mL), washed sequentially with 5% NaHCO$_3$ and brine, dried (Na$_2$SO$_4$), filtered, and concentrated. The residue was purified by column chromatography on silica gel with 5% methanol in methylene chloride containing 1% ammonium hydroxide to provide 180 mg of the desired compound as a white solid. MS (ESI(+)) 869 (M+H)$^+$.

Example 18

Compound of Formula (II); R is —CH$_2$CH=CH-(3-quinolyl), R$^P$ is H, W is absent, R$^w$ is H, R$^1$ is CH$_2$C(=CH$_2$)C(O)OCH$_3$, R$^2$ is CH$_3$ A solution of a sample of Example 1 (260.64 mg, 0.33 mmol) in acetonitrile (2 mL) at room temperature under N$_2$ was treated with K$_2$CO$_3$ (230 mg, 1.1 mmol) and methyl-2-(bromomethyl)acrylate (45.08 μL), stirred at room temperature for 48 hours, diluted with ethyl acetate, washed sequentially with 5% NaHCO$_3$ and brine, dried (Na$_2$SO$_4$), filtered, and concentrated. The residue was purified by column chromatography on silica gel with 5% methanol in methylene chloride containing 1% ammonium hydroxide to provide 233 mg of the desired compound as a white solid. MS (ESI(+)) 850 (M+H)$^+$.

Example 19

Compound of Formula (II); R is —CH$_2$CH=CH-(3-quinolyl), R$^P$ is H, W is absent, R$^w$ is H, R$^1$ is CH$_2$C(=CH$_2$)CH$_3$, R$^2$ is CH$_3$ A solution of a sample of Example 1 (260.64 mg, 0.33 mmol) in acetonitrile (2 mL) at at room temperature under N$_2$ was treated with K$_2$CO$_3$ (230 mg, 1.1 mmol) and 3-bromo-2-methylpropene (37.81 μL), stirred at room temperature for 48 hours, diluted with ethyl acetate, washed sequentially with 5% NaHCO$_3$ and brine, dried (Na$_2$SO$_4$), filtered, and concentrated. The residue was purified by column chromatography on silica gel with 5% methanol in methylene chloride containing 1% ammonium hydroxide to provide 176.4 mg of the desired compound as a white solid. MS (ESI(+)) 804 (M+H)$^+$.

Example 20

Compound of Formula (II); R is —CH$_2$CH=CH-(3-quinolyl), R$^P$ is H, W is absent, R$^w$ is H, R$^1$ is cyclo-C$_3$H$_5$, R$^2$ is CH$_3$ A solution of a sample of Example 1 (1 50mg, 0.200 mmol) in methanol (5 mL) at room temperature under N$_2$ was treated sequentially with acetic acid (114 μL, 2.00 mmol), [(1-ethyoxycyclopropyl)oxy]trimethylsilane (200 μL, 1.00 mmol), and NaBH$_3$CN (63 mg, 1.00 mmol), stirred at room temperature for two hours, heated to reflux for 12 hours, diluted with ethyl acetate (30 mL), washed sequentially with 5% Na$_2$CO$_3$ and brine, dried (Na$_2$SO$_4$), filtered, and concentrated. The residue was purified by column chromatography on silica gel with a gradient of 2% methanol in methylene chloride to 5% methanol in methylene chloride containing 1% ammonium hydroxide to provide 54.4 mg of the desired compound as a white solid. MS (ESI(+)) 792 (M+H)$^+$. HRMS (ESI(+)) m/z calcd for C$_{44}$H$_{61}$N$_3$O$_{10}$: 814.4249 (M+Na)$^+$. Found 814.4243.

Example 21

Compound of Formula (II); R is —CH$_2$CH=CH-(3-quinolyl), R$^P$ is H, W is absent, R$^w$ is H, R$^1$ is CH$_2$-(3-pyridyl), R$^2$ is CH$_3$ A solution of a sample of Example 1 in methanol (5 mL) at 0° C. under N$_2$ was treated sequentially with acetic acid (114 μL, 2.00 mmol), 3-pyridinecarboxaldehyde (94 μL, 1.00 mmol), and sodium cyanoborohydride (63 mg 1.00 mmol), warmed to room temperature with stirring over 18 hours, diluted with ethyl acetate (30 mL), washed sequentially with 5% Na$_2$CO$_3$, 2% tris(hydroxymethyl) aminomethane, and brine, dried (Na$_2$SO$_4$), filtered, and concentrated. The residue was purified by column chromatography on silica gel with 5% methanol in methylene chloride containing 1% ammonium hydroxide to provide 132 mg (78%) of the desired compound as an off-white foam.

MS (APCI) 843 (M+H)+.

HRMS (ESI(+)) m/z calcd for C$_{47}$H$_{63}$N$_4$O$_{10}$: 843.4544 (M+H)$^+$. Found: 843.4562.

Anal. calcd for: C, 66.96; H, 7.41, N, 6.65. Found C, 66.97; H, 7.45; N, 6.57.

Example 22

Compound of Formula (II); R is —CH$_2$CH=CH-(3-quinolyl), R$^P$ is H, W is absent, R$^w$ is H, R$^1$ is CH$_2$-(3-hydroxyphenyl), R$^2$ is CH$_3$ A solution of a sample of Example 1 (150 mg, 0.200 mmol) in methanol (5 mL) at 0 ° C. under N$_2$ was treated with 3-hydroxybenzaldehyde (122 mg, 1.0 mmol), stirred for 5–10 minutes, treated with acetic acid (114 μL, 2.00 mmol), stirred at 0° C. for 10–15 minutes, treated with sodium cyanoborohydride (63 mg, 1.00 mmol), warmed to room temperature over 18 hours, stirred for 48 hours, treated with ethyl acetate (20 mL), washed sequentially with 5% $NaHCO_3$, 2% tris(hydroxymethyl)aminomethane, and brine. If any aqueous extract was too basic (pH 10–12) and contained product, it was treated with $NH_4Cl$ and back-extracted with ethyl acetate. The combined organic extracts were washed with brine, dried ($Na_2SO_4$), filtered, and concentrated. The residue was purified by column chromatography on silica gel with a gradient of 5% methanol in methylene chloride containing 1% ammonium hydroxide to provide to provide 97.1 mg of the desired compound as a yellow solid. MS (ESI(+)) m/z 858 (M+H)+.

Example 23

Compound of Formula (II); R is —$CH_2CH=CH$-(3-quinolyl), $R^P$ is H, W is absent, $R^w$ is H, $R^1$ is $CH_2$-(2-hydroxy-3-tert-butyl-5-methylphenyl), $R^2$ is $CH_3$ A solution of a sample of Example 1 (28 mg, 0.037 mmol) and 3-tert-butyl-5-methylphenol (1.5–2.0 equivalents) in toluene (1 mL) in a 1 dram vial was treated with paraformaldehyde (2 equivalents), warmed to 90° C. for 18 hours, and concentrated. If necessary, the vial was uncapped and warmed to permit the toluene to evaporate and drive the reaction to completion. The residue was purified by column chromatography on silica gel with acetone to provide the desired product.

MS (ESI(+)) m/z 928 (M+H)+.

Example 24

Compound of Formula (II); R is —$CH_2CH=CH$-(3-quinolyl), $R^P$ is H, W is absent, $R^w$ is H, $R^1$ is $CH_2$-(2-hydroxy-3,4-dimethylphenyl), $R^2$ is $CH_3$ A sample of Example 1, paraformaldehyde, and 3,4-dimethylphenol were processed as described in Example 9 to provide the desired compound. MS (ESI(+)) m/z 886 (M+H)+.

Example 25

Compound of Formula (II); R is —$CH_2CH=CH$-(3-quinolyl), $R^P$ is H, W is absent, $R^w$ is H, $R^1$ is $CH_2$-(2-hydroxy-3-methoxy-5-(2-propenyl)phenyl), $R^2$ is $CH_3$ A sample of Example 1 (28 mg, 0.037 mmol), paraformaldehyde, and 3-allyl-5-methoxyphenol were processed as described in Example 9 to provide the desired compound.

MS (ESI(+)) m/z 928 (M+H)+.

Example 26

Compound of Formula (II); R is —$CH_2CH=CH$-(3-quinolyl), $R^P$ is H, W is absent, $R^w$ is H, $R^1$ is $CH_2$-(2-hydroxy-3-methoxy-5-methylphenyl), $R^2$ is $CH_3$ A sample of Example 1 (28 mg, 0.037 mmol), paraformaldehyde, and 3-methoxy-5-methylphenol were processed as described in Example 9 to provide the desired compound.

MS (ESI(+)) m/z 902 (M+H)+.

Example 27

Compound of Formula (II); R is —$CH_2CH=CH$-(3-quinolyl), $R^P$ is H, W is absent, $R^w$ is H, $R^1$ is $CH_2$-(2-hydroxy-5-cyclopentylphenyl), $R^2$ is $CH_3$ A sample of Example 1 (28 mg, 0.037 mmol), paraformaldehyde, and 3-cyclopentylphenol were processed as described in Example 9 to provide the desired compound.

MS (ESI(+)) m/z 926 (M+H)+.

Example 28

Compound of Formula (II); R is —$CH_2CH=CH$-(3-quinolyl), $R^P$ is H, W is absent, $R^w$ is H, $R^1$ is $CH_2$-(2-hydroxy-5-carboxamidophenyl), $R^2$ is $CH_2$ A sample of Example 1 (28 mg, 0.037 mmol), paraformaldehyde, and 3-hydroxybenzamide were processed as described in Example 9 to provide the desired compound.

MS (ESI(+)) m/z 901 (M+H)+.

Example 29

Compound of Formula (II); R is —$CH_2CH=CH$-(3-quinolyl), $R^P$ is H, W is absent, $R^w$ is H, $R^1$ is is $CH_2$-(2-hydroxy-3-methoxy-5-(2-methoxycarbonylethyl)phenyl), $R^2$ is $CH_3$ A sample of Example 1 (28 mg, 0.037 mmol), paraformaldehyde, and 3-(3-hydroxyphenyl)-propionic acid methyl ester were processed as described in Example 9 to provide the desired compound.

MS (ESI(+)) m/z 944 (M+H)+.

Example 30

Compound of Formula (II); R is —$CH_2CH=CH$-(3-quinolyl), $R^P$ is H, W is absent, $R^w$ is H, $R^1$ is $CH_2$-(2-hydroxy-3-methyl-5-fluorophenyl), $R^2$ is $CH_3$ A sample of Example 1 (28 mg, 0.037 mmol), paraformaldehyde, and 3-fluoro-5-methylphenol were processed as described in Example 9 to provide the desired compound.

MS (ESI(+)) m/z 890 (M+H)+.

Example 31

Compound of Formula (II); R is —$CH_2CH=CH$-(3-quinolyl), $R^P$ is H, W is absent, $R^w$ is H, $R^1$ is $CH_2$-(2-hydroxy-3-methoxy-5-acetylphenyl), $R^2$ is $CH_3$ A sample of Example 1 (28 mg, 0.037 mmol), paraformaldehyde, and 1-(3-hydroxy-5-methoxy-phenyl)ethanone were processed as described in Example 9 to provide the desired compound.

MS (ESI(+)) m/z 930 (M+H)+.

Example 32

Compound of Formula (II); R is —$CH_2CH=CH$-(3-quinolyl), $R^P$ is H, W is absent, $R^w$ is H, $R^1$ is $CH_2$-(2-hydroxy-3-bromophenyl), $R^2$ is $CH_3$ A sample of Example 1 (28 mg, 0.037 mmol), paraformaldehyde, and 3-bromophenol were processed as described in Example 9 to provide the desired compound.

MS (ESI(+)) m/z 936 (M+H)+.

Example 33

Compound of Formula (II); R is —CH$_2$CH=CH-(3-quinolyl), R$^p$ is H, W is absent, R$^w$ is H, R$^1$ is CH$_2$-(2-hydroxy-3-methoxy-5-alkoxycarbonylphenyl), R$^2$ is CH$_3$ A sample of Example 1 (28 mg, 0.037 mmol), paraformaldehyde, and 3-hydroxy-5-methoxybenzoic acid methyl ester were processed as described in Example 9 to provide the desired compound.

MS (ESI(+)) m/z 946 (M+H)$^+$.

Example 34

Compound of Formula (II); R is —CH$_2$CH=CH-(3-quinolyl), R$^p$ is H, W is absent, R$^w$ is H, R$^1$ is CH$_2$-(2-hydroxy-3-ethylphenyl), R$^2$ is CH$_3$ A sample of Example 1 (28 mg, 0.037 mmol), paraformaldehyde, and 3-ethylphenol were processed as described in Example 9 to provide the desired compound.

MS (ESI(+)) m/z 886 (M+H)$^+$.

Example 35

Compound of Formula (II); R is —CH$_2$CH=CH-(3-quinolyl), R$^p$ is H, W is absent, R$^w$ is H, R$^1$ is CH$_2$-(2-hydroxy-5-isobutylphenyl), R$^2$ is CH$_3$ A sample of Example 1 (28 mg, 0.037 mmol), paraformaldehyde, and 3-sec-butylphenol were processed as described in Example 9 to provide the desired compound.

MS (ESI(+)) m/z 914 (M+H)$^+$.

Example 36

Compound of Formula (II); R is —CH$_2$CH=CH-(3-quinolyl), R$^p$ is H, W is absent, R$^w$ is H, R$^1$ is CH$_2$-(2-hydroxy-3-methyl-5-diethylamino-6-methylphenyl), R$^2$ is CH$_3$ A sample of Example 1 (28 mg, 0.037 mmol), paraformaldehyde, and 3-diethylaminomethyl-2,5-dimethylphenol were processed as described in Example 9 to provide the desired compound.

MS (ESI(+)) m/z 971 (M+H)$^+$.

Example 37

Compound of Formula (II); R is —CH$_2$CH=CH-(3-quinolyl), R$^p$ is H, W is absent, R$^w$ is H, R$^1$ is CH$_2$-(2-hydroxy-4-methyl-5-bromo-6-methylphenyl), R$^2$ is CH$_3$ A sample of Example 1 (28 mg, 0.037 mmol), paraformaldehyde, and 3-bromo-2,4-dimethylphenol were processed as described in Example 9 to provide the desired compound.

MS (ESI(+)) m/z 964 (M+H)$^+$.

Example 38

Compound of Formula (II); R is —CH$_2$CH=CH-(3-quinolyl), R$^p$ is H, W is absent, R$^w$ is H, R$^1$ is CH$_2$-(2-hydroxy-3-hydroxymethylphenyl), R$^2$ is CH$_3$ A sample of Example 1 (28 mg, 0.037 mmol), paraformaldehyde, and 3-hydroxymethylphenol were processed as described in Example 9 to provide the desired compound.

What is claimed is:

1. A compound selected from the group consisting of

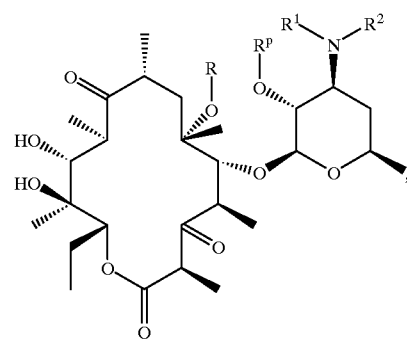
(I)

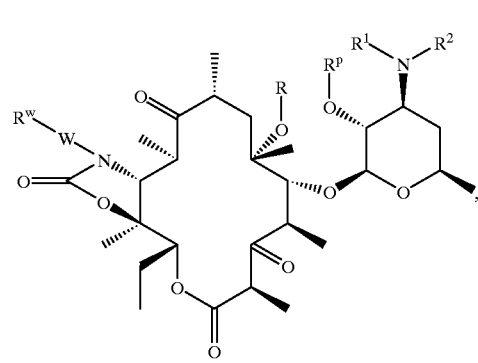
(II)

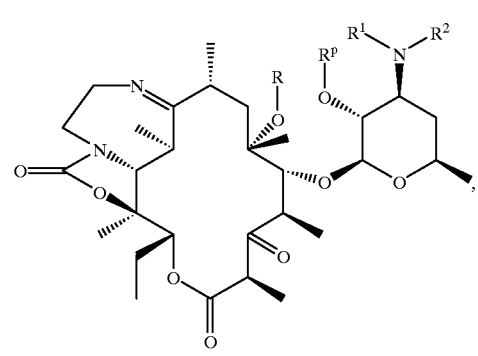
(III)

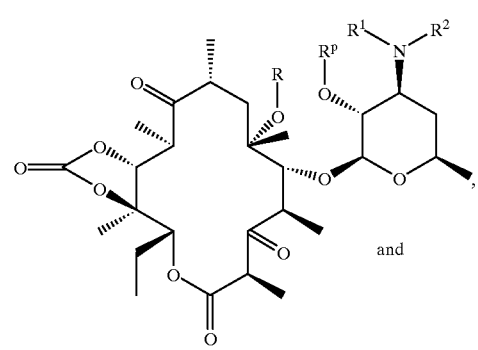
(IV)

and

-continued

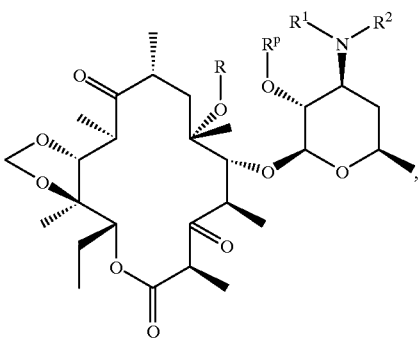

(V)

or a pharmaceutically acceptable salt, ester or prodrug thereof, wherein $R^1$ and $R^2$, with the proviso that $R^1$ and $R^2$ are not both methyl, are independently selected from the group consisting of
(1) hydrogen,
(2) $C_1$–$C_6$-alkyl optionally substituted with a substituent selected from the group consisting of
  (a) halogen,
  (b) $C_3$–$C_6$-cycloalkyl,
  (c) aryl,
  (d) substituted aryl,
  (e) heteroaryl,
  (f) substituted heteroaryl,
  (g) —CHO,
  (h) —C(O)—$C_1$–$C_6$-alkyl, and
  (i) —C(O)—NR'R", wherein R' and R" are independently selected from the group consisting of hydrogen, $C_1$–$C_3$-alkyl, $C_1$–$C_3$-alkyl substituted with aryl, substituted aryl, heteroaryl, and substituted heteroaryl,
(3) $C_2$–$C_6$-alkyl optionally substituted with a substituent selected from the group consisting of
  (a) $C_1$–$C_6$-alkoxy,
  (b) —NR'R", wherein R' and R" are as previously defined,
  (c) —NH—C(O)—$C_1$–$C_6$-alkyl,
  (d) —NH—C(O)—O—$C_1$–$C_6$-alkyl,
  (e) —O—C(O)—O—$C_1$–$C_6$-alkyl,
  (f) —O—C(O)—$C_1$–$C_6$-alkyl,
  (g) —CH(=N—O—$C_1$–$C_6$-alkyl),
  (h) —C(=N—O—$C_1$–$C_6$-alkyl)—$C_1$–$C_6$-alkyl,
  (i) —CH(=N—NH—$C_1$–$C_6$-alkyl), and
  (j) —C(=N—NH—$C_1$–$C_6$-alkyl)—$C_1$–$C_6$-alkyl,
(4) $C_3$–$C_6$-alkenyl optionally substituted with a substituent selected from the group consisting of
  (a) halogen,
  (b) $C_3$–$C_6$-cycloalkyl,
  (c) aryl,
  (d) substituted aryl,
  (e) heteroaryl,
  (f) substituted heteroaryl,
  (g) —NH—C(O)—$C_1$–$C_6$-alkyl,
  (h) —NH—C(O)—O—$C_1$–$C_6$-alkyl,
  (i) —O—C(O)—O—$C_1$–$C_6$-alkyl,
  (j) —O—C(O)—$C_1$–$C_6$-alkyl,
  (k) —CHO,
  (l) —C(O)—$C_1$–$C_6$-alkyl,
  (m) —C(O)—NR'R", wherein R' and R" are as previously defined,
  (n) —CH(=N—O—$C_1$–$C_6$-alkyl),
  (o) —C(=N—O—$C_1$–$C_6$-alkyl)—$C_1$–$C_6$-alkyl,
  (p) —CH(=N—NH—$C_1$–$C_6$-alkyl),
  (q) —C(=N—NH—$C_1$–$C_6$-alkyl)—$C_1$–$C_6$-alkyl, and
  (r) —C(O)—O—$C_1$–$C_6$-alkyl,
(5) $C_3$–$C_6$-alkynyl optionally substituted with a substituent selected from the group consisting of
  (a) halogen,
  (b) $C_3$–$C_6$-cycloalkyl,
  (c) aryl,
  (d) substituted aryl,
  (e) heteroaryl, and
  (f) substituted heteroaryl,
(6) $C_3$–$C_6$-cycloalkyl,
(7) —CHO,
(8) —C(O)—$C_1$–$C_6$-alkyl,
(9) —C(O)—NR'R", wherein R' and R" are as previously defined, and
(10) —C(O)—O—$C_1$–$C_6$-alkyl, or $R^1$ and $R^2$ taken together may be —$(CH_2)_p$—, wherein p is 3-to-7, which taken together with the nitrogen atom to which they are attached, thus form a heterocyclic ring containing one nitrogen atom and from 3 to 7 carbon atoms;

R is selected from the group consisting of
(1) methyl substituted with a substituent selected from the group consisting of
  (a) —CN,
  (b) —F,
  (c) —$CO_2R^3$ wherein $R^3$ is $C_1$–$C_3$-alkyl, aryl-substituted $C_1$–$C_3$-alkyl, or heteroaryl-substituted $C_1$–$C_3$-alkyl,
  (d) —$S(O)_n$—$R^3$ wherein n is 0, 1, or 2, and $R^3$ is as previously defined,
  (e) —NH—C(O)—$R^3$ where $R^3$ is as previously defined,
  (f) —NH—C(O)—$NR^4R^5$ wherein $R^4$ and $R^5$ are independently selected from the group consisting of
    (i) hydrogen,
    (ii) $C_1$–$C_3$-alkyl,
    (iii) $C_1$–$C_3$-alkyl substituted with aryl,
    (iv) $C_1$–$C_3$-alkyl substituted with substituted aryl,
    (v) $C_1$–$C_3$-alkyl substituted with heteroaryl, and
    (vi) $C_1$–$C_3$-alkyl substituted with and substituted heteroaryl,
  (g) aryl,
  (h) substituted aryl,
  (i) heteroaryl, and
  (j) substituted heteroaryl,
(2) $C_2$–$C_{10}$-alkyl,
(3) $C_2$–$C_{10}$-alkyl substituted with one or more substituents selected from the group consisting of
  (a) halogen,
  (b) hydroxy,
  (c) $C_1$–$C_3$-alkoxy,
  (d) $C_1$–$C_3$-alkoxy-$C_1$–$C_3$-alkoxy,
  (e) oxo,
  (f) —$N_3$,
  (g) —CHO,
  (h) —O—SO2-(substituted $C_1$–$C_6$-alkyl),
  (i) —$NR^6R^7$ wherein $R^6$ and $R^7$ are selected from the group consisting of
    (i) hydrogen,
    (ii) $C_1$–$C_{12}$-alkyl,
    (iii) substituted $C_1$–$C_{12}$-alkyl,
    (iv) $C_1$–$C_{12}$-alkenyl, (v) substituted $C_1$–$C_{12}$-alkenyl,
(vi) $C_1$–$C_{12}$-alkynyl,
(vii) substituted $C_1$–$C_{12}$-alkynyl,
(viii) aryl,
(ix) $C_3$–$C_8$-cycloalkyl,
(x) substituted $C_3$–$C_8$-cycloalkyl,
(xi) substituted aryl,
(xii) heterocycloalkyl,
(xiii) substituted heterocycloalkyl,
(xiv) $C_1$–$C_{12}$-alkyl substituted with aryl,
(xv) $C_1$–$C_{12}$-alkyl substituted with substituted aryl,
(xvi) $C_1$–$C_{12}$-alkyl substituted with heterocycloalkyl,
(xvii) $C_1$–$C_{12}$-alkyl substituted with substituted heterocycloalkyl,
(xviii) $C_1$–$C_{12}$-alkyl substituted with $C_3$–$C_8$-cycloalkyl,
(xix) $C_1$–$C_{12}$-alkyl substituted with substituted $C_3$–$C_8$-cycloalkyl,
(xx) heteroaryl,
(xxi) substituted heteroaryl,
(xxii) $C_1$–$C_{12}$-alkyl substituted with heteroaryl, and
(xxiii) $C_1$–$C_{12}$-alkyl substituted with substituted heteroaryl, or $R^6$ and $R^7$ are taken together with the atom to which they are attached form a 3–10 membered heterocycloalkyl ring which may be substituted with one or more substituents independently selected from the group consisting of
(i) halogen,
(ii) hydroxy,
(iii) $C_1$–$C_3$-alkoxy, (iv) $C_1$–$C_3$-alkoxy-$C_1$–$C_3$-alkoxy,
(v) oxo,
(vi) $C_1$–$C_3$-alkyl,
(vii) halo-$C_1$–$C_3$-alkyl, and
(vii) $C_1$–$C_3$-alkoxy-$C_1$–$C_3$-alkyl,
(j) —$CO_2R^3$ wherein $R^3$ is as previously defined,
(k) —C(O)—$NR^4R^5$ wherein $R^4$ and $R^5$ are previously defined,
(l) =N—O—$R^3$ wherein $R^3$ is as previously defined,
(m) —C≡N,
(n) —O—S(O)$_n$—$R^3$ wherein n and $R^3$ are as previously defined,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl,
(u) $C_1$–$C_{12}$-alkyl substituted with heteroaryl,
(v) heterocycloalkyl,
(w) substituted heterocycloalkyl,
(x) —NH—C(O)—$R^3$ where $R^3$ is as previously defined,
(y) —NH—C(O)—$NR^4R^5$ wherein $R^4$ and $R^5$ are as previously defined,
(z) =N—$NR^6R^7$ wherein $R^6$ and $R^7$ are as previously defined,
(aa) =N—$R^3$ wherein $R^3$ is as previously defined,
(bb) =N—NH—C(O)—$R^4$ wherein $R^4$ is as previously defined, and
(cc) =N—NH—C(O)—$NR^4R^5$ wherein $R^4$ and $R^5$ are as previously defined, (4) $C_3$-alkenyl substituted with a moiety selected from the group consisting of
(a) halogen,
(b) —CHO,
(c) —$CO_2R^3$ where $R^3$ is as previously defined,
(d) —C(O)—$R^4$ where $R^4$ is as previously defined,
(e) —C(O)—$NR^4R^5$ wherein $R^4$ and $R^5$ are as previously defined,
(f) —C≡N,
(g) aryl,
(h) substituted aryl,
(i) heteroaryl,
(j) substituted heteroaryl,
(k) $C_3$–$C_7$-cycloalkyl, and
(l) $C_1$–$C_{12}$-alkyl substituted with heteroaryl,
(5) $C_4$–$C_{10}$-alkenyl,
(6) $C_4$–$C_{10}$-alkenyl substituted with one or more substituents selected from the group consisting of
(a) halogen,
(b) $C_1$–$C_3$-atkoxy,
(c) oxo,
(d) —CHO,
(e) —$CO_2R^3$ where $R^3$ is as previously defined,
(f) —C(O)—$NR^4R^5$ wherein $R^4$ and $R^5$ are as previously defined,
(g) —$NR^6R^7$ wherein $R^6$ and $R^7$ are as previously defined,
(h) =N—O—$R^3$ wherein $R^3$ is as previously defined,
(i) —C≡N,
(j) —O—S(O)$_n$—$R^3$ wherein n is 0, 1, or 2 and $R^3$ is as previously defined,
(k) aryl,
(l) substituted aryl,
(m) heteroaryl,
(n) substituted heteroaryl,
(o) $C_3$–$C_7$-cycloalkyl,
(p) $C_1$–$C_{12}$-alkyl substituted with heteroaryl,
(q) —NH—C(O)—$R^3$ where $R^3$ is as previously defined,
(r) —NH—C(O)—$NR^4R^5$ wherein $R^4$ and $R^5$ are as previously defined,
(s) =N—$NR^6R^7$ wherein $R^6$ and $R^7$ are previously defined,
(t) =N—$R^3$ wherein $R^3$ is as previously defined,
(u) =N—NH—C(O)—$R^3$ where $R^3$ is as previously defined, and
(v) =N—NH—C(O)—$NR^4R^5$ wherein $R^4$ and $R^5$ are as previously defined,
(7) $C_3$–$C_{10}$-alkynyl, and
(8) $C_3$–$C_{10}$-alkynyl substituted with one or more substituents selected from the group consisting of
(a) trialkylsilyl,
(b) aryl,
(c) substituted aryl,
(d) heteroaryl, and
(e) substituted heteroaryl,
with the proviso that when R is allyl and $R^1$ is methyl, $R^2$ is not H;
$R^p$ is hydrogen or a hydroxy protecting group;
$R^w$ is selected from the group consisting of
(1) hydrogen,
(2) $C_1$–$C_6$-alkyl, optionally substituted with one or more substituents selected from the group consisting of
(a) aryl,
(b) substituted aryl, (c) heteroaryl,
(d) substituted heteroaryl,
(3) a group selected from option (2) as previously defined further substituted with —$CH_2$—M—$R^8$, wherein M is selected from the group consisting of
(i) —O—,
(ii) —NH—,
(ii) —N($CH_3$)—,
(iv) —S(O)$_n$—, wherein n is as described previously,
(v) —NH—C(O)—, and
(vi) —C(O)—NH—, and
$R^8$ is selected from the group consisting of
(i) —($CH_2$)$_n$-aryl, wherein n is as described previously,
(ii) —($CH_2$)$_n$-substituted aryl, wherein n is as described previously,
(iii) —($CH_2$)$_n$-heteroaryl, wherein n is as described previously,
(iv) —($CH_2$)$_n$-substituted heteroaryl, wherein n is as described previously, and
(v) —($CH_2$)$_n$-heterocycloalkyl, wherein n is as described previously; and
W is absent or is selected from the group consisting of —O—, —NH— and —N($CH_3$)—.

2. A compound according to claim 1 which is selected from the group consisting of Compound of Formula (I), R is —$CH_2$CH=CH-(3-quinolyl), $R^p$ is H, $R^1$ is methyl, $R^2$ is hydrogen;

Compound of formula (II), R is —$CH_2$CH=CH-(3-quinolyl), $R^p$ is acetyl, $R^1$ is H, $R^2$ is $CH_3$, W is absent, $R^w$ is H;

Compound of Formula (II); R is —$CH_2$CH=CH-(3-quinolyl), $R^p$ is H, W is absent, $R^w$ is H, $R^1$ is H, $R^2$ is $CH_3$;

Compound of Formula (II); R is —$CH_2$CH=CH-(3-quinolyl), $R^p$ is H, W is absent, $R^w$ is H, $R^1$ is acetyl, $R^2$ is $CH_3$;

Compound of Formula (II); R is —$CH_2$CH=CH-(3-quinolyl), $R^p$ is H, W is absent, $R^w$ is H, $R^1$ is $CH_2$C(O)-O—$CH_2$$CH_3$, $R^2$ is $CH_3$;

Compound of Formula (II); R is —$CH_2$CH=CH-(3-quinolyl), $R^p$ is H, W is absent, $R^w$ is H, $R^1$ is $CH_2$CH=$CH_2$, $R^2$ is $CH_3$;

Compound of Formula (II); R is —$CH_2$CH=CH-(3-quinolyl), $R^p$ is H, W is absent, $R^w$ is H, $R^1$ is $CH_2$$CH_2$F, $R^2$ is $CH_3$;

Compound of Formula (II); R is —$CH_2$CH=CH-(3-quinolyl), $R^p$ is H, W is absent, $R^w$ is H, $R^1$ is $CH_2$-phenyl, $R^2$ is $CH_3$;

Compound of Formula (II); R is —$CH_2$CH=CH-(3-quinolyl), $R^p$ is H, W is absent, $R^w$ is H, $R^1$ is $CH_2$-CN, $R^2$ is $CH_3$;

Compound of Formula (II); R is —$CH_2$CH=CH-(3-quinolyl), $R^p$ is H, W is absent, $R^w$ is H, $R^1$ is $CH_2$-C≡CH, $R^2$ is $CH_3$;

Compound of Formula (II); R is —$CH_2$CH=CH-(3-quinolyl), $R^p$ is H, W is absent, $R^w$ is H, $R^1$ is $CH_2$$CH_2$$CH_3$, $R^2$ is $CH_3$;

Compound of Formula (II); R is —$CH_2$CH=CH-(3-quinolyl), $R^p$ is H, W is absent, $R^w$ is H, $R^1$ is $CH_2$-cyclopropyl, $R^2$ is $CH_3$;

Compound of Formula (II); R is —$CH_2$CH=CH-(3-quinolyl), $R^p$ is H, W is absent, $R^w$ is H, $R^1$ is cyclopropyl, $R^2$ is $CH_3$;

Compound of Formula (II); R is —$CH_2$CH=CH-(3-quinolyl), $R^p$ is H, W is absent, $R^w$ is H, $R^1$ is $CH_2$-(3-pyridyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(cyclo-$C_3H_5$), $R^2$ is $CH_3$;

Compound of Formula (II); R is —$CH_2$CH=CH-(3-quinolyl), $R^p$ is H, W is absent, $R^w$ is H, $R^1$ is $CH_2$$CH_2$$CH_3$, $R^2$ is $CH_3$;

Compound of Formula (II); R is —$CH_2$CH=CH-(3-quinolyl), $R^p$ is H, W is absent, $R^w$ is H, $R^1$ is $CH_2$CH=CH$C_6H_5$, $R^2$ is $CH_3$;

Compound of Formula (II); R is —$CH_2$CH=CH-(3-quinolyl), $R^p$ is H, W is absent, $R^w$ is H, $R^1$ is $CH_2$C(=$CH_2$)C(O)O$CH_3$, $R^2$ is $CH_3$;

Compound of Formula (II); R is —$CH_2$CH=CH-(3-quinolyl), $R^p$ is H, W is absent, $R^w$ is H, $R^1$ is $CH_2$C(=$CH_2$)$CH_3$, $R^2$ is $CH_3$;

Compound of Formula (II); R is —$CH_2$CH=CH-(3-quinolyl), $R^p$ is H, W is absent, $R^w$ is H, $R^1$ is cyclo-$C_3H_5$, $R^2$ is $CH_3$;

Compound of Formula (II); R is —$CH_2$CH=CH-(3-quinolyl), $R^p$ is H, W is absent, $R^w$ is H, $R^1$ is $CH_2$-(3-pyridyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(3-hydroxyphenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-3-tert-butyl-5-methylphenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-3,4-dimethylphenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-3-methoxy-5-(2-propenyl)phenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-3-methoxy-5-methylphenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-5-cyclopentylphenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-5-carboxamidophenyl), $R^2$ is $CH_3$;

Compound of Formula (II); R is —$CH_2$CH=CH-(3-quinolyl), $R^p$ is H, W is absent, $R^w$ is H, $R^1$ is is $CH_2$-(2-hydroxy-3-methoxy-5-(2-methoxycarbonylethyl)phenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-3-methyl-5-fluorophenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-3-methoxy-5-acetylphenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-3-bromophenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-3-methoxy-5-alkoxycarbonylphenyl), $R^2$ is $CH_3$;

Compound of Formula (II); R is —$CH_2$CH=CH-(3-quinolyl), $R^p$ is H, W is absent, $R^w$ is H, $R^1$ is $CH_2$-(2-hydroxy-3-ethylphenyl), $R^2$ is $CH_3$;

Compound of Formula (II); R is —CH$_2$CH=CH-(3-quinolyl), R$^p$ is H, W is absent, R$^w$ is H, R$^1$ is CH$_2$-(2-hydroxy-5-isobutylphenyl), R$^2$ is CH$_3$;

Compound of Formula (II); R is —CH$_2$CH=CH-(3-quinolyl), R$^p$ is H, W is absent, R$^w$ is H, R$^1$ is CH$_2$-(2-hydroxy-3-methyl-5-diethylamino-6-methylphenyl), R$^2$ is CH$_3$;

Compound of Formula (II); R is —CH$_2$CH=CH-(3-quinolyl), R$^p$ is H, W is absent, R$^w$ is H, R$^1$ is CH$_2$-(2-hydroxy-4-methyl-5-bromo-6-methylphenyl), R$^2$ is CH$_3$; and Compound of Formula (II); R is —CH$_2$CH=CH-(3-quinolyl), R$^p$ is H, W is absent, R$^w$ is H, R$^1$ is CH$_2$-(2-hydroxy-3-hydroxymethylphenyl), R$^2$ is CH$_3$.

3. A pharmaceutical composition for treating bacterial infections comprising a therapeutically effective amount of a compound of claim 1 or a pharmaceutically acceptable salt or ester thereof in combination with a pharmaceutically acceptable carrier.

4. A method for treating bacterial infections comprising administering to a mammal in need of such treatment a pharmaceutical composition containing a therapeutically-effective amount of a compound of claim 1 or a pharmaceutically acceptable salt or ester thereof.

5. A compound according to claim 1 having the formula (I)

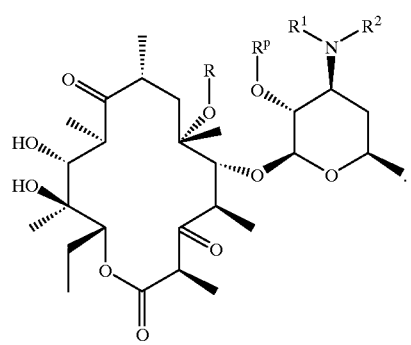

6. A compound according to claim 1 having the formula (II)

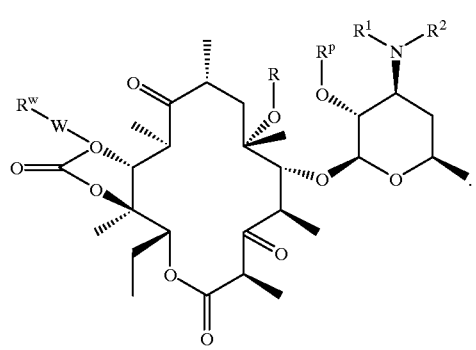

7. A compound according to claim 1 having the formula (III)

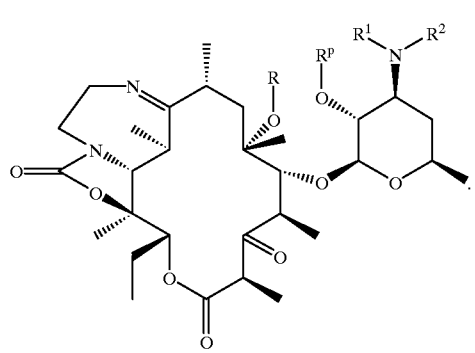

8. A compound according to claim 1 having the formula (IV)

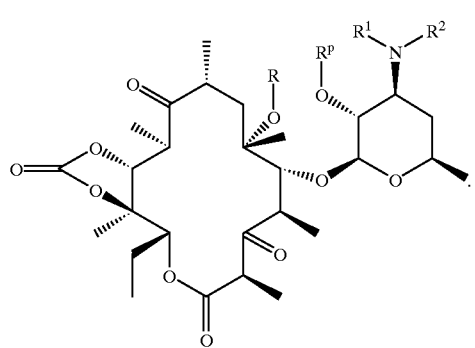

9. A compound according to claim 1 having the formula (V)

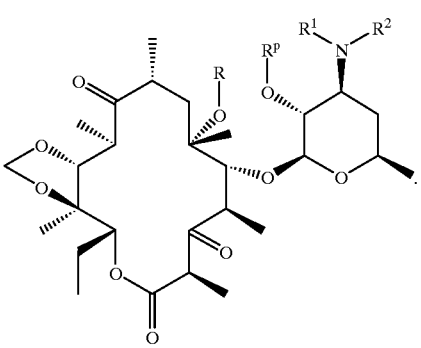

10. A process for preparing a compound selected from the group consisting of

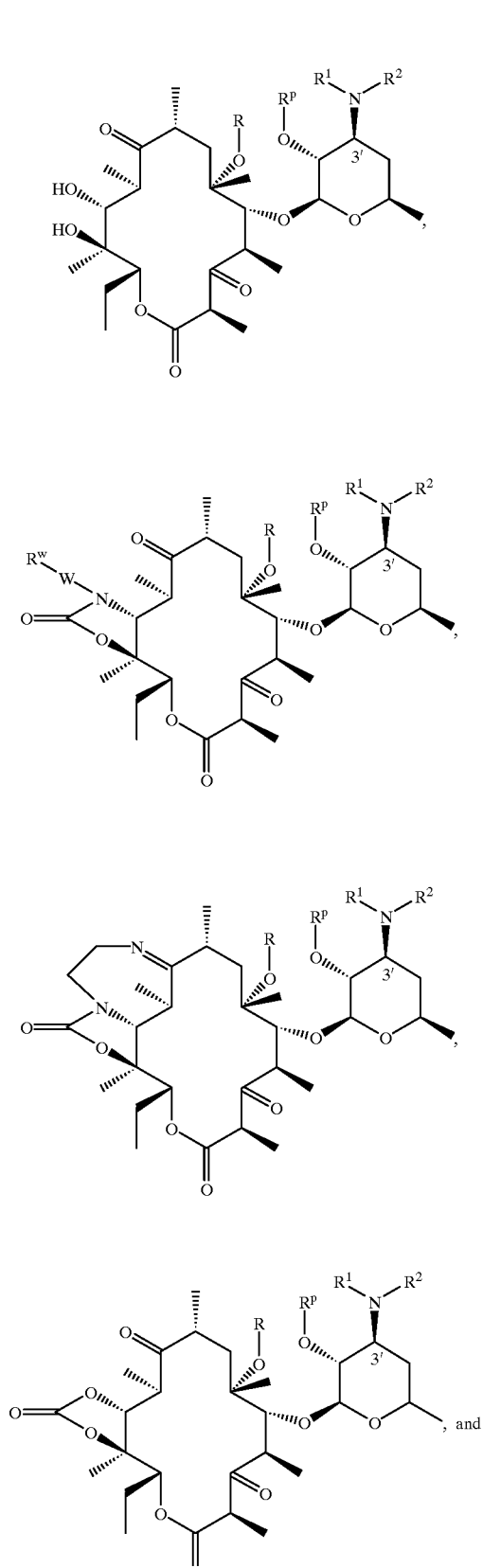

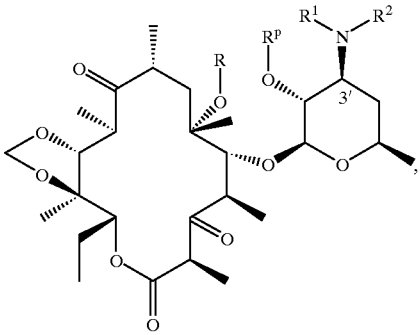

wherein $R^1$ and $R^2$, with the proviso that $R^1$ and $R^2$ are not both methyl, are independently selected from the group consisting of
(1) hydrogen,
(2) $C_1$–$C_6$-alkyl optionally substituted with a substituent selected from the group consisting of
 (a) halogen,
 (b) $C_3$–$C_6$-cycloalkyl,
 (c) aryl,
 (d) substituted aryl,
 (e) heteroaryl,
 (f) substituted heteroaryl,
 (g) —CHO,
 (h) —C(O)—$C_1$–$C_6$-alkyl, and
 (i) —C(O)—NR'R", wherein R' and R" are independently selected from the group consisting of hydrogen, $C_1$–$C_3$-alkyl, $C_1$–$C_3$-alkyl substituted with aryl, substituted aryl, heteroaryl, and substituted heteroaryl,
(3) $C_2$–$C_6$-alkyl optionally substituted with a substituent selected from the group consisting of
 (a) $C_1$–$C_6$-alkoxy,
 (b) —NR'R", wherein R' and R" are as previously defined,
 (c) —NH—C(O)—$C_1$–$C_6$-alkyl,
 (d) —NH—C(O)—O—$C_1$–$C_6$-alkyl,
 (e) —O—C(O)—O—$C_1$–$C_6$-alkyl,
 (f) —O—C(O)—$C_1$–$C_6$-alkyl,
 (g) —CH(=N—O—$C_1$–$C_6$-alkyl),
 (h) —C(=N—O—$C_1$–$C_6$-alkyl)—$C_1$–$C_6$-alkyl,
 (i) —CH(=N—NH—$C_1$–$C_6$-alkyl), and
 (j) —C(=N—NH—$C_1$–$C_6$-alkyl)—$C_1$$C_6$-alkyl,
(4) $C_3$–$C_6$-alkenyl optionally substituted with a substituent selected from the group consisting of
 (a) halogen,
 (b) $C_3$–$C_6$-cycloalkyl,
 (c) aryl,
 (d) substituted aryl,
 (e) heteroaryl,
 (f) substituted heteroaryl,
 (g) —NH—C(O)—$C_1$–$C_6$-alkyl,
 (h) —NH—C(O)—O—$C_1$–$C_6$-alkyl,
 (i) —O—C(O)—O—$C_1$–$C_6$-alkyl, (j) —O—C(O)—$C_1$–$C_6$-alkyl,
(k) —CHO,
(l) —C(O)—$C_1$–$C_6$-alkyl,
(m) —C(O)—NR'R", wherein R' and R" are as previously defined,
(n) —CH(=N—O—$C_1$–$C_6$-alkyl),
(o) —C(=N—O—$C_1$–$C_6$-alkyl)—$C_1$–$C_6$-alkyl,
(p) —CH(=N—NH—$C_1$–$C_6$-alkyl),
(q) —C(=N—NH—$C_1$–$C_6$-alkyl)—$C_1$–$C_6$-alkyl, and
(r) —C(O)—O—$C_1$–$C_6$-alkyl,
(5) $C_3$–$C_6$-alkynyl optionally substituted with a substituent selected from the group consisting of
  (a) halogen,
  (b) $C_3$–$C_6$-cycloalkyl,
  (c) aryl,
  (d) substituted aryl,
  (e) heteroaryl, and
  (f) substituted heteroaryl,
(6) $C_3$–$C_6$-cycloalkyl,
(7) —CHO,
(8) —C(O)—$C_1$–$C_6$-alkyl,
(9) —C(O)—NR'R", wherein R' and R" are as previously defined, and
(10) —C(O)—O—$C_1$–$C_6$-alkyl,
or $R^1$ and $R^2$ taken together may be —$(CH_2)_p$—, wherein p is 3-to-7, which taken together with the nitrogen atom to which they are attached, thus form a heterocyclic ring containing one nitrogen atom and from 3 to 7 carbon atoms;

R is selected from the group consisting of
(1) methyl substituted with a substituent selected from the group consisting of
  (a) —CN,
  (b) —F,
  (c) —$CO_2R^3$ wherein $R^3$ is $C_1$–$C_3$-alkyl, aryl-substituted $C_1$–$C_3$-alkyl, or heteroaryl-substituted $C_1$–$C_3$-alkyl,
  (d) —$S(O)_n$-$R^3$ wherein n is 0, 1, or 2, and $R^3$ is as previously defined,
  (e) —NH—C(O)—$R^3$ where $R^3$ is as previously defined,
  (f) —NH—C(O)—$NR^4R^5$ wherein $R^4$ and $R^5$ are independently selected from the group consisting of
    (i) hydrogen,
    (ii) $C_1$–$C_3$-alkyl,
    (iii) $C_1$–$C_3$-alkyl substituted with aryl,
    (iv) $C_1$–$C_3$-alkyl substituted with substituted aryl,
    (v) $C_1$–$C_3$-alkyl substituted with heteroaryl, and
    (vi) $C_1$–$C_3$-alkyl substituted with and substituted heteroaryl,
  (g) aryl,
  (h) substituted aryl,
  (i) heteroaryl, and
  (j) substituted heteroaryl,
(2) $C_2$–$C_{10}$-alkyl,
(3) $C_2$–$C_{10}$-alkyl substituted with one or more substituents selected from the group consisting of
  (a) halogen,
  (b) hydroxy,
  (c) $C_1$–$C_3$-alkoxy,
  (d) $C_1$–$C_3$-alkoxy-$C_1$–$C_3$-alkoxy,
  (e) oxo,
  (f) —$N_3$,
  (g) —CHO,
  (h) —O—$SO_2$-(substituted $C_1$–$C_6$-alkyl),
  (i) —$NR^6R^7$ wherein $R^6$ and $R^7$ are selected from the group consisting of
    (i) hydrogen,
    (ii) $C_1$–$C_{12}$-alkyl,
    (iii) substituted $C_1$–$C_{12}$-alkyl,
    (iv) $C_1$–$C_{12}$-alkenyl,
    (v) substituted $C_1$–$C_{12}$-alkenyl,
    (vi) $C_1$–$C_{12}$-alkynyl,
    (vii) substituted $C_1$–$C_{12}$-alkynyl,
    (viii) aryl,
    (ix) $C_3$–$C_8$-cycloalkyl,
    (x) substituted $C_3$–$C_8$-cycloalkyl,
    (xi) substituted aryl,
    (xii) heterocycloalkyl,
    (xiii) substituted heterocycloalkyl,
    (xiv) $C_1$–$C_{12}$-alkyl substituted with aryl,
    (xv) $C_1$–$C_{12}$-alkyl substituted with substituted aryl,
    (xvi) $C_1$–$C_{12}$-alkyl substituted with heterocycloalkyl,
    (xvii) $C_1$–$C_{12}$-alkyl substituted with substituted heterocycloalkyl,
    (xviii) $C_1$–$C_{12}$-alkyl substituted with $C_3$–$C_8$-cycloalkyl,
    (xix) $C_1$–$C_{12}$-alkyl substituted with substituted $C_3$–$C_8$-cycloalkyl,
    (xx) heteroaryl,
    (xxi) substituted heteroaryl,
    (xxii) $C_1$–$C_{12}$-alkyl substituted with heteroaryl, and
    (xxiii) $C_1$–$C_{12}$-alkyl substituted with substituted heteroaryl, or
    $R^6$ and $R^7$ are taken together with the atom to which they are attached form a 3–10 membered heterocycloalkyl ring which may be substituted with one or more substituents independently selected from the group consisting of
    (i) halogen,
    (ii) hydroxy,
    (ii) $C_1$–$C_3$-alkoxy,
    (iv) $C_1$–$C_3$-alkoxy-$C_1$–$C_3$-alkoxy,
    (v) oxo,
    (vi) $C_1$–$C_3$-alkyl,
    (vii) halo-$C_1$–$C_3$-alkyl, and
    (vii) $C_1$–$C_3$-alkoxy-$C_1$–$C_3$-alkyl,
  (j) —$CO_2R^3$ wherein $R^3$ is as previously defined,
  (k) —C(O)—$NR^4R^5$ wherein $R^4$ and $R^5$ are as previously defined,
  (l) =N—O—$R^3$ wherein $R^3$ is as previously defined,
  (m) —C≡N,
  (n) —O—$S(O)_n$—$R^3$ wherein n and $R^3$ are as previously defined,
  (o) aryl,
  (p) substituted aryl,
  (q) heteroaryl,
  (r) substituted heteroaryl,
  (s) $C_3$–$C_8$-cycloalkyl,
  (t) substituted $C_3$–$C_8$-cycloalkyl,
  (u) $C_1$–$C_{12}$-alkyl substituted with heteroaryl,
  (v) heterocycloalkyl,
  (w) substituted heterocycloalkyl,
  (x) —NH—C(O)—$R^3$ where $R^3$ is as previously defined,
  (y) —NH—C(O)—$NR^4R^5$ wherein $R^4$ and $R^5$ are as previously defined,
  (z) =N—$NR^6R^7$ wherein $R^6$ and $R^7$ are as previously defined, (aa) =N—R³ wherein R³ is as previously defined,
(bb) =N—NH—C(O)—R⁴ wherein R⁴ is as previously defined, and
(cc) =N—NH—C(O)—NR⁴R⁵ wherein R⁴ and R⁵ are as previously defined,
(4) C₃-alkenyl substituted with a moiety selected from the group consisting of
(a) halogen,
(b) —CHO,
(c) —CO₂R³ where R³ is as previously defined,
(d) —C(O)—R⁴ where R⁴ is as previously defined,
(e) —C(O)—NR⁴R⁵ wherein R⁴ and R⁵ are as previously defined,
(f) —C≡N,
(g) aryl,
(h) substituted aryl,
(i) heteroaryl,
(j) substituted heteroaryl,
(k) C₃–C₇-cycloalkyl, and
(l) C₁–C₁₂-alkyl substituted with heteroaryl,
(5) C₄–C₁₀-alkenyl,
(6) C₄–C₁₀-alkenyl substituted with one or more substituents selected from the group consisting of
(a) halogen,
(b) C₁–C₃-alkoxy,
(c) oxo,
(d) —CHO,
(e) —CO₂R³ where R³ is as previously defined,
(f) —C(O)—NR⁴R⁵ wherein R⁴ and R⁵ are as previously defined,
(g) —NR⁶R⁷ wherein R⁶ and R⁷ are as previously defined,
(h) =N—O—R³ wherein R³ is as previously defined,
(i) —C≡N,
(j) —O—S(O)ₙ—R³ wherein n is 0, 1, or 2 and R³ is as previously defined,
(k) aryl,
(l) substituted aryl,
(m) heteroaryl,
(n) substituted heteroaryl,
(o) C₃–C₇-cycloalkyl,
(p) C₁–C₁₂-alkyl substituted with heteroaryl,
(q) —NH—C(O)—R³ where R³ is as previously defined,
(r) —NH—C(O)—NR⁴R⁵ wherein R⁴ and R⁵ are as previously defined,
(s) =N—NR⁶R⁷ wherein R⁶ and R⁷ are as previously defined,
(t) =N—R³ wherein R³ is as previously defined,
(u) =N—NH—C(O)—R³ where R³ is as previously defined, and
(v) =N—NH—C(O)—NR⁴R⁵ wherein R⁴ and R⁵ are as previously defined,
(7) C₃–C₁₀-alkynyl, and
(8) C₃–C₁₀-alkynyl substituted with one or more substituents selected from the group consisting of
(a) trialkylsilyl,
(b) aryl,
(c) substituted aryl,
(d) heteroaryl, and
(e) substituted heteroaryl,
with the proviso that when R is allyl and R¹ is methyl, R² is not H;
R^p is hydrogen or a hydroxy protecting group;
R^w is selected from the group consisting of
(1) hydrogen,
(2) C₁–C₆-alkyl, optionally substituted with one or more substituents selected from the group consisting of
(a) aryl,
(b) substituted aryl,
(c) heteroaryl,
(d) substituted heteroaryl,
(3) a group selected from option (2) as previously defined further substituted with —CH₂—M—R⁸, wherein M is selected from the group consisting of
(i) —O—,
(ii) —NH—,
(ii) —N(CH₃)—,
(iv) —S(O)ₙ—, wherein n is as described previously,
(v) —NH—C(O)—, and
(vi) —C(O)—NH—, and
R⁸ is selected from the group consisting of
(i) —(CH₂)ₙ-aryl, wherein n is as described previously,
(ii) —(CH₂)ₙ-substituted aryl, wherein n is as described previously,
(iii) —(CH₂)ₙ-heteroaryl, wherein n is as described previously,
(iv) —(CH₂)ₙ-substituted heteroaryl, wherein n is as described previously, and
(v) —(CH₂)ₙ-heterocycloalkyl, wherein n is as described previously; and W is absent or is selected from the group consisting of —O—, —NH— and —N(CH₃)—, the process comprising:
(a) sequentially desmethylating 3'-nitrogen of a compound selected from the group consisting of

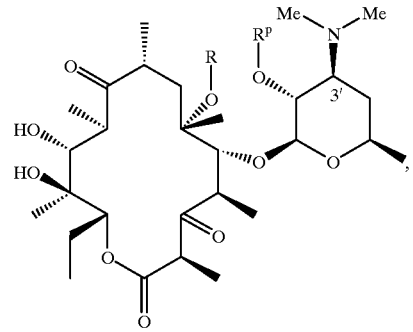

(A)

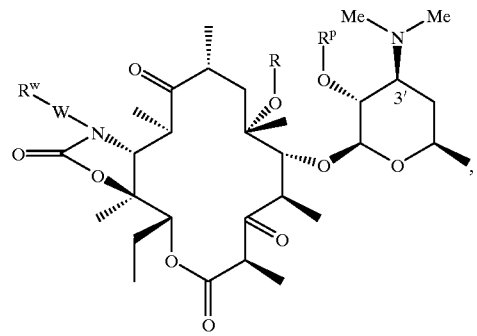

(B)

-continued (C)
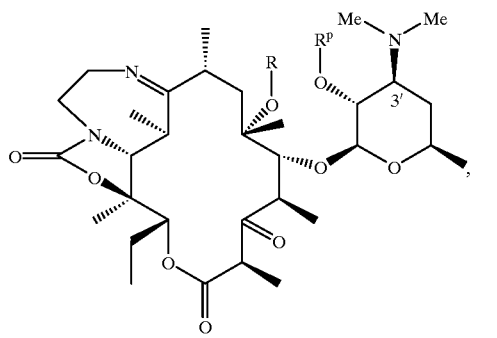

(D)
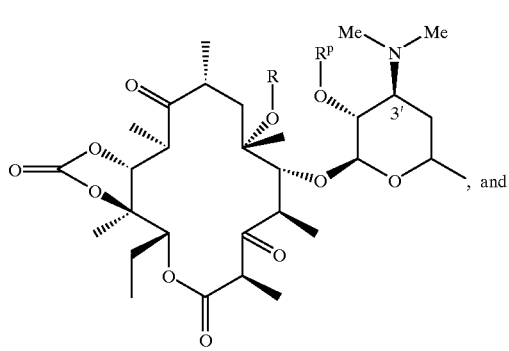
and (E)
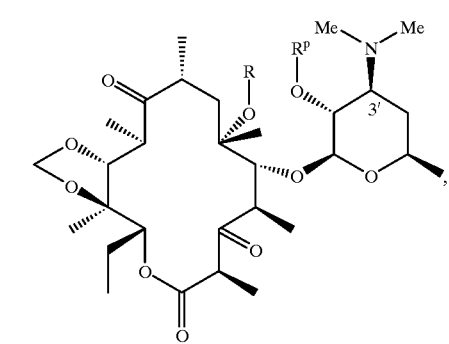

wherein R, and $R^p$ are as defined previously; and (b) sequentially reacting the compound from step (a) with a $R^1$- and a $R^2$-precursor compound.

11. The process of claim 10, wherein the desmethylation of the 3'-nitrogen is obtained by reacting the compound with N-iodosuccinimide to afford a corresponding compound having a 3'-NHCH$_3$ group.

12. The process of claim 11, wherein in step (b), the compound is reacted with a $R^1$-precursor selected from the group consisting of (i) $R^1$—X wherein $R^1$ is as defined previously and X is a halide or sulfonate leaving group, (ii) carbonyldiimidazole to give an intermediate compound wherein $R^1$ is imidazolylcarbonyl and reacting this intermediate with an amine having the formula HNR'R", wherein R' and R" are independently selected from hydrogen, $C_1$–$C_3$-alkyl, $C_1$–$C_3$-alkyl substituted with aryl, substituted aryl, heteroaryl, and substituted heteroaryl, to give a compound wherein $R^1$ is C(O)—NR'R", (iii) an alcohol of the formula HOR', wherein R' is as previously defined, to give a compound wherein $R^1$ is C(O)—OR', (iv) an acylating agent of the formula X—C(O)—R', wherein X is halogen and R' is as defined previously, or O—(C(O)—R')$_2$ to give a compound wherein $R^1$ is C(O)R', and (v) a substituted or unsubstituted aryl alcohol and a homologating agent selected from the group consisting of formaldehyde and paraformaldehyde to give a compound wherein $R^1$ is methyl substituted with substituted aryl.

13. The process of claim 11, further desmethylating the 3'—NHCH$_3$ of the compound with iodosuccinirnide or iodine in presence of light to afford a corresponding compound having a 3'-NH$_2$ group.

14. The process of claim 13, further comprising treating the compound with a $R^1$-precursor to afford a compound having a 3'—NHR$^1$ group, wherein the $R^1$-precursor is selected from the group consisting of (i) $R^1$—X wherein $R^1$ is as defined previously and X is a halide or sulfonate leaving group, (ii) carbonyldiimidazole to give an intermediate compound wherein $R^1$ is imidazolylcarbonyl and reacting this intermediate with an amine having the formula HNR'R", wherein R' and R" are independently selected from hydrogen, $C_1$–$C_3$-alkyl, $C_1$–$C_3$-alkyl substituted with aryl, substituted aryl, heteroaryl, and substituted heteroaryl, to give a compound wherein $R^1$ is C(O)—NR'R", (iii) an alcohol of the formula HOR', wherein R' is as previously defined, to give a compound wherein $R^1$ is C(O)—OR', (iv) an acylating agent of the formula X—C(O)—R', wherein X is halogen and R' is as defined previously, or O—(C(O)—R')$_2$ to give a compound wherein $R^1$ is C(O)R', and (v) a substituted or unsubstituted aryl alcohol and a homologating agent selected from the group consisting of formaldehyde and paraformaldehyde to give a compound wherein $R^1$ is methyl substituted with substituted aryl.

15. The process of claim 14, further comprising treating the compound having 3'—NHR' with a $R^2$-precursor compound to afford a compound having a 3'—NR$^1$R$^2$ group, wherein the $R^2$-precursor is selected from the group consisting of (i) $R^2$—X wherein $R^2$ is as defined previously and X is a halide or sulfonate leaving group, (ii) carbonyldiimidazole to give an intermediate compound wherein $R^2$ is imidazolylcarbonyl and reacting this intermediate with an amine having the formula HNR'R", wherein R' and R" are independently selected from hydrogen, $C_1$–$C_3$-alyl $C_1$–$C_3$-alkyl substituted with aryl, substituted aryl, heteroaryl, and substituted heteroaryl, to give a compound wherein $R^2$ is C(O)—NR'R", (iii) an alcohol of the formula HOR' to give a compound wherein $R^2$ is C(O)—OR', (iv) an acylating agent of the formula X—C(O)—R', wherein X is halogen and R' is as defined previously, or O—(C(O)—R')$_2$ to give a compound wherein $R^2$ is C(O)R', and (v) a substituted or unsubstituted aryl alcohol and homologating agent selected from the group consisting of formaldehyde and paraformaldehyde to give a compound wherein $R^1$ is methyl substituted with substituted aryl.

* * * * *

UNITED STATES PATENT AND TRADEMARK OFFICE
CERTIFICATE OF CORRECTION

PATENT NO. : 6,034,069
DATED : March 7, 2000
INVENTOR(S) : Yat Sun Or et al.

It is certified that error appears in the above-identified patent and that said Letters Patent is hereby corrected as shown below:

Column 62,
Line 61, replace "-SO2" with -- $-SO_2$ --.

Column 64,
Line 20, replace "atkoxy" with -- alkoxy --.

Column 66,
Line 47, replace "is is" with -- is --.

Column 67,
Line 49, replace " 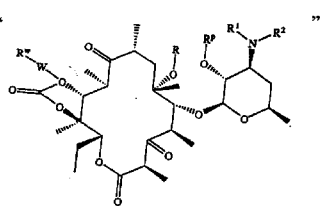 "

with -- 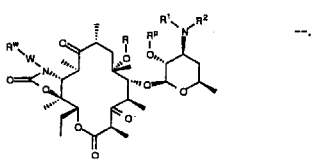 --.

Column 69,
Line 53, replace " 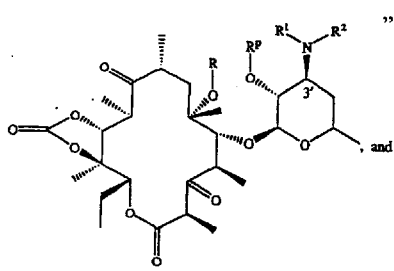 , and with -- 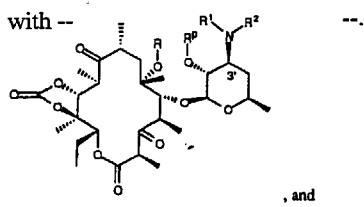 , and

UNITED STATES PATENT AND TRADEMARK OFFICE
CERTIFICATE OF CORRECTION

PATENT NO.    : 6,034,069
DATED         : March 7, 2000
INVENTOR(S)   : Yat Sun Or et al.

It is certified that error appears in the above-identified patent and that said Letters Patent is hereby corrected as shown below:

Column 72,
Line 33, replace "attached form" with -- attached to form --.
Line 44, replace "(vii)" with -- (viii) --.

Column 74,
Line 13, replace "(ii)" with -- (iii) --.

Column 76,
Line 11, replace "iodosuccinirnide" with -- iodosuccinimide --.
Line 51, replace "$C_1$-$C_3$-alyl" with -- $C_1$-$C_3$-alkyl --.

Signed and Sealed this

Twenty-first Day of January, 2003

JAMES E. ROGAN
*Director of the United States Patent and Trademark Office*